United States Patent
Fang et al.

(10) Patent No.: US 10,577,421 B2
(45) Date of Patent: Mar. 3, 2020

(54) ANTI-LAG-3 ANTIBODIES AND USES THEREOF

(71) Applicant: I-MAB, Grand Cayman (KY)

(72) Inventors: Lei Fang, Shanghai (CN); Zhengyi Wang, Shanghai (CN); Bingshi Guo, Shanghai (CN); Jingwu Zang, Shanghai (CN); Wenqing Jiang, Shanghai (CN); Yongqiang Wang, Shanghai (CN)

(73) Assignee: I-MAB, Grand Cayman (KY)

( * ) Notice: Subject to any disclaimer, the term of this patent is extended or adjusted under 35 U.S.C. 154(b) by 0 days.

(21) Appl. No.: 16/069,487

(22) PCT Filed: Feb. 22, 2018

(86) PCT No.: PCT/CN2018/076940
§ 371 (c)(1),
(2) Date: Jul. 11, 2018

(87) PCT Pub. No.: WO2018/153340
PCT Pub. Date: Aug. 30, 2018

(65) Prior Publication Data
US 2019/0225687 A1  Jul. 25, 2019

(30) Foreign Application Priority Data

Feb. 22, 2017 (WO) ................ PCT/CN2017/074365
Jun. 16, 2017 (WO) ................ PCT/CN2017/088570

(51) Int. Cl.
| | |
|---|---|
| C07K 16/28 | (2006.01) |
| A61P 35/00 | (2006.01) |
| A61P 37/04 | (2006.01) |
| A61K 35/17 | (2015.01) |
| A61K 39/00 | (2006.01) |

(52) U.S. Cl.
CPC .......... *C07K 16/2803* (2013.01); *A61K 35/17* (2013.01); *A61P 35/00* (2018.01); *A61P 37/04* (2018.01); *C07K 16/2818* (2013.01); *C07K 16/2827* (2013.01); A61K 2039/505 (2013.01); A61K 2039/507 (2013.01); C07K 2317/21 (2013.01); C07K 2317/24 (2013.01); C07K 2317/33 (2013.01); C07K 2317/53 (2013.01); C07K 2317/55 (2013.01); C07K 2317/56 (2013.01); C07K 2317/565 (2013.01); C07K 2317/75 (2013.01); C07K 2317/76 (2013.01); C07K 2317/92 (2013.01)

(58) Field of Classification Search
None
See application file for complete search history.

(56) References Cited

U.S. PATENT DOCUMENTS

2017/0022273 A1   1/2017  Zhou et al.

FOREIGN PATENT DOCUMENTS

| | | |
|---|---|---|
| CN | 104411723 | 3/2015 |
| CN | 102176921 | 9/2016 |
| CN | 106103484 | 11/2016 |
| WO | WO 2016/028672 | 2/2016 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
He, Y.Y. et al. Lymphocyte-activation gene-3, an important immune checkpoint in cancer *Cancer Science* Sep. 30, 2016 No. 9 vol. 107, pp. 1193-1197.
International Search Report and Written Opinion dated May 22, 2018 for PCT Application No. PCT/CN2018/076940.
Kouo, T. et al. Galectin-3 Shapes Antitumor Immune Responses by Suppressing CD8+ T Cells via LAG-3 and Inhibiting Expansion of Plasmacytoid Dendritic Cells *Cancer Immunology Research* Feb. 7, 2015 No. 4 vol. 3, pp. 412-423.

* cited by examiner

*Primary Examiner* — Nelson B Moseley, II
(74) *Attorney, Agent, or Firm* — Sheppard Mullin Richter & Hampton LLP

(57) ABSTRACT

The present disclosure provides antibodies that bind Lymphocyte Activation Gene-3 (LAG-3). Also provided are methods of stimulating an immune response, inhibiting growth of tumor cells, and treating an autoimmune, inflammatory, or viral disease.

11 Claims, 17 Drawing Sheets
Specification includes a Sequence Listing.

ANTI-LAG-3 ANTIBODIES AND USES THEREOF

CROSS REFERENCE TO RELATED APPLICATIONS

The present application is the U.S. national stage application of International Application PCT/CN2018/076940, filed Feb. 22, 2018, which claims priority to International Application PCT/CN2017/088570, filed Jun. 16, 2017 and International Application PCT/CN2017/074365, filed Feb. 22, 2017, the contents of each of which are incorporated herein by reference in their entireties in the present disclosure.

FIELD OF THE DISCLOSURE

The present disclosure relates generally to the field of molecular biology and protein biochemistry. More specifically, the disclosure relates to antibodies that bind to Lymphocyte Activation Gene-3 (LAG-3) and methods of use thereof.

BACKGROUND

Lymphocyte Activation Gene-3 (LAG-3) (also known as CD223) is a member of the immunoglobulin (Ig) superfamily, is closely related to CD4, and variously impacts T cell function. LAG-3 is expressed on activated T cells, exhausted T cells, tumor infiltrating T cells, and regulatory T cells ($T_{regs}$). Upon binding with major histocompatibility complex 2 (MHC class II), the LAG-3/MHC class II interaction results in the negative regulation of T cell proliferation, activation, and homeostasis.

LAG-3 represents an important immune checkpoint in cancer, similarly to cytotoxic T lymphocyte antigen-4 (CTLA-4), programmed cell death ligand-1 (PD-L1), and programmed cell death-1 (PD-1). LAG-3 not only expresses on the activated/exhausted effector T cells but also on regulatory T cells. LAG3 antagonism can not only promote the activation of effector T cells, but also block the suppressive function of regulatory T cells. Therefore, LAG-3 represents a promising target for cancer immunotherapy and preclinical evidence suggests that an anti-LAG-3 antibody can promote an anti-tumor response.

In view of the above, a need exists for developing novel agents that modulate the activity of LAG-3 in a manner that stimulates an immune response that inhibits the growth of various cancers and tumor cells, as well as being useful in the treatment of autoimmune, inflammatory, or viral diseases.

SUMMARY

The present disclosure provides antibodies and fragments thereof capable of binding to human Lymphocyte Activation Gene-3 (LAG-3) protein, as well as their uses in therapeutic, diagnostic and analytical settings. As demonstrated in the experimental examples, some of the anti-LAG-3 antibodies disclosure herein exhibited activities not shown with known anti-LAG-3 antibodies. For instance, the presently disclosed antibodies may inhibit the binding of the LAG-3 protein to Galectin-3 (LGALS3) and C-type lectin domain family 4 member G (LSECtin) protein, in addition to the binding to MHC class II molecules. Known anti-LAG-3 antibodies, by contrast, have only shown inhibitory effect to the binding to MHC class II molecules. In some embodiments, the antibodies and fragment thereof of the present disclosure are capable of reversing the inhibitory effect of regulatory T cells ($T_{regs}$) on effector T cells ($T_{effs}$).

In one embodiment, the present disclosure provides an isolated antibody or fragment thereof, wherein the antibody or fragment thereof has specificity to a human Lymphocyte Activation Gene-3 (LAG-3) protein, wherein the antibody or fragment thereof comprises a heavy chain variable region comprising heavy chain complementarity determining regions CDRH1, CDRH2, and CDRH3, and a light chain variable region comprising light chain complementarity determining regions CDRL1, CDRL2, and CDRL3, wherein the CDRH1 comprises the amino acid sequence of SEQ ID NO:240 or an amino acid sequence derived from SEQ ID NO:240 with one or two amino acid substitution; the CDRH2 comprises the amino acid sequence of SEQ ID NO:241 or an amino acid sequence derived from SEQ ID NO:241 with one or two amino acid substitution; the CDRH3 comprises the amino acid sequence of SEQ ID NO:242 or an amino acid sequence derived from SEQ ID NO:242 with one or two amino acid substitution; the CDRL1 comprises the amino acid sequence of SEQ ID NO:243 or an amino acid sequence derived from SEQ ID NO:243 with one or two amino acid substitution; the CDRL2 comprises the amino acid sequence of SEQ ID NO:244 or an amino acid sequence derived from SEQ ID NO:244 with one or two amino acid substitution; and the CDRL3 comprises the amino acid sequence of SEQ ID NO:245 or an amino acid sequence derived from SEQ ID NO:245 with one or two amino acid substitution.

In some embodiments, the amino acid substitution from SEQ ID NO:240 is at amino acid residue Y27, T28, T30, G35, or the combinations thereof, according to Kabat numbering. In some embodiments, the amino acid substitution is selected from: Y27: F; T28: M, or L; T30: E, D, or G; or G35: W, or S. In some embodiments, the CDRH1 comprises an amino acid sequence selected from the group consisting of SEQ ID NO:240 and 339-346.

In some embodiments, the amino acid substitution from SEQ ID NO:241 is at amino acid residue D50, Y52, Y56, N58, or the combinations thereof, according to Kabat numbering. In some embodiments, the amino acid substitution is selected from: D50: E; Y52: F; Y56: I, V, L, or H; or N58: V, or T. In some embodiments, the amino acid substitution comprises N58V. In some embodiments, the CDRH2 comprises an amino acid sequence selected from the group consisting of SEQ ID NO:241 and 347-353.

In some embodiments, the amino acid substitution from SEQ ID NO:242 is at amino acid residue N96, G99, Y102, or the combinations thereof, according to Kabat numbering. In some embodiments, the amino acid substitution is selected from: N96: D, or G; G99: K, R, or Q; or Y102: H. In some embodiments, the amino acid substitution comprises G99K or Y102H. In some embodiments, the CDRH3 comprises an amino acid sequence selected from the group consisting of SEQ ID NO:242 and 354-361.

In some embodiments, the amino acid substitution from SEQ ID NO:243 is at amino acid residue N28, according to Kabat numbering. In some embodiments, the amino acid substitution comprises N28Q. In some embodiments, the CDRL2 comprises an amino acid sequence of SEQ ID NO:376.

In some embodiments, the amino acid substitution from SEQ ID NO:244 is at amino acid residue Q50, V51, S52, L54, S56, or the combinations thereof, according to Kabat numbering. In some embodiments, the amino acid substitution is selected from: Q50: H; V51: K; S52: D; L54: R; or S56: R, V, L, or T. In some embodiments, the CDRL2 comprises an amino acid sequence selected from the group consisting of SEQ ID NO:244 and 362-369.

In some embodiments, the amino acid substitution from SEQ ID NO:245 is at amino acid residue A89, N91, L94, or the combinations thereof, according to Kabat numbering. In some embodiments, the amino acid substitution is selected from: A89: G; N91: Y; or L94: M, or E. In some embodiments, the amino acid substitution comprises N91Y. In some embodiments, the CDRL3 comprises an amino acid sequence selected from the group consisting of SEQ ID NO:245 and 370-375.

In some embodiments, the antibody or fragment comprises a heavy chain variable region comprising an amino acid sequence selected from the group consisting of SEQ ID NO:238, 246-259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, and 337, or a peptide having at least 90% sequence identity to an amino acid sequence selected from the group consisting of SEQ ID NO:238, 246-259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, and 337.

In some embodiments, the antibody or fragment comprises a light chain variable region comprising an amino acid sequence selected from the group consisting of SEQ ID NO:239, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, and 338, or a peptide having at least 90% sequence identity to an amino acid sequence selected from the group consisting of SEQ ID NO:239, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, and 338.

Back mutations can be incorporated to the humanized antibodies or fragments. In some embodiments, the heavy chain variable region comprises one or more amino acid residues selected from the group consisting of: (a) Ala (A) at position 71, (b) Leu (L) at position 69, (c) Lys (K) at position 66, (d) Ala (A) at position 67, (e) Ile (I) at position 48, (f) Ile (I) at position 37, (g) Lys (K) at position 38, (h) Phe (F) at position 91, and (i) Glu (E) at position 1, according to Kabat numbering, and combinations thereof.

In another embodiment, provided is an isolated antibody or fragment thereof, wherein the antibody or fragment thereof has specificity to a human Lymphocyte Activation Gene-3 (LAG-3) protein, wherein the antibody or fragment thereof comprises a heavy chain variable region comprising heavy chain complementarity determining regions CDRH1, CDRH2, and CDRH3, and a light chain variable region comprising light chain complementarity determining regions CDRL1, CDRL2, and CDRL3, wherein: the CDRH1 comprises the amino acid sequence of SEQ ID NO:1 or 2 or an amino acid sequence derived from SEQ ID NO:1 or 2 with one or two amino acid substitution; the CDRH2 comprises the amino acid sequence of SEQ ID NO:3 or 4 or an amino acid sequence derived from SEQ ID NO:3 or 4 with one or two amino acid substitution; the CDRH3 comprises an amino acid sequence selected from the group consisting of SEQ ID NO:5-45 or an amino acid sequence derived from any one of SEQ ID NO:5-45 with one or two amino acid substitution; the CDRL1 comprises an amino acid sequence selected from the group consisting of SEQ ID NO:46-80 or an amino acid sequence derived from any one of SEQ ID NO:46-80 with one or two amino acid substitution; the CDRL2 comprises an amino acid sequence selected from the group consisting of SEQ ID NO:81-103 or an amino acid sequence derived from any one of SEQ ID NO:81-103 with one or two amino acid substitution; and the CDRL3 comprises an amino acid sequence selected from the group consisting of SEQ ID NO:104-139 or an amino acid sequence derived from any one of SEQ ID NO:104-139 with one or two amino acid substitution.

In some embodiments, the antibody or fragment comprises a heavy chain variable region comprising an amino acid sequence selected from the group consisting of SEQ ID NO:140-188 or a peptide having at least 90% sequence identity to an amino acid sequence selected from the group consisting of SEQ ID NO:140-188. In some embodiments, the antibody or fragment comprises a light chain variable region comprising an amino acid sequence selected from the group consisting of SEQ ID NO:189-237 or a peptide having at least 90% sequence identity to an amino acid sequence selected from the group consisting of SEQ ID NO:189-237.

Bispecific antibodies are also provided which further comprises a second specificity to an immune checkpoint protein or a tumor antigen. In some embodiments, the bispecificity comprises a second specificity to a protein target selected from the group consisting of PD-L1, PD-1, CTLA-4, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA, KIR, CD47, CD73, EGFR, Her2, CD33, CD133, CEA and VEGF.

Methods of treatments are provided as well, including the treatment of autoimmune or inflammatory disease, cancer, and infections.

DETAILED DESCRIPTION

Figure 1:
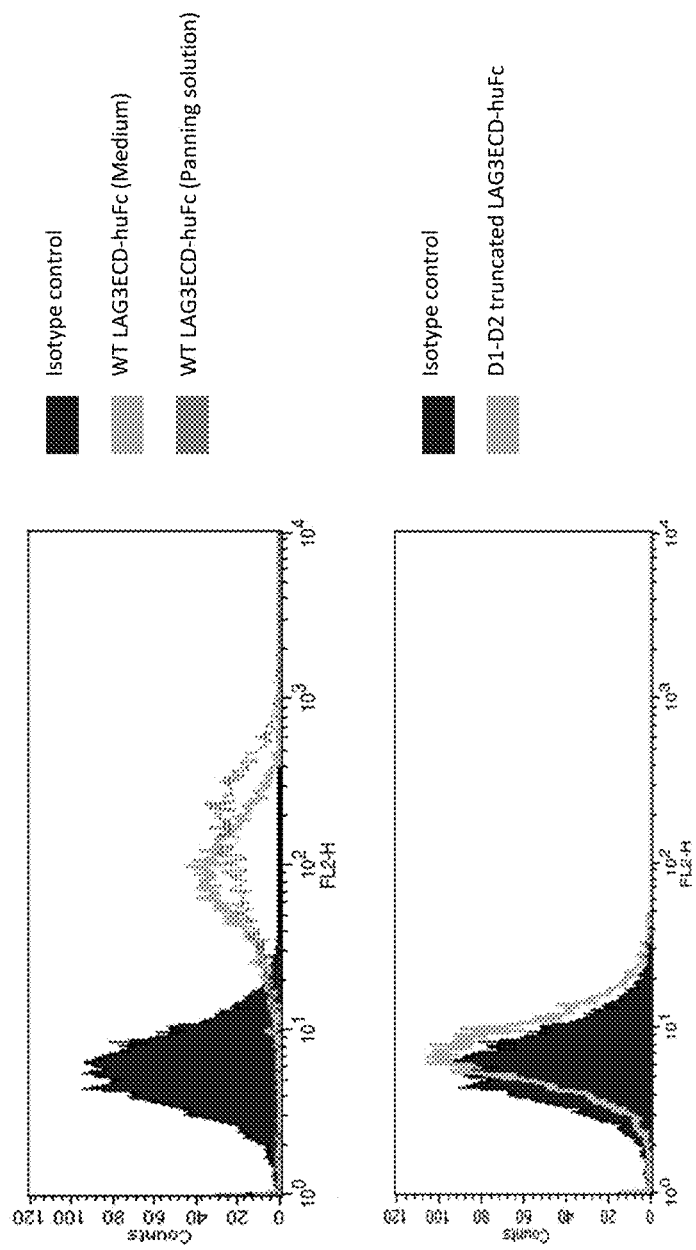
FIG. 1. The D1-D2 domains are important for LAG-3 function. Wildtype (WT) LAG3 extracellular domain (ECD) fusion protein (LAG-3-ECD-huFc) fragments can bind to Daudi cells while D1-D2 truncated LAG-3-ECD-huFc fragments fail to bind Daudi cells.

The present disclosure relates to isolated antibodies, particularly human and humanized antibodies, which bind to human LAG-3 and that have desirable functional properties. In some embodiments, the LAG-3 antibodies can bind to LAG-3 and inhibit its binding to other molecules. In some embodiments, the other molecules include, without limitation, Galectin-3 (LGALS3), C-type lectin domain family 4 member G (LSECtin) protein, and MHC class II molecules.

In certain embodiments, the antibodies of the disclosure include certain CDR regions as disclosed herein. This disclosure provides isolated antibodies, methods of making such antibodies, immunoconjugates and bispecific molecules comprising such antibodies and pharmaceutical compositions containing the antibodies, immunoconjugates or bispecific molecules of the disclosure. This disclosure also relates to methods of using the antibodies, such as to detect LAG-3 protein, as well as to methods of using the anti-LAG-3 antibodies of the disclosure to stimulate immune responses, alone or in combination with other therapeutic agents. Accordingly, this disclosure also provides methods of using the anti-LAG-3 antibodies of the disclosure to, for example, inhibit tumor growth or treat viral infection.

In order that the present disclosure may be more readily understood, certain terms are first defined. Additional definitions are set forth throughout the detailed description.

The term "LAG-3" or "LAG3" refers to Lymphocyte Activation Gene-3. The LAG3 protein, which belongs to immunoglobulin (Ig) superfamily, comprises a 503-amino acid type I transmembrane protein with four extracellular Ig-like domains, designated D1 to D4. As described herein, the term "LAG-3" includes variants, isoforms, homologs, orthologs, and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species but not all other species (e.g., cross-react with monkey LAG-3, but not mouse LAG-3). The term "human LAG-3" refers to human sequence LAG-3, such as the complete amino acid sequence of human LAG-3 having GenBank Accession No. NP 002277. The term "mouse LAG-3" refers to mouse sequence LAG-3, such as the complete amino acid sequence of mouse LAG-3 having GenBank Accession No. NP 032505. LAG-3 is also known in the art as, for example, CD223. The human LAG-3 sequence may differ from human LAG-3 of GenBank Accession No. NP 002277 by having, e.g., conserved mutations or mutations in non-conserved regions and the LAG-3 has substantially the same biological function as the human LAG-3 of GenBank Accession No. NP 002277. For example, a biological function of human LAG-3 is having an epitope in the extracellular domain of LAG-3 that is specifically bound by an antibody of the instant disclosure or a biological function of human LAG-3 is binding to MHC Class II molecules.

A particular human LAG-3 sequence will generally be at least 90% identical in amino acids sequence to human LAG-3 of GenBank Accession No. NP 002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of GenBank Accession No. NP 002277. In certain embodiments, a human LAG-3 sequence will display no more than 10 amino acid differences from the LAG-3 sequence of GenBank Accession No. NP 002277. In certain embodiments, the human LAG-3 can display no more than 5, or even no more than 4, 3, 2, or 1 amino acid difference from the LAG-3 sequence of GenBank Accession No. NP 002277. Percent identity can be determined as described herein.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$, and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or simply "antibody portion" or "fragment"), as used herein, refers to one or more fragments of an antibody that retain the ability to specifically bind to an antigen (e.g., a LAG-3 protein). It has been shown that the antigen-binding function of an antibody can be performed by fragments of a full-length antibody. Examples of binding fragments encompassed within the term "antigen binding portion" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a $F_v$ fragment consisting of the $V_L$ and $V_H$ domains of a single arm of an antibody, (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain $F_v$ (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG-3 protein is substantially free of antibodies that specifically bind antigens other than LAG-3 proteins). An isolated antibody that specifically binds a human LAG-3 protein may, however, have cross reactivity to other antigens, such as LAG-3 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

Humanized antibodies are antibodies from non-human species whose protein sequences have been modified to increase their similarity to antibody variants produced naturally in humans. The process of "humanization" is usually applied to monoclonal antibodies developed for administration to humans.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds human LAG-3" or "has specificity to human LAG-3" is intended to refer to an antibody that binds to human LAG-3 protein (and possibly a LAG-3 protein from one or more non-human species) but does not substantially bind to non-LAG-3 proteins. Preferably, the antibody binds to a human LAG-3 protein with "high affinity", namely with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, more preferably $25 \times 10^{-9}$ M or less or even more preferably $1 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more. The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

The term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less, and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the disclosure are described in further detail in the following subsections.

Anti-LAG-3 Antibodies and Fragments

The present disclosure provides antibodies and fragments having specificity to human Lymphocyte Activation Gene-3 (LAG-3) protein. Demonstrated are human antibody as well as mouse and humanized antibodies that have high affinity to LAG-3 as well as other desired activities associated with the binding. The antibodies of the disclosure are characterized by particular functional features or properties of the antibodies.

An example group of anti-LAG-3 antibodies and fragments was derived from mouse antibody 147H (see Table 5). An example humanized chimeric antibody, along with a number of humanized antibody fragments with back mutations are shown in Table 6. Further, based on affinity maturation, additional antibodies and fragments were prepared that had improved properties (Table 7 and 8). In some embodiments, provided is an isolated antibody or fragment thereof, wherein the antibody or fragment thereof has specificity to a human Lymphocyte Activation Gene-3 (LAG-3) protein and comprises a VH CDR1 of SEQ ID NO:240, a VH CDR2 of SEQ ID NO:241, a VH CDR3 of SEQ ID NO:242, a VL CDR1 of SEQ ID NO:243, a VL CDR2 of SEQ ID NO:244, and a VL CDR3 of SEQ ID NO:245.

In one embodiment, the antibody or fragment thereof comprises a heavy chain variable region comprising heavy chain complementarity determining regions CDRH1, CDRH2, and CDRH3, and a light chain variable region comprising light chain complementarity determining regions CDRL1, CDRL2, and CDRL3, wherein the CDRH1 comprises the amino acid sequence of SEQ ID NO:240 or an amino acid sequence derived from SEQ ID NO:240 with one or two amino acid substitution; the CDRH2 comprises the amino acid sequence of SEQ ID NO:241 or an amino acid sequence derived from SEQ ID NO:241 with one or two amino acid substitution; the CDRH3 comprises the amino acid sequence of SEQ ID NO:242 or an amino acid sequence derived from SEQ ID NO:242 with one or two amino acid substitution; the CDRL1 comprises the amino acid sequence of SEQ ID NO:243 or an amino acid sequence derived from SEQ ID NO:243 with one or two amino acid substitution; the CDRL2 comprises the amino acid sequence of SEQ ID NO:244 or an amino acid sequence derived from SEQ ID NO:244 with one or two amino acid substitution; and the CDRL3 comprises the amino acid sequence of SEQ ID NO:245 or an amino acid sequence derived from SEQ ID NO:245 with one or two amino acid substitution.

Non-limiting examples of amino acid residues on which substitutions can be made are shown in Table 8. For instance, in CDRH2, such residues include D50, Y52, Y56 and N58. In a preferred embodiment, the CDRH2 includes the N58V substitution, optionally with other substitutions (e.g., SEQ ID NO: 347). In another example, a CDRH3 substitution occurs at N96, G99 or Y102. In a preferred embodiment, the CDRH3 includes substitution G99K, Y102, or the combination (e.g., SEQ ID NO: 354). In yet another example, a CDRL3 substitution occurs at A89, N91, or L94. In a preferred embodiment, the CHRL3 includes substitution N91Y (e.g., SEQ ID NO: 374). In one embodiment, the antibody or fragment includes all of N58V, G99K, Y102, and N91Y, optionally with other substitutions.

In some embodiments, the antibody or fragment comprises a heavy chain variable region comprising an amino acid sequence selected from the group consisting of SEQ ID NO:238, 246-259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, and 337, or a peptide having at least 90% sequence identity to an amino acid sequence selected from the group consisting of SEQ ID NO:238, 246-259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, and 337.

In some embodiments, the antibody or fragment comprises a light chain variable region comprising an amino acid sequence selected from the group consisting of SEQ ID NO:239, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, and 338, or a peptide having at least 90% sequence identity to an amino acid sequence selected from the group consisting of SEQ ID NO:239, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, and 338.

In some embodiments, the antibody or fragment thereof further comprises a heavy chain constant region, a light chain constant region, an Fc region, or the combination thereof. In some embodiments, the light chain constant region is a kappa or lambda chain constant region.

Without limitation, the antibody or fragment thereof is a chimeric antibody, a humanized antibody, or a fully human antibody. In one aspect, antibody or fragment thereof is a humanized antibody.

For a humanized antibody or fragment, certain back mutations can be incorporated. In some embodiments, the heavy chain variable region comprises one or more amino acid residues selected from the group consisting of:

(a) Ala (A) at position 71,
(b) Leu (L) at position 69,
(c) Lys (K) at position 66,
(d) Ala (A) at position 67,
(e) Ile (I) at position 48,
(f) Ile (I) at position 37,
(g) Lys (K) at position 38,
(h) Phe (F) at position 91, and
(i) Glu (E) at position 1, according to Kabat numbering, and combinations thereof.

In some embodiments, the heavy chain variable region comprises Ala (A) at position 71. In some embodiments, the heavy chain variable region comprises Leu (L) at position 69. In some embodiments, the heavy chain variable region comprises Lys (K) at position 66. In some embodiments, the heavy chain variable region comprises Ala (A) at position 67. In some embodiments, the heavy chain variable region comprises Ile (I) at position 48. In some embodiments, the heavy chain variable region comprises Ile (I) at position 37. In some embodiments, the heavy chain variable region comprises Lys (K) at position 38. In some embodiments, the heavy chain variable region comprises Phe (F) at position 91. In some embodiments, the heavy chain variable region comprises Glu (E) at position 1.

In some embodiments, the heavy chain variable region comprises one or more amino acid residues selected from the group consisting of
(a) Ala (A) at position 71,
(b) Leu (L) at position 69,
(c) Lys (K) at position 66,
(d) Ala (A) at position 67,
(e) Ile (I) at position 48,
(f) Ile (I) at position 37, and
(g) Lys (K) at position 38, according to Kabat numbering, and combinations thereof. In some embodiments, the heavy chain variable region comprises all of the above recited residues.

In some embodiments, the antibody or fragment thereof comprises a heavy chain variable region comprising an amino acid sequence of SEQ ID NO:238, or a peptide having at least 90% sequence identity to SEQ ID NO:238. In some embodiments, the antibody or fragment thereof comprises a light chain variable region comprising an amino acid sequence of SEQ ID NO:239, or a peptide having at least 90% sequence identity to SEQ ID NO:239.

In some embodiments, the antibody or fragment thereof comprises a heavy chain variable region comprising an amino acid sequence selected from the group consisting of SEQ ID NO:246-259, or a peptide having at least 90% sequence identity to an amino acid sequence selected from the group consisting of SEQ ID NO:246-259. In some embodiments, the antibody or fragment thereof comprises a light chain variable region comprising an amino acid sequence of SEQ ID NO:239, or a peptide having at least 90% sequence identity to SEQ ID NO:260.

In some embodiments, the antibody or fragment thereof comprises a heavy chain variable region comprising an amino acid sequence of SEQ ID NO:246, or a peptide having at least 90% sequence identity to SEQ ID NO:246. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:247, or a peptide having at least 90% sequence identity to SEQ ID NO:247. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:248, or a peptide having at least 90% sequence identity to SEQ ID NO:248. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:249, or a peptide having at least 90% sequence identity to SEQ ID NO:249. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:250, or a peptide having at least 90% sequence identity to SEQ ID NO:250. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:251, or a peptide having at least 90% sequence identity to SEQ ID NO:251. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:252, or a peptide having at least 90% sequence identity to SEQ ID NO:252. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:253, or a peptide having at least 90% sequence identity to SEQ ID NO:253. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:254, or a peptide having at least 90% sequence identity to SEQ ID NO:254. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:255, or a peptide having at least 90% sequence identity to SEQ ID NO:255. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:256, or a peptide having at least 90% sequence identity to SEQ ID NO:256. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:257, or a peptide having at least 90% sequence identity to SEQ ID NO:257. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:258, or a peptide having at least 90% sequence identity to SEQ ID NO:258. In some embodiments, the antibody or fragment thereof comprises a light chain variable region comprising an amino acid sequence of SEQ ID NO:260, or a peptide having at least 90% sequence identity to SEQ ID NO:260.

In some embodiments, the antibody or fragment thereof comprises a heavy chain variable region comprising an amino acid sequence of SEQ ID NO:259, or a peptide having at least 90% sequence identity to SEQ ID NO:259. In some embodiments, the antibody or fragment thereof comprises a light chain variable region comprising an amino acid sequence of SEQ ID NO:260, or a peptide having at least 90% sequence identity to SEQ ID NO:260.

In any of these example heavy chain variable or light chain variable regions, the CDRs can be modified as illustrated in Table 8 or replaced by the example modified CDRs as shown in Table 8.

In various embodiments, an antibody of the disclosure comprises heavy and light chain variable regions comprising amino acid sequences that are homologous to the amino acid sequences of the preferred antibodies described herein, and wherein the antibodies retain the desired functional properties of the anti-LAG-3 antibodies of the disclosure. For example, the antibody specifically binds to human LAG-3; blocks LAG-3 binding to major histocompatibility complex (MHC) class II molecules, Galectin-3 and LSECtin; stimulates an immune response; and reverses the inhibitory effect of regulatory T cells on effector cells.

Additionally, or alternatively, the antibody can possess one or more of the following functional properties discussed above, such as high affinity binding to human LAG-3, binding to monkey LAG-3, lack of binding to mouse LAG-3, the ability to inhibit binding of LAG-3 to MHC Class II molecules and/or the ability to stimulate antigen-specific T cell responses.

In various embodiments, the antibody can be, for example, a human antibody, a humanized antibody or a chimeric antibody. In other embodiments, the $V_H$ and/or $V_L$ amino acid sequences can be 85%, 90%, 95%, 96%, 97%, 98%, or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acids of $V_H$ and/or $V_L$ amino acid sequences, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci. 4:11-7, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-53, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally, or alternatively, the protein sequences of the present disclosure can further be used as a "query sequence" to perform a search against public databases to, e.g., to identify related sequences. Such searches can be performed using the XBLAST program (version 2.0) of Altschul et al. (J. Mol. Biol. 215:403-10, 1990). BLAST protein searches can be performed with the XBLAST program, score=50, word length=3 to obtain amino acid sequences homologous to the antibody molecules of the disclosure. To obtain gapped alignments for comparison purposes, Gapped BLAST can be utilized as described in Altschul et al. (Nucl. Acid Res. 25(17):3389-402, 1997). When utilizing BLAST and Gapped BLAST programs, the default parameters of the respective programs (e.g., XBLAST and NB LAST) are useful.

In some embodiments, the sequence identity is at least 95%, 96%, 97%, 98%, 99% or 99.5%. In some embodiments, the sequence identity encompasses amino acid substitution, deletion or addition of one, two, three, four, five, six, seven, eight, nine of ten residues. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the tables below, where a similarity score of 0 or higher indicates conservative substitution between the two amino acids.

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 |
| F | −4 | −5 | −5 | −3 | −4 | −3 | −6 | −5 | −4 | −5 | −2 | −5 | −4 | −1 | 0 | 1 | 2 | 9 |
| L | −6 | −4 | −3 | −3 | −2 | −2 | −4 | −3 | −3 | −2 | −2 | −3 | −3 | 2 | 4 | 2 | 6 |
| I | −2 | −3 | −2 | −1 | −1 | 0 | −2 | −2 | −2 | −2 | −2 | −2 | −2 | 4 | 2 | 5 |
| M | −5 | −3 | −2 | −2 | −1 | −1 | −3 | −2 | 0 | −1 | −2 | 0 | 0 | 2 | 6 |
| V | −2 | −1 | −1 | −1 | 0 | 0 | −2 | −2 | −2 | −2 | −2 | −2 | −2 | 4 |
| R | −4 | −3 | 0 | 0 | −2 | −1 | −1 | −1 | 0 | 1 | 2 | 3 | 6 |
| K | −5 | −2 | −1 | 0 | −1 | 0 | 0 | 0 | 1 | 1 | 0 | 5 |
| H | −3 | −2 | 0 | −1 | −1 | −1 | 1 | 1 | 2 | 3 | 6 |
| Q | −5 | −1 | 0 | −1 | 0 | −1 | 2 | 2 | 1 | 4 |
| N | −4 | 0 | −1 | 1 | 0 | 0 | 2 | 1 | 2 |
| E | −5 | 0 | −1 | 0 | 0 | 0 | 3 | 4 |
| D | −5 | 1 | −1 | 0 | 0 | 0 | 4 |
| T | −2 | 0 | 0 | 1 | 1 | 3 |
| A | −2 | 1 | 1 | 1 | 2 |
| S | 0 | 1 | 1 | 1 |
| P | −3 | −1 | 6 |
| G | −3 | 5 |
| C | 12 |

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Human antibodies were also prepared herein. The human antibodies or fragments may include heavy chain CDRs as shown in Table 2. Examples of heavy chain variable regions are shown in Table 1. The human antibodies or fragments may include light chain CDRs as shown in Table 4. Examples of heavy chain variable regions are shown in Table 3.

In one embodiment, accordingly, provided is an isolated antibody or fragment thereof, wherein the antibody or fragment thereof has specificity to a human Lymphocyte Activation Gene-3 (LAG-3) protein, wherein the antibody or fragment thereof comprises a heavy chain variable region comprising heavy chain complementarity determining regions CDRH1, CDRH2, and CDRH3, and a light chain variable region comprising light chain complementarity determining regions CDRL1, CDRL2, and CDRL3, wherein: the CDRH1 comprises the amino acid sequence of SEQ ID NO:1 or 2 or an amino acid sequence derived from SEQ ID NO:1 or 2 with one or two amino acid substitution; the CDRH2 comprises the amino acid sequence of SEQ ID NO:3 or 4 or an amino acid sequence derived from SEQ ID NO:3 or 4 with one or two amino acid substitution; the CDRH3 comprises an amino acid sequence selected from the group consisting of SEQ ID NO:5-45 or an amino acid sequence derived from any one of SEQ ID NO:5-45 with one or two amino acid substitution; the CDRL1 comprises an amino acid sequence selected from the group consisting of SEQ ID NO:46-80 or an amino acid sequence derived from any one of SEQ ID NO:46-80 with one or two amino acid substitution; the CDRL2 comprises an amino acid sequence selected from the group consisting of SEQ ID NO:81-103 or an amino acid sequence derived from any one of SEQ ID NO:81-103 with one or two amino acid substitution; and the CDRL3 comprises an amino acid sequence selected from the group consisting of SEQ ID NO:104-139 or an amino acid sequence derived from any one of SEQ ID NO:104-139 with one or two amino acid substitution.

In some embodiments, the antibody or fragment includes the same three heavy chain CDRs as one of the combination as shown in Table. 2. For instance, the heavy chain may include CDRH1 of SEQ ID NO: 1, CDRH2 of SEQ ID NO:3 and CDRH3 of SEQ ID NO:5, as shown in the first row. In some embodiments, the antibody or fragment includes the same three light chain CDRs as one of the combination as shown in Table. 4. For instance, the light chain may include CDRL1 of SEQ ID NO: 46, CDRL2 of SEQ ID NO:81 and CDRL3 of SEQ ID NO:104, as shown in the first row.

In some embodiments, the antibody or fragment comprises a heavy chain variable region comprising an amino acid sequence selected from the group consisting of SEQ ID NO:140-188 or a peptide having at least 90% sequence identity to an amino acid sequence selected from the group consisting of SEQ ID NO:140-188. In some embodiments, the antibody or fragment comprises a light chain variable region comprising an amino acid sequence selected from the group consisting of SEQ ID NO:189-237 or a peptide having at least 90% sequence identity to an amino acid sequence selected from the group consisting of SEQ ID NO:189-237.

In some embodiments, the sequence identity is at least 95%, 96%, 97%, 98%, 99% or 99.5%. In some embodiments, the sequence identity encompasses amino acid substitution, deletion or addition of one, two, three, four, five, six, seven, eight, nine of ten residues. Such substitutions, in some embodiments, are conservative substitutions.

The antibodies of the disclosure are characterized by particular functional features or properties of the antibodies. For example, the antibodies specifically bind to human LAG-3 and may bind to LAG-3 from certain other species, e.g., monkey LAG-3, e.g., cynomolgus monkey, rhesus monkey, but may not substantially bind to LAG-3 from certain other species, e.g., mouse LAG-3. Preferably, an antibody of the disclosure binds to human LAG-3 with high affinity.

The ability of the antibody to stimulate an immune response, such as an antigen-specific T cell response, can be indicated by, for example, the ability of the antibody to stimulate interleukin-2 (IL-2) or interferon gamma (IFN-γ) production in an antigen-specific T cell response. In certain embodiments, an antibody of the disclosure binds to human LAG-3 and exhibits an ability to stimulate an antigen-specific T cell response. In other embodiments, an antibody of the disclosure binds to human LAG-3 but does not exhibit an ability to stimulate an antigen-specific T cell response. Other means by which to evaluate the ability of the antibody to stimulate an immune response include the ability of the antibody to inhibit tumor growth, such as in an in vivo tumor graft model or the ability of the antibody to stimulate an autoimmune response, such as the ability to promote the development of an autoimmune disease in an autoimmune model, such as the ability to promote the development of diabetes in the NOD mouse model.

The binding of an antibody of the disclosure to LAG-3 can be assessed using one or more techniques well established in the art. For example, in a preferred embodiment, an antibody can be tested by a flow cytometry assay in which the antibody is reacted with a cell line that expresses human LAG-3, such as CHO cells that have been transfected to express LAG-3, e.g., human LAG-3, or monkey LAG-3, e.g., rhesus or cynomolgus monkey or mouse LAG-3 on their cell surface. Other suitable cells for use in flow cytometry assays include anti-CD3-stimulated CD4$^+$ activated T cells, which express native LAG-3. Additionally, or alternatively, the binding of the antibody, including the binding kinetics (e.g., $K_D$ value) can be tested in BIAcore binding assays. Still other suitable binding assays include ELISA assays, for example using a recombinant LAG-3 protein. Preferably, an antibody of the disclosure binds to a LAG-3 protein with a $K_D$ of $5 \times 10^{-8}$ M or less, binds to a LAG-3 protein with a $K_D$ of $2 \times 10^{-8}$ M or less, binds to a LAG-3 protein with a $K_D$ of $5 \times 10^{-9}$ M or less, binds to a LAG-3 protein with a $K_D$ of $4 \times 10^{-9}$ M or less, binds to a LAG-3 protein with a $K_D$ of $3 \times 10^{-9}$ M or less, binds to a LAG-3 protein with a $K_D$ of $2 \times 10^{-9}$ M or less, binds to a LAG-3 protein with a $K_D$ of $125 \times 10^{-9}$ M or less, binds to a LAG-3 protein with a $K_D$ of $5 \times 10^{-10}$ M or less, or binds to a LAG-3 protein with a $K_D$ of $1 \times 10^{-10}$ M or less.

Preferred antibodies of the disclosure are the human monoclonal antibodies S27, S31, T99, and 5119 isolated and structurally characterized as described [Examples 2-8]. The $V_H$ amino acid sequences of S27, S31, T99 and S119 are shown in SEQ ID NO:149, SEQ NO:150, SEQ ID NO:158, and SEQ ID NO:162, respectively. The $V_L$ amino acid sequences of S27, S31, T99, and S119 are shown in SEQ ID NO:198, SEQ NO:199, SEQ ID NO:207, and SEQ ID NO:211, respectively.

Given that each of these antibodies can bind to human LAG-3, the $V_H$ and $V_L$ sequences can be "mixed and matched" to create other anti-LAG-3 binding molecules of the disclosure. Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NO: 140-SEQ ID NO:188 and (b) a light chain variable region comprising an amino acid sequence selected from the group consisting of SEQ ID NO:189-SEQ ID NO:237 wherein the antibody specifically binds human LAG-3.

Preferred variable heavy and variable light chain combinations include:

(a) a heavy chain variable region comprising the amino acid sequence of SEQ ID NO:149 and a light chain variable region comprising the amino acid sequence of SEQ ID NO:198;

(b) a heavy chain variable region comprising the amino acid sequence of SEQ ID NO:150 and a light chain variable region comprising the amino acid sequence of SEQ ID NO:199;

(c) a heavy chain variable region comprising the amino acid sequence of SEQ ID NO:158 and a light chain variable region comprising the amino acid sequence of SEQ ID NO:207;

(d) a heavy chain variable region comprising the amino acid sequence of SEQ ID NO:162 and a light chain variable region comprising the amino acid sequence of SEQ ID NO:211.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *Brit. J. of Can.* 83(2):252-60, 2000; Beiboer et al., *J. Mol. Biol.* 296:833-49, 2000; Rader et al., *PNAS* 95:8910-15, 1998; Barbas et al., *JACS* 116:2161-2, 29914; Barbas et al., *PNAS* 92:2529-33, 1995; Ditzel et al., *J. Immunol.* 157:739-49, 1996; Berezov et al., *BIA Journal* 8(1): Scientific Review, 2001; Igarashi et al., *J. Biochem* 117:452-7, 1995; Bourgeois et al., *J. Virol.* 72:807-10, 1998; Levi et al., *PNAS* 90:4374-8, 1993; Polymenis and Stoller, *J. Immunol.* 152:5218-329, 1994; and Xu and Davis, *Immunity* 13:37-45, 2000. See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to human LAG-3. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to LAG-3. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody. Within other aspects, the present disclosure provides monoclonal antibodies comprising one or more heavy and/or light chain CDR3 domain from a human antibody, such as, e.g., a human antibody obtained from a non-human animal, wherein the human antibody is capable of specifically binding to human LAG-3. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to human LAG-3 and wherein the CDR3 domain from the first human antibody replaces a CDR3 domain in a human antibody that is lacking binding specificity for LAG-3 to generate a second human antibody that is capable of specifically binding to human LAG-3. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Engineered and Modified Antibodies

As used herein, the terms "humanized", "humanization", and the like, refer to grafting of the murine monoclonal antibody CDRs disclosed herein to human FRs and constant regions. Also encompassed by these terms are possible further modifications to the murine CDRs, and human FRs, by the methods disclosed in, for example, Kashmiri et al. (*Methods*, 36(1):25-34, 2005) and Hou et al. (*J. Biochem.* 144(1):115-20, 2008), respectively, to improve various antibody properties, as discussed below.

As used herein, the term "FR" or "framework sequence" refers to any one of FRs 1 to 4. Humanized antibodies and antigen binding fragments encompassed by the present disclosure include molecules wherein any one or more of FRs 1 to 4 is substantially or fully human, i.e., wherein any of the possible combinations of individual substantially or fully human FRs 1 to 4, is present. For example, this includes molecules in which FR1 and FR2, FR1 and FR3, FR1, FR2, and FR3, etc., are substantially or fully human. Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

Fully human frameworks are those that are identical to a known human germline framework sequence. Human FR germline sequences can be obtained from the international ImMunoGeneTics (IMGT) database and from The Immunoglobulin FactsBook by Marie-Paule Lefranc and Gerard Lefranc, Academic Press, 2001, the contents of which are herein incorporated by reference in their entirety.

CDRs encompassed by the present disclosure include not only those specifically disclosed herein, but also CDR sequences having sequence identities of at least 80%, at least 85%, at least 90%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, or 5 amino acid changes at corresponding positions compared to CDR sequences disclosed herein. Such sequence identical, or amino acid modified, CDRs preferably bind to the antigen recognized by the intact antibody.

Humanized antibodies in addition to those disclosed herein exhibiting similar functional properties according to the present disclosure can be generated using several different methods Almagro et al. (Front. Biosci., Humanization of antibodies January 1(13):1619-33, 2008). In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (*PNAS* 88:2869, 1991). Additional references describing methods useful to generate humanized variants based on homology and back mutations include as described in Olimpieri et al. (*Bioinformatics* February 1; 31(3):434-5, 2015) and U.S. Pat. Nos. 4,816,397, 5,225,539, and 5,693,761; and the method of Winter and co-workers (Jones et al., *Nature* 321:522-5, 1996; Riechmann et al., *Nature* 332:323-7, 1988; and Verhoeyen et al., *Science* 239:1534-6, 1988).

Antibodies of the disclosure can be tested for binding to human LAG-3 by, for example, standard ELISA. Anti-LAG-3 human IgG antibodies can be further tested for reactivity with a LAG-3 antigen by Western blotting. The binding specificity of an antibody of the disclosure can also be determined by monitoring binding of the antibody to cells expressing a LAG-3 protein, e.g., flow cytometry. These methods are known in the art. See, e.g., Harlow and Lane (1988), cited supra.

Bi-Functional Molecules

Antibodies of this disclosure can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA cross linkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADC scan be prepared as described in U.S. Pat. Nos. 7,087,600; 6,989,452; and 7,129, 261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

In another aspect, the present disclosure features bispecific molecules comprising an anti-LAG-3 antibody linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In a preferred embodiment, the bispecific molecule comprises a first binding specificity for LAG-3 and a second binding specificity for a triggering molecule that recruits cytotoxic effector cells that can kill a LAG-3 expressing target cell. Examples of suitable triggering molecules are CD64, CD89, CD16, and CD3. See, e.g., Kufer et al., Trends in Biotech. 22(5):238-44, 2004.

In an embodiment, a bispecific molecule has, in addition to an anti-Fc binding specificity and an anti-LAG-3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T cell (e.g. via CD2, CD3, CDS, CD28, CD4, CD40, or ICAM-1), other immune regulatory molecules (e.g. via PD-1, PD-L1, CTLA-4, CD122, 4-1BB, TIM3, OX-40, OX40L, CD40L, LIGHT, ICOS, ICOSL, GITR, GITRL, TIGIT, CD27, VISTA, B7H3, B7H4, HEVM, BTLA, KIR, CD47 or CD73) or other immune cell, resulting in an increased immune response against the target cell.

As an immune receptor modulator, an antibody or antigen-binding fragment specific to LAG-3 can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, $\alpha V\beta 3$, $\alpha 5\beta 1$, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis. Non-limiting examples of bispecificity in this respect include LAG-3/EGFR, LAG-3/Her2, LAG-3/CD33, LAG-3/CD133, LAG-3/CEA and LAG-3/VEGF.

Different format of bispecific antibodies are also provided. In some embodiments, each of the anti-LAG-3 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to LAG-3, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-$\alpha$, CD40L, OX40L, CD27L, CD30L, 4-1BBL, LIGHT and GITRL. Such bi-functional molecules can combine the immune checkpoint blocking effect with tumor site local immune modulation.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al., supra; Cao and Suresh, Bioconjugate Chem. 9(6):635-44, 1988; and van Spriel et al., Immunol. Today 21(8):391-7, 2000; and the references cited therein.

Pharmaceutical Compositions

In another aspect, the present disclosure provides a pharmaceutical composition comprising an antibody of the present disclosure formulated together with a pharmaceutically acceptable earlier. It may optionally contain one or more additional pharmaceutically active ingredients, such as another antibody or a drug. The pharmaceutical compositions of the disclosure also can be administered in a combination therapy with, for example, another immunostimulatory agent, anti-cancer agent, an anti-viral agent, or a vaccine, such that the anti-LAG-3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference. Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Alternatively, an antibody of the disclosure can be administered via a non-parenteral route, such as a topical, epidermal or mucosal route of administration, e.g., intranasally, orally, vaginally, rectally, sublingually or topically.

The pharmaceutical compounds of the disclosure can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxyl alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every 3 to 6 months. Preferred dosage regimens for an anti-LAG-3 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL.

A "therapeutically effective dosage" of an anti-LAG-3 antibody of the disclosure preferably results in a decrease in severity of disease symptoms, an increase infrequency and duration of disease symptom-free periods, or a prevention of impairment or disability due to the disease affliction. For example, for the treatment of tumor bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the disclosure can be formulated to ensure proper distribution in vivo. For example, to ensure that the therapeutic compounds of the disclosure cross the blood-brain barrier, they can be formulated in liposomes, which may additionally comprise targeting moieties to enhance selective transport to specific cells or organs. See, e.g., U.S. Pat. Nos. 4,522,811; 5,374,548; 5,416,016; and 5,399,331; V. V. Ranade, *J. Clin. Pharmacol.* 29:685, 1989; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J.*

*Biol. Chem.* 269:9090; Keinanen and Laukkanen (1994) *FEBS Lett.* 346:123; and Killion and Fidler (1994) *Immunomethods* 4:273.

Uses and Methods

The antibodies, antibody compositions and methods of the present disclosure have numerous in vitro and in vivo utilities involving, for example, detection of LAG-3 or enhancement of immune response by blockade of LAG-3. In a preferred embodiment, the antibodies of the present disclosure are human antibodies. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-LAG-3 antibodies can be administered together with an antigen of interest or the antigen may already be present in the subject to be treated (e.g., a tumor bearing or virus-bearing subject). When antibodies to LAG-3 are administered together with another agent, the two can be administered in either order or simultaneously.

The disclosure further provides methods for detecting the presence of humanLAG-3 antigen in a sample, or measuring the amount of human LAG-3 antigen, comprising contacting the sample, and a control sample, with a human monoclonal antibody, or an antigen binding portion thereof, which specifically binds to human LAG-3, under conditions that allow for formation of a complex between the antibody or portion thereof and human LAG-3. The formation of a complex is then detected, wherein a difference complex formation between the sample compared to the control sample is indicative the presence of human LAG-3 antigen in the sample. Moreover, the anti-LAG-3 antibodies of the disclosure can be used to purify human LAG-3 via immunoaffinity purification.

Given the ability of anti-LAG-3 antibodies of the disclosure to inhibit the binding of LAG-3 to MHC Class II molecules and to stimulate antigen-specific T cell responses, the disclosure also provides in vitro and in vivo methods of using the antibodies of the disclosure to stimulate, enhance or upregulate antigen-specific T cell responses. For example, the disclosure provides a method of stimulating an antigen-specific T cell response comprising contacting said T cell with the antibody of the disclosure such that an antigen-specific T cell response is stimulated. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 production by the antigen specific T cell is stimulated.

The disclosure also provides a method of stimulating an immune response (e.g., an antigen-specific T cell response) in a subject comprising administering an antibody of the disclosure to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another aspect, the disclosure provides a method for inhibiting growth of tumor cells in a subject comprising administering to the subject an antibody of the disclosure such that growth of the tumor is inhibited in the subject. In yet another aspect, the disclosure provides a method of treating viral infection in a subject comprising administering to the subject an antibody of the disclosure such that the viral infection is treated in the subject.

These and other methods of the disclosure are discussed in further detail below.

Cancer

Blockade of LAG-3 by antibodies can enhance the immune response to cancerous cells in the patient. In one aspect, the present disclosure relates to treatment of a subject in vivo using an anti-LAG-3 antibody such that growth of cancerous tumors is inhibited. An anti-LAG-3 antibody can be used alone to inhibit the growth of cancerous tumors. Alternatively, an anti-LAG-3 antibody can be used in conjunction with other immunogenic agents, standard cancer treatments, or other antibodies, as described below.

Accordingly, in one embodiment, the disclosure provides a method of inhibiting growth of tumor cells in a subject, comprising administering to the subject a therapeutically effective amount of an anti-LAG-3 antibody, or antigen-binding portion thereof. Preferably, the antibody is a human anti-LAG-3 antibody (such as any of the human anti-human LAG-3 antibodies described herein). Additionally or alternatively, the antibody can be a chimeric or humanized anti-LAG-3 antibody.

Preferred cancers whose growth may be inhibited using the antibodies of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g., hormone refractory prostate adenocarcinoma), breast cancer, colon cancer and lung cancer (e.g., non-small cell lung cancer). Additionally, the disclosure includes refractory or recurrent malignancies whose growth may be inhibited using the antibodies of the disclosure. Examples of other cancers that can be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) *Int. Immunol.* 17:133-144).

Optionally, antibodies to LAG-3 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below).

In humans, some tumors have been shown to be immunogenic such as melanomas. By raising the threshold of T cell activation by LAG-3 blockade, the tumor responses in the host can be activated.

LAG-3 blockade is likely to be more effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepare dusing autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. LAG-3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with LAG-3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6: 332-336). As a method of vaccination, DC immunization can be effectively combined with LAG-3 blockade to activate more potent anti-tumor responses.

LAG-3 blockade can also be combined with standard cancer treatments. LAG-3 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-LAG-3 antibody in combination with decarbazine for the treatment of melanoma. Another example of such a combination is an anti-LAG-3 antibody in combination with interleukin-2 (IL-2) for the treatment of melanoma. The scientific rationale behind the combined use of LAG-3 blockade and chemotherapy is that cell death, that is a consequence of the cytotoxic action of most chemotherapeutic compounds, should result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors can also be combined with LAG-3 blockade. Inhibition of angiogenesis leads to tumor cell death which may feed tumor antigen into host antigen presentation pathways.

LAG-3 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used totarget two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard &O'Garra (1992) *Immunology Today* 13: 198-200), and Fas ligand (Hahne et al. (1996) *Science* 4: 1363-1365). Antibodies to each of these entities can be used in combination with anti-LAG-3 to counteract the effects of the immunosuppressive agent and favor tumor immune responses by the host.

Other antibodies which activate host immune responsiveness can be used in combination with anti-LAG-3. These include molecules on the surface of dendritic cells which activate DC function and antigen presentation. Anti-CD40 antibodies are able to substitute effectively for T cell helper activity (Ridge et al. (1998) Nature 393: 474-478) and can be used in conjunction with LAG-3 antibodies (Ito et al. (2000) *Immunobiology* 201 (5) 527-40). Activating antibodies toT cell costimulatory molecules such as CTLA-4 (e.g., U.S. Pat. No. 5,811,097), OX-40 (Weinberg et al. (2000) *Immunol.* 164:2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. LAG-3 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-LAG-3 antibodies can increase the frequency and activity of the adoptively transferred T cells.

Cellular therapies, and more specifically chimeric antigen receptor (CAR) T-cell therapies, are also provided in the present disclosure. A suitable T cell can be used, that is put in contact with an anti-LAG-3 antibody of the present disclosure (or alternatively engineered to express an anti-LAG-3 antibody of the present disclosure). Upon such contact or engineering, the T cell can then be introduced to a cancer patient in need of a treatment. The cancer patient may have a cancer of any of the types as disclosed herein. The T cell can be, for instance, a tumor-infiltrating T lymphocyte, a $CD4^+$ T cell, a $CD8^+$ T cell, or the combination thereof, without limitation.

In some embodiments, the T cell was isolated from the cancer patient him- or her-self. In some embodiments, the T cell was provided by a donor or from a cell bank. When the T cell is isolated from the cancer patient, undesired immune reactions can be minimized.

Infectious Diseases

Other methods of the disclosure are used to treat patients that have been exposed to particular toxins or pathogens. Accordingly, another aspect of the disclosure provides a method of treating an infectious disease in a subject comprising administering to the subject an anti-LAG-3 antibody, or antigen-binding portion thereof, such that the subject is treated for the infectious disease. Preferably, the antibody is a human anti-human LAG-3 antibody (such as any of the human anti-human LAG-3 antibodies described herein). Additionally or alternatively, the antibody can be a chimeric or humanized antibody.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Some examples of pathogenic viruses causing infections treatable by methods of the disclosure include HIV, hepatitis (A, B, or C), herpes virus (e.g., VZV, HSV-1, HAV-6, HSV-11, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTL-V virus, dengue virus, papilloma virus, molluscum virus, poliovirus, rabies virus, JC virus and arboviral encephalitis virus.

Some examples of pathogenic bacteria causing infections treatable by methods ofthe disclosure include *chlamydia*, rickettsial bacteria, mycobacteria, staphylococci, streptococci, pneumonococci, meningococci and gonococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the disclosure include *Candida albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, LAG-3 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Bolligeri (1993) *Proc. Natl. Acad. Sci. USA* 90:6444-6448; Poljak (1994) *Structure* 2:1121-1123).

Autoimmune Reactions

Anti-LAG-3 antibodies may provoke and amplify autoimmune responses. Indeed, induction of anti-tumor responses using tumor cell and peptide vaccines revealsthat many anti-tumor responses involve anti-self reactivities (van Elsas et al. (2001) *J.* 112 *Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol.* 19 (1): 81-4). Therefore, it is possible to consider using anti-LAG-3 blockade in conjunction with various self-proteins in order to devise vaccination protocols to efficiently generate immune responses against these self-proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self-proteins can also be used as targets such as IgE for the treatment of allergy and asthma, and TNFα for rheumatoid arthritis. Finally, antibody responses to various hormones may be induced by the use of anti-LAG-3 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-LAG-3 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

Anti-LAG-3 antibodies can be used to stimulate antigen-specific immune responses by co-administration of an anti-LAG-3 antibody with an antigen of interest (e.g., a vaccine). Accordingly, in another aspect the disclosure provides a method of enhancing an immune response to an antigen in a subject, comprising administering to the subject: (i) the antigen; and (ii) an anti-LAG-3 antibody, or antigen-binding portion thereof, such that an immune response to the antigen in the subject is enhanced. Preferably, the antibody is a human anti-human LAG-3 antibody (such as any of the human anti-LAG-3 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multi-specific and bispecific molecules and immunoconjugates) of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-LAG-3 antibodies of the disclosure can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/mL dose once every four weeks and adriamycin is intravenously administered as a 60-75 mg/mL dose once every 21 days. Co-administration of the human anti-LAG-3 antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising the antibody compositions of the disclosure (e.g., human antibodies, bispecific or multi-specific molecules, or immunoconjugates) and instructions for use. The kit can further contain at least one additional reagent, or one or more additional human antibodies of the disclosure (e.g., a human antibody having a complementary activity which binds to an epitope inLAG-3 antigen distinct from the first human antibody). Kits typically include a label indicating the intended use of the contents of the kit. The term label includes any writing, or recorded material supplied on or with the kit, or which otherwise accompanies the kit.

Nervous System Disorders

Other methods of the disclosure are used to treat patients that have a progressive disorder of the nervous system that affects movement. In one embodiment, the progressive disorder of the nervous system that affects movement is Parkinson's disease. Accordingly, another aspect of the disclosure provides a method of treating Parkinson's disease in a subject comprising administering to the subject an anti-LAG-3 antibody, or antigen-binding portion thereof, such that the subject is treated for Parkinson's disease. Preferably, the antibody is a human anti-human LAG-3 antibody (such as any of the human anti-LAG-3 antibodies described herein). Additionally or alternatively, the antibody can be a chimeric or humanized antibody.

In addition to immune system organ e.g. thymus and spleen, LAG3 is enriched in the brain as well (C. J. Workman (2002), Eur. J. Immunol. 32, 2255-2263). Immunoblot analysis indicates that LAG3 is expressed predominantly in neurons. According to the Allen Brain Atlas, LAG3 is localized to neurons throughout the central nervous system (CNS), including DA neurons. X. Mao et al., (Science. 2016 Sep. 30; 353(6307)) reported that LAG3 preferentially binds α-synuclein (α-syn) misfolded preformed fibrils (PFF) with high affinity mainly through its D1 domain (29-167AA). In addition, deletion of the D2 (168-252AA), D3 (265-343AA), or intracellular domain (ICD, 472-525AA) substantially weakens binding of LAG3 to α-syn PFF, X. Mao et al have shown that α-syn PFF binding to LAG3 initiated α-syn PFF endocytosis, transmission, and toxicity. Emerging evidence indicates that the pathogenesis of Parkinson's disease (PD) may be due to cell-to-cell transmission of misfolded α-syn PFF. Parkinson's disease (PD) is the second most common neurodegenerative disorder and leads to slowness of movement, tremor, rigidity, and, in the later stages of PD, cognitive impairment. Pathologically, PD is characterized by the accumulation of α-synuclein in Lewy bodies and neurites. There is degeneration of neurons throughout the nervous system, with the degeneration of dopamine neurons in the substantia nigra pars compacta leading to the major symptoms of PD. Anti-LAG3 antibody specifically bind to D1 or D2 domain can reduce α-syn PFF toxicity and cell-to-cell transmission, suggesting its potential for PD therapy. As shown in the Example 1, our antibody can specifically bind to D1 or D2 domain of LAG3 protein. Therefore, there antibody can be used for the PD therapy.

Combination Therapy

In another aspect, the disclosure provides methods of combination therapy in which an anti-LAG-3 antibody is co-administered with one or more additional antibodies that are effective in stimulating immune responses to thereby further enhance, stimulate or upregulate immune responses in a subject. For example, the disclosure provides a method for stimulating an immune response in a subject comprising administering to the subject an anti-LAG-3 antibody and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the subject is administered an anti-LAG-3 antibody and an anti-PD-1 antibody. In another embodiment, the subject is administered an anti-LAG-3 antibody and an anti-PD-L1 antibody. In yet another embodiment, the subject is administered an anti-LAG-3 antibody and an anti-CTLA-4 antibody. In one embodiment, the anti-LAG-3 antibody is a human antibody, such as an antibody of the disclosure. Alternatively, the anti-LAG-3 antibody can be, for example, a chimeric or humanized antibody (e.g., prepared from a mouse anti-LAG-3 mAb). In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a hyperproliferative disease (e.g., cancer), comprising administering a LAG-3 antibody and a CTLA-4 antibody to a subject. In further embodiments, the anti-LAG-3 antibody is administered at a subtherapeutic dose, the anti-CTLA-4 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering an anti-LAG-3 antibody and a subtherapeutic dose of anti-CTLA-4 antibody to a subject. In certain embodiments, the subject is human. In certain embodiments, the anti-CTLA-4 antibody is human sequence monoclonal antibody 10D1 (described in PCT Publication WO 01114424) and the anti-LAG-3 antibody is human sequence monoclonal antibody, such as S27, S31, T99, or S119 as described herein. Other anti-CTLA-4 antibodies encompassed by the methods of the present disclosure include, for example, those disclosed in: WO98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. In certain embodiments, the anti-CTLA-4 antibody binds to human CTLA-4 with a $K_D$ of $5\times10^{-8}$ M or less, binds to human CTLA-4 with a $K_D$ of $1\times10^{-8}$ M or less, binds to human CTLA-4 with a $K_D$ of $5\times10^{-9}$ M or less, or binds to human CTLA-4 with a $K_D$ of between $1\times10^{-8}$ M and $1\times10^{-10}$ M or less.

In one embodiment, the present disclosure provides a method for treating a hyperproliferative disease (e.g., cancer), comprising administering a LAG-3 antibody and a PD-1 antibody to a subject. In further embodiments, the anti-LAG-3 antibody is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering an anti-LAG-3 antibody and a subtherapeutic dose of anti-PD-1 antibody to a subject. In certain embodiments, the subject is human. In certain embodiments, the anti-PD-1 antibody is a human sequence monoclonal antibody and the anti-LAG-3 antibody is human sequence monoclonal antibody, such as S27, S31, T99, or S119 as described herein. Examples of human sequence anti PD-1 antibodies include 17D8, 2D3, 4H1, 5C4 and 4A11, which are described in PCT Publication WO 061121168. In certain embodiments, the anti-PD-1 antibody binds to human PD-1 with a $K_D$ of $5\times10^{-8}$ M or less, binds to human PD-1 with a $K_D$ of $1\times10^{-8}$ M or less, binds to human PD-1 with a $K_D$ of $5\times10^{-9}$ M or less, or binds to human PD-1 with a $K_D$ of between $1\times10^{-8}$ M and $1\times10^{-10}$ M or less.

In one embodiment, the present disclosure provides a method for treating a hyperproliferative disease (e.g., cancer), comprising administering a LAG-3 antibody and a PD-L1 antibody to a subject. In further embodiments, the anti-LAG-3 antibody is administered at a subtherapeutic dose, the anti-PD-L1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering an anti-LAG-3 antibody and a subtherapeutic dose of anti-PD-L1 antibody to a subject. In certain embodiments, the subject is human. In certain embodiments, the anti-PD-L1 antibody is a human sequence monoclonal antibody and the anti-LAG-3 antibody is human sequence monoclonal antibody, such as S27, S31, T99, or S119 as described herein. Examples of human sequence anti-PD-L1 antibodies include 3G10, 12A4, 10A5, 5F8, 10H10, 1B12, 7H1, 11E6, 12B7 and 13G4, which are described in PCT Publication WO 07/005874. In certain embodiments, the anti-PD-L1 antibody binds to human PD-L1 with a $K_D$ of $5\times10^{-8}$ M or less, binds to human PD-L1 with a $K_D$ of $1\times10^{-8}$ M or less, binds to human PD-L1 with a $K_D$ of $5\times10^{-9}$ M or less, or binds to human PD-L1 with a $K_D$ of between $1\times10^{-8}$ M and $1\times10^{-10}$ M or less.

Blockade of LAG-3 and one or more second target antigens such as CTLA-4 and/or PD-1 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-LAG-3 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-LAG-3 antibody can be administered sequentially, such as anti-CTLA-4 antibody being administered first and anti-LAG-3 antibody second, or anti-LAG-3 antibody being administered first and anti-CTLA-4 antibody second. Additionally or alternatively, an anti-PD-1 antibody and an anti-LAG-3 antibody can be administered sequentially, such as anti-PD-1 antibody being administered first and anti-LAG-3 antibody second, or anti-LAG-3 antibody being administered first and anti-PD-1 antibody second. Additionally or alternatively, an anti-PD-L1 antibody and an anti-LAG-3 antibody can be administered sequentially, such as anti-PD-L1 antibody being administered first and anti-LAG-3 antibody second, or anti-LAG-3 antibody being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-LAG-3 antibody can be concurrent, the second administration can be sequential with anti-CTLA-4 first and anti-LAG-3 second, and the third administration can be sequential with anti-LAG-3 first and anti-CTLA-4 second, etc. Additionally or alternatively, the first administration of a combination anti-PD-1 antibody and anti-LAG-3 antibody can be concurrent, the second administration can be sequential with anti-PD-1 first and anti-LAG-3 second, and the third administration can be sequential with anti-LAG-3 first and anti-PD-1 second, etc. Additionally or alternatively, the first administration of a combination anti-PD-L1 antibody and anti-LAG-3 antibody can be concurrent, the second administration can be sequential with anti-PD-L1 first and anti-LAG-3 second, and the third administration can be sequential with anti-LAG-3 first and anti-PD-L1 second, etc. Another representative dosing scheme can involve a first administration that is sequential with anti-LAG-3 first and anti-CTLA-4 (and/or anti-PD-1 and/or anti-PD-L1) second, and subsequent administrations may be concurrent.

Optionally, the combination of anti-LAG-3 and one or more additional antibodies (e.g., anti-CTLA-4 and/or anti-PD-1 and/or anti-PD-L1 antibodies) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF. A combined LAG-3 and CTLA-4 and/or PD-1 and/or PD-L1 blockade can be further combined with a vaccination protocol, such as any of the vaccination protocols discussed in detail above with respect to monotherapy with anti-LAG-3 antibodies.

A combined LAG-3 and CTLA-4 and/or PD-1 and/or PD-L1 blockade can also be further combined with standard cancer treatments. For example, a combined LAG-3 and CTLA-4 and/or PD-1 and/or PD-L1 blockade can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). An example of such a combination is a combination of anti-LAG-3 and anti-CTLA-4 antibodies and/or anti-PD-1 antibodies and/or anti-PD-L1 antibodies further in combination with decarbazine for the treatment of melanoma. Another example is a combination of anti-LAG-3 and anti-CTLA-4 antibodies and/or anti-PD-1 antibodies and/or anti-PD-L1 antibodies further in combination with interleukin-2 (IL-2) for the treatment of melanoma. The scientific rationale behind the combined use of LAG-3 and CTLA-4 and/or PD-1 and/or PD-L1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined LAG-3 and CTLA-4 and/or PD-1 and/or PD-L1 blockade through cell death include radiation, surgery, or hormone deprivation. Each of these protocols creates a source of tumor antigen in the host. Angiogenesis inhibitors can also be combined with a combined LAG-3 and CTLA-4 and/or PD-1 and/or PD-L1 blockade. Inhibition of angiogenesis leads to tumor cell death, which can be a source of tumor antigen fed into host antigen presentation pathways.

A combination of LAG-3 and CTLA-4 and/or PD-1 and/or PD-L1 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined LAG-3 and CTLA-4 and/or PD-1 and/or PD-L1 blockade. In another example, a combination of anti-LAG-3 and anti-CTLA-4 and/or antiPD-1 antibodies and/or anti-PD-L1 antibodies can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or LAG-3. In an exemplary embodiment, a treatment of a hyperproliferative disease (e.g., a cancer tumor) can include an anti-cancer antibody in combination with anti-LAG-3 and anti-CTLA-4 and/or anti-PD-1 and/or anti-PD-L1 antibodies, concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 27 4: 1363-1365). In another example, antibodies to each of these entities can be further combined with an anti-LAG-3 and anti-CTLA-4 and/or anti-PD-1 and/or anti-PD-L1 antibody combination to counteract the effects of immunosuppressive agents and favor anti-tumor immune responses by the host.

Other antibodies that can be used to activate host immune responsiveness can be further used in combination with an anti-LAG-3 and anti-CTLA-4 and/or anti-PD-land/or anti-PD-L1 antibody combination. These include molecules on the surface of dendritic cells that activate DC function and antigen presentation. Anti-CD40 antibodies (Ridge et al., supra) can be used in conjunction with an anti-LAG-3 and anti-CTLA-4 and/or anti-PD-1 and/or anti-PD-L1 combination (Ito et al., supra). Other activating antibodies to T cell co stimulatory molecules Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined LAG-3 and CTLA-4 and/or PD-1 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-LAG-3 and anti-CTLA-4 and/or anti-PD-1and/or anti-PD-L1 antibodies can be expected to increase the frequency and activity of the adoptively transferred T cells.

In certain embodiments, the present disclosure provides a method for altering an adverse event associated with treatment of a hyperproliferative disease (e.g., cancer) with an immunostimulatory agent, comprising administering an anti-LAG-3 antibody and a subtherapeutic dose of anti-CTLA-4 and/or anti-PD-1and/or anti-PD-L1 antibody to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination LAG-3 and CTLA-4 and/or PD-1 and/or PD-L1 blockade (i.e., immunostimulatory therapeutic antibodies anti-LAG-3 and antiCTLA-4 and/or anti-PD-1 antibodies and/or anti-PD-L1 antibodies) can be further combined with the use of any non-absorbable steroid. As used herein, a "nonabsorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid isbudesonide. Budesonide is a locally-acting glucocorticosteroid, which is extensivelymetabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving theileum and/or ascending colon. The usual oral dosage of ENTOCORT EC® for thetreatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58th ed. 2004; 608-610.

In still further embodiments, a combination LAG-3 and CTLA-4 and/or PD-1and/or PD-L1 blockade (i.e., immunostimulatory therapeutic antibodies anti-LAG-3 and anti-CTLA-4 and/or anti-PD-1 and/or anti-PD-L1 antibodies) in conjunction with a nonabsorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROW ASA®' Solvay).

In accordance with the methods of the present disclosure, a salicylate administered in combination with anti-LAG-3 and anti-CTLA-4 and/or anti-PD-1 and/or anti-PD-L1 antibodies and a non-absorbable steroid can include any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present disclosure encompass administering a salicylate and a non-absorbable concurrently or sequentially (e.g., a salicylate is administered 6 hours after a non-absorbable steroid), or any combination thereof. Further, according to the present disclosure, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-LAG-3 and anti-CTLA-4 and/or anti-PD-1 and/or anti-PD-L1 antibodies.

Diagnostic Methods

Over-expression of LAG-3 is observed in certain tumor samples, and patients having LAG-3-over-expressing cells are likely responsive to treatments with the anti-LAG-3 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a LAG-3 protein potentially present in the sample. Methods such as ELISA can be used, taking advantage of the anti-LAG-3 antibody, to detect the presence of the LAG-3 protein in the sample.

Presence of the LAG-3 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

The present disclosure is further illustrated by the following examples, which should not be construed as further limiting. The contents of all figures and all references, GenBank sequences, patents and published patent applications cited throughout this application are expressly incorporated herein by reference. In particular, the disclosures of PCT publications WO 09/045957, WO 09/073533, WO 09/073546, and WO 09/054863 are expressly incorporated herein by reference.

EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1

Screening of Full Human Monoclonal Antibodies Against LAG-3

Anti-LAGS human monoclonal antibodies (α-LAG-3 mAbs) were generated by screening full human Fab phage-display libraries. Wildtype LAG-3-ECD-huFc fragments can bind to Daudi cells while D1-D2 truncated LAG-3-ECD-huFc fragments fail to bind Daudi cells (FIG. 1). Consequently, the D1-D2 domains are critical for LAG-3 function.

Antigens for Phage-Display Library-Panning.

LAG-3 is a single-pass type I membrane protein which belongs to the immunoglobulin (Ig) superfamily and contains 4 extracellular Ig-like domains (ECD): domain (D)1, D2, D3 and D4. A recombinant human LAG-3-ECD-human IgG1 (LAG-3-huFc) fusion protein or a human D1-D2 truncated LAG-3-ECD-human IgG1 (ΔD1D2-LAG-3-huFc) fusion protein were expressed in a 293T cell system.

Phage Library.

Ig gene segments in mammals are arranged in groups of variable (V), diversity (D), joining (J), and constant (C) exons. The human Fab phage libraries were construed using the phage vectors, which consists of: 1) all human variable kappa (VK) repertoires; and 2) the VH of VH3-23 and VH1-69 germline genes, respectively, with genetically randomized CDR3 regions from healthy human subjects.

Antigen Screening and Generation.

To select the D1-D2 domain-specific phage binders, the phage libraries were subjected to antigen-based panning.

I) Phage Library Solution Panning Against LAG-3.

293F cells were transfected with a plasmid containing a D1-D2 deleted LAG-3 (ΔD1D2-LAG-3) sequence with a FLAG-tag at the N-terminus. At 3 days post-transfection, the ΔD1D2-LAG-3 293F cells were used for phage library screening. The phage libraries were performed the sequential negative screenings: streptavidin beads, ΔD1D2-LAG-3 transfected 293F cells and biotin-labeled-human IgG1Fc protein. The resulting library was then incubated with biotinylated LAG-3-huFc LAG-3 for 2 hrs under motion, followed by incubation with 100 µL of casein blocked streptavidin-magnetic beads for 15 min. Unbound phages were removed by washing with PBS 5-20 times. The bound phages were then eluted with freshly prepared 100 mM triethylamine (TEA) and neutralized with the addition of Tris-HCl buffer. The resulting phages were labeled as the Output-1 phage libraries. Output-1 phage libraries were subjected to the same screening as described above to generate the Output-2 and subsequent Output-3 phage libraries. Three rounds of phage library screening were performed in total.

II) Phage Library Immunotube Panning Against LAG-3.

The phage libraries were used to perform sequential negative screenings: casein-coated immunotubes, ΔD1D2-LAG-3 transfected 293F cells and human IgG1Fc protein. The resulting library was then incubated in LAG3-huFc-coated immunotubes for 2 hrs under motion. Unbound phages were removed by washing with PBST 5-20 times Similar with cell-based panning, three rounds of phage library screening were performed in total.

Output-3 phage libraries were diluted and plated to grow at 37° C. for 8 hrs and captured by anti-kappa antibody-coated filters overnight at 22° C. Biotinylated LAG-3-huFc (50 nM) and NeutrAvidin-Aβ conjugate were applied to the filter to detect antigen binding anti-LAG3 phages. Positive phage plaques were picked and eluted into 100 µL of phage elution buffer. About 10-15 µL of eluted phages were then used to infect 1 mL of XL1-Blue competent cells to make a high-titer (HT) phage for phage single point ELISA (SPE) (ELISA immobilized substrate coated with 50 nM of each protein tested). $1 \times 10^{10}$ plaque forming units (pfus) of each phage hit was used for SPE confirmation. The positive clones picked from the filter lift were then tested for LAG-3 antigen binding with LAG-3-huFc and ΔD1D2-LAG-3-huFc. The D1-D2 specific binders were amplified from antigen positive phages by PCR and sequenced. Ig light chain V genes (VL) and VH sequences were analyzed to identify unique sequences and determine sequence diversity.

VL and VH gene sequences of all hits were cloned into expression vectors pFUSE2ss-CLIg-hk (light chain, InvivoGen Cat No. pfuse2ss-hclk) and pFUSEss-CHIg-hG1 (heavy chain, InvivoGen Cat No. pfusess-hchg1). The antibodies were expressed in HEK293 cells and purified using Protein A PLUS-Agarose. Sequences of the antibodies and their CDR regions are provided in the table below.

TABLE 1

| Antibody heavy chain variable regions | | |
|---|---|---|
| Antibody No. | VH | SEQ ID NO: |
| NLAG3-HDB169-T03 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGS SWFDYWGQGTLVTVSS | 140 |
| NLAG3-HDB169-T05 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCASSY HGGGYHRYWGQGTLVTVSS | 141 |

TABLE 1 -continued

Antibody heavy chain variable regions

| Antibody No. | VH | SEQ ID NO: |
|---|---|---|
| NLAG3-HDB169-T06 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTTSK YSGSALRYWGQGTLVTVSS | 142 |
| NLAG3-HDB169-T07 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDR TGAFDYWGQGTLVTVSS | 143 |
| NLAG3-HDB169-T08 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARHE TVAGSFDYWGQGTLVTVSS | 144 |
| NLAG3-HDB169-T10 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARTG YYGGNSGAFDIWGQGTMVTVSS | 145 |
| NLAG3-HDB169-T13 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARAG TGMDLVFNSWGQGTLVTVSS | 146 |
| NLAG3-HDB169-T23 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGL ARGDLNFGYWGQGTLVTVSS | 147 |
| NLAG3-HDB169-S24 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTREP HFDYWGQGTLVTVSS | 148 |
| NLAG3-HDB169-S27 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTTAA PGSYYLVFHYWGQGTLVTVSS | 149 |
| NLAG3-HDB169-S31 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDA GPVGYYGMDVWGQGTTVTVSS | 150 |
| NLAG3-HDB169-S32 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAGDG LYGSGSFGYWGQGTPVTVSS | 151 |
| NLAG3-HDB169-S61 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAKDI RWFYGMDVWGQGTTVTVSSw | 152 |
| NLAG3-HDB169-S64 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARHE SGIAGGHFDYWGQGTLVTVSS | 153 |
| NLAG3-HDB169-S86 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDA GPVGYYGMDVWGQGTTVTVS | 154 |
| NLAG3-HDB169-S87 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAKDI RWYYGMDVWGQGTTVTVSS | 155 |
| NLAG3-HDB169-T94 | QVQLVQSGAEVKKPGSSVKVECKASGGTFSSYAISWVRQAPGQGLEWMGG IIPIFGTANYAQKFQGRVTITADESTSTAYMELSSLRSEDTAVYYCAKGV RGTYQIGYYGMDVWGQGTTVTVSS | 156 |
| NLAG3-HDB169-T97 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARQG TAMALDYWGQGTLVTVSS | 157 |
| NLAG3-HDB169-T99 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCVRDL QDWNYGGAAYWGQGTLVTVSS | 158 |
| NLAG3-HDB169-S103 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDD YYYGQFDSWGQGTLVTVSS | 159 |

TABLE 1 -continued

Antibody heavy chain variable regions

| Antibody No. | VH | SEQ ID NO: |
|---|---|---|
| NLAG3-HDB169-S107 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAREI TGTSYTALDSWGQGTLVTVSS | 160 |
| NLAG3-HDB169-S109 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGH IDGQAAGDYWGQGTLVTVSS | 161 |
| NLAG3-HDB169-S119 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRVPNPPYWGQGTLVTVSS | 162 |
| NLAG3-HDB169-S120 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARSG DRYDFWSGYWGQGTLVTVSS | 163 |
| NLAG3-HDB169-S127 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRVPNPPYWGQGTLVTVSS | 164 |
| NLAG3-HDB169-S128 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDA GPVGYYGMDVWGQGTMVTVSS | 165 |
| NLAG3-HDB169-S136 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTRGQ DSTWYSSFDYWGQGTLVTVSS | 166 |
| NLAG3-HDB169-S139 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRLPNPPYWGQGTLVTVSS | 167 |
| NLAG3-HDB169-S150 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCATTQ TSFYSHGMDVWGQGTTVTVSS | 168 |
| NLAG3-HDB169-S157 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRKT PFWGALDSWGRGTLVTVSS | 169 |
| NLAG3-HDB169-S164 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGF TYGDFIFDYWGQGTLVTVSS | 170 |
| NLAG3-HDB169-S177 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDV RGVTYLGMDVWGQGTTVTVSS | 171 |
| NLAG3-HDB323-S20 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRKT PFWGTLDSWGRGTLVTVSS | 172 |
| NLAG3-HDB323-S21 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRRT PFWGALDSWGRGTLVTVSS | 173 |
| NLAG3-HDB323-S32 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRKT PFWGALDSWGRGTLVTVSS | 174 |
| NLAG3-HDB323-S35 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCAKRKGL GSPTDYYYGMDVWGQGTTVTVSS | 175 |
| NLAG3-HDB323-S52 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRKT PFWGALDSWGRGTLVTVSS | 176 |
| NLAG3-HDB323-S55 | QLLESGGGLVQPGGSLRLSCAASGFTFSSYAMSWVRQAPGKGLEWVSAIS GSGGSTYYADSVKGRFTISRDNSKNTLYLQMNSLRAEDTAVYYCARVRKT PFWGTLDSWGRGSLVTVSS | 177 |

TABLE 1 -continued

Antibody heavy chain variable regions

| Antibody No. | VH | SEQ ID NO: |
|---|---|---|
| NLAG3-HDB323-T89 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCVRPEYDTYYYGMDVWGQGTTVTVSS | 178 |
| NLAG3-HDB323-T92 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGGGSYDYWGQGTLVTVSS | 179 |
| NLAG3-HDB323-T94 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARALNGMDVWGQGTMVTVSS | 180 |
| NLAG3-HDB323-S102 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCTRPLQGIAAADSYYYYAMDVWGQGTTVTVSS | 181 |
| NLAG3-HDB323-S103 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLHSYLSEEFDPWGQGTLVTVSS | 182 |
| NLAG3-HDB323-S107 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGALDSWGRGTLVTVSS | 183 |
| NLAG3-HDB323-S114 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKLSAVNTYIDDWGQGTLVTVSS | 184 |
| NLAG3-HDB323-S135 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVTKTPFWGTLDYWGQGTLVTVSS | 185 |
| NLAG3-HDB323-S143 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRRTPFWGALDSWGRGTLVTVSS | 186 |
| NLAG3-HDB323-S146 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVSQSPVWGYFDYWGQGMLVTVSS | 187 |
| NLAG3-HDB323-S161 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDGYYDFWSGYSDYWGQGTLVTVSS | 188 |

TABLE 2

Heavy chain CDRs

| Antibody No. | CDR H1 | SEQ ID NO: | CDR H2 | SEQ ID NO: | CDR H3 | SEQ ID NO: |
|---|---|---|---|---|---|---|
| NLAG3-HDB169-T03 | SYAIS | 1 | GIIPIFGTANYAQKFQG | 3 | ARGSSWFDY | 5 |
| NLAG3-HDB169-T05 | SYAIS | 1 | GIIPIFGTANYAQKFQG | 3 | ASSYHGGGYHRY | 6 |
| NLAG3-HDB169-T06 | SYAIS | 1 | GIIPIFGTANYAQKFQG | 3 | TTSKYSGSALRY | 7 |
| NLAG3-HDB169-T07 | SYAIS | 1 | GIIPIFGTANYAQKFQG | 3 | ARDRTGAFDY | 8 |
| NLAG3-HDB169-T08 | SYAIS | 1 | GIIPIFGTANYAQKFQG | 3 | ARHETVAGSFDY | 9 |
| NLAG3-HDB169-T10 | SYAIS | 1 | GIIPIFGTANYAQKFQG | 3 | ARTGYYGGNSGAFDI | 10 |
| NLAG3-HDB169-T13 | SYAIS | 1 | GIIPIFGTANYAQKFQG | 3 | ARAGTGMDLVFNS | 11 |
| NLAG3-HDB169-T23 | SYAIS | 1 | GIIPIFGTANYAQKFQG | 3 | ARGLARGDLNFGY | 12 |
| NLAG3-HDB169-S24 | SYAIS | 1 | GIIPIFGTANYAQKFQG | 3 | TREPHFDY | 13 |
| NLAG3-HDB169-S27 | SYAIS | 1 | GIIPIFGTANYAQKFQG | 3 | TTAAPGSYYLVFHY | 14 |

TABLE 2-continued

Heavy chain CDRs

| Antibody No. | CDR H1 | SEQ ID NO: | CDR H2 | SEQ ID NO: | CDR H3 | SEQ ID NO: |
|---|---|---|---|---|---|---|
| NLAG3-HDB169-S31 | SYAIS | 1 | GIIPIFGTANYAQKFQG | 3 | ARDAGPVGYYGMDV | 15 |
| NLAG3-HDB169-S32 | SYAIS | 1 | GIIPIFGTANYAQKFQG | 3 | AGDGLYGSGSFGY | 16 |
| NLAG3-HDB169-S61 | SYAIS | 1 | GIIPIFGTANYAQKFQG | 3 | AKDIRWFYGMDV | 17 |
| NLAG3-HDB169-S64 | SYAIS | 1 | GIIPIFGTANYAQKFQG | 3 | ARHESGIAGGHFDY | 18 |
| NLAG3-HDB169-S86 | SYAIS | 1 | GIIPIFGTANYAQKFQG | 3 | ARDAGPVGYYGMDV | 15 |
| NLAG3-HDB169-S87 | SYAIS | 1 | GIIPIFGTANYAQKFQG | 3 | AKDIRWYYGMDV | 19 |
| NLAG3-HDB169-T94 | SYAIS | 1 | GIIPIFGTANYAQKFQG | 3 | AKGVRGTYQIGYYGMDV | 20 |
| NLAG3-HDB169-T97 | SYAIS | 1 | GIIPIFGTANYAQKFQG | 3 | ARQGTAMALDY | 21 |
| NLAG3-HDB169-T99 | SYAIS | 1 | GIIPIFGTANYAQKFQG | 3 | VRDLQDWNYGGAAY | 22 |
| NLAG3-HDB169-S103 | SYAIS | 1 | GIIPIFGTANYAQKFQG | 3 | ARDDYYYGQFDS | 23 |
| NLAG3-HDB169-S107 | SYAIS | 1 | GIIPIFGTANYAQKFQG | 3 | AREITGTSYTALDS | 24 |
| NLAG3-HDB169-S109 | SYAIS | 1 | GIIPIFGTANYAQKFQG | 3 | ARGHIDGQAAGDY | 25 |
| NLAG3-HDB169-S119 | SYAIS | 1 | GIIPIFGTANYAQKFQG | 3 | AASTLRVPNPPY | 26 |
| NLAG3-HDB169-S120 | SYAIS | 1 | GIIPIFGTANYAQKFQG | 3 | ARSGDRYDFWSGY | 27 |
| NLAG3-HDB169-S127 | SYAIS | 1 | GIIPIFGTANYAQKFQG | 3 | AASTLRVPNPPY | 26 |
| NLAG3-HDB169-S128 | SYAIS | 1 | GIIPIFGTANYAQKFQG | 3 | ARDAGPVGYYGMDV | 15 |
| NLAG3-HDB169-S136 | SYAIS | 1 | GIIPIFGTANYAQKFQG | 3 | TRGQDSTWYSSFDY | 28 |
| NLAG3-HDB169-S139 | SYAIS | 1 | GIIPIFGTANYAQKFQG | 3 | AASTLRLPNPPY | 29 |
| NLAG3-HDB169-S150 | SYAIS | 1 | GIIPIFGTANYAQKFQG | 3 | ATTQTSFYSHGMDV | 30 |
| NLAG3-HDB169-S157 | SYAIS | 1 | GIIPIFGTANYAQKFQG | 3 | ARVRKTPFWGALDS | 31 |
| NLAG3-HDB169-S164 | SYAIS | 1 | GIIPIFGTANYAQKFQG | 3 | ARGFTYGDFIFDY | 32 |
| NLAG3-HDB169-S177 | SYAIS | 1 | GIIPIFGTANYAQKFQG | 3 | ARDVRGVTYLGMDV | 33 |
| NLAG3-HDB323-S20 | SYAMS | 2 | AISGSGGSTYYADSVKG | 4 | ARVRKTPFWGTLDS | 34 |
| NLAG3-HDB323-S21 | SYAMS | 2 | AISGSGGSTYYADSVKG | 4 | ARVRRTPFWGALDS | 35 |
| NLAG3-HDB323-S32 | SYAMS | 2 | AISGSGGSTYYADSVKG | 4 | ARVRKTPFWGALDS | 31 |
| NLAG3-HDB323-S35 | SYAMS | 2 | AISGSGGSTYYADSVKG | 4 | AKRKGLGSPTDYYYGMDV | 36 |
| NLAG3-HDB323-S52 | SYAMS | 2 | AISGSGGSTYYADSVKG | 4 | ARVRKTPFWGALDS | 31 |
| NLAG3-HDB323-S55 | SYAMS | 2 | AISGSGGSTYYADSVKG | 4 | ARVRKTPFWGTLDS | 34 |
| NLAG3-HDB323-T89 | SYAMS | 2 | AISGSGGSTYYADSVKG | 4 | VRPEYDTYYYGMDV | 37 |
| NLAG3-HDB323-T92 | SYAMS | 2 | AISGSGGSTYYADSVKG | 4 | AKGGGSYDY | 38 |
| NLAG3-HDB323-T94 | SYAMS | 2 | AISGSGGSTYYADSVKG | 4 | ARALNGMDV | 39 |
| NLAG3-HDB323-S102 | SYAMS | 2 | AISGSGGSTYYADSVKG | 4 | TRPLQGIAAADSYYYYAMDV | 40 |
| NLAG3-HDB323-S103 | SYAMS | 2 | AISGSGGSTYYADSVKG | 4 | ARLHSYLSEEFDP | 41 |
| NLAG3-HDB323-S107 | SYAMS | 2 | AISGSGGSTYYADSVKG | 4 | ARVRKTPFWGALDS | 31 |
| NLAG3-HDB323-S114 | SYAMS | 2 | AISGSGGSTYYADSVKG | 4 | AKLSAVNTYIDD | 42 |
| NLAG3-HDB323-S135 | SYAMS | 2 | AISGSGGSTYYADSVKG | 4 | ARVTKTPFWGTLDY | 43 |
| NLAG3-HDB323-S143 | SYAMS | 2 | AISGSGGSTYYADSVKG | 4 | ARVRRTPFWGALDS | 35 |

TABLE 2-continued

Heavy chain CDRs

| Antibody No. | CDR H1 | SEQ ID NO: | CDR H2 | SEQ ID NO: | CDR H3 | SEQ ID NO: |
|---|---|---|---|---|---|---|
| NLAG3-HDB323-S146 | SYAMS | 2 | AISGSGGSTYYADSVKG | 4 | ARVSQSPVWGYFDY | 44 |
| NLAG3-HDB323-S161 | SYAMS | 2 | AISGSGGSTYYADSVKG | 4 | AKDGYYDFWSGYSDY | 45 |

TABLE 3

Light chain variable regions

| Antibody No. | VL | SEQ ID NO: |
|---|---|---|
| NLAG3-HDB169-T03 | DIQLTQSPSSLSAFVGDRVTITCQANQDIHHYLNWYQQKPGKAPKLLIYDASILQSGVPSRFSGSGSGTDFTLTISSLQPEDFATYFCQQADSFPITFGQGTRLEIKR | 189 |
| NLAG3-HDB169-T05 | EIVLTQSPDSLAVSLGERATINCKSSQSVLYSSSNKNYLAWYQQKPGQPPKLLIYWASTRESGVPDRFSGSGSGTDFTLTISSLQPEDFATYYCQQSYSTPWTFGPGTKLEIKR | 190 |
| NLAG3-HDB169-T06 | DIQMTQSPDSLAVSLGERATINCKSSQSVLYSSNNKNYLAWYQQKPGHPPKLLVYWASTRESGVPARFSASGSGTDFTLAISNLQAEDVAVYYCQQYYSTPWTFGQGTKVEIKR | 191 |
| NLAG3-HDB169-T07 | EIVLTQSPLSLPVTPGEPASISCRSSQNLLHSDGYNYLNWYLQKPGQSPQLLIYLGSNRATGVPDRFSGSGSGTDFTLTISSLQPEDFATYYCQQSYSTPWTFGQGTKVEIKR | 192 |
| NLAG3-HDB169-T08 | DIVMTQSPDSLAVSLGERATINCKSSQSVLYTSNNKNYLAWYQQKPGQPPKLLIYWASTRESGVPDRFSGSGSGTDFTLTISSLQAEDVAIYYCQQYYSTPWTFGQGTKLEIKR | 193 |
| NLAG3-HDB169-T10 | AIQLTQSPDSLAVSLGERATINCKSSQSVLYSSNNKNYLAWYQQKPGQPPKLLIYWASTRESGVPDRFSGSGSGTDFTLTISSLQAEDSATYYCQQSFTTPWTFGQGTKVEIKR | 194 |
| NLAG3-HDB169-T13 | DIQMTQSPSSLSASVGDRVTITCQASQDINRYLSWYQQKPGKAPKLLIYDASNLETGVPSRFSGSASGTDFTFAISSLQPEDIATYYCQQYDNLPPTFGQGTRLEIKR | 195 |
| NLAG3-HDB169-T23 | EIVMTQSPSSLSASVGDRVTITCQASQDISNYLNWYQQKPGKAPKLLIYAASSLQSGVPSRFSGSGSGTDFTLTISSLQPEDFASYYCQQSYGSPVTFGQGTKLEIKR | 196 |
| NLAG3-HDB169-S24 | EIVMTQSPSSLSASVGDRVTITCQASQDISNYLNWYQQKPGKAPKLLIYDASNLETGVPSRFSGSGSGTEFTLTISSLRPEDFATYFCQQADSFPITFGQGTRLEIKR | 197 |
| NLAG3-HDB169-S27 | DIQLTQSPSSLSASVGDRVTITCRASQTISSHLNWYQQKPGKAPKVLIYAASSLQSGVPSRFSGSGSGTEFTLTISSLQPDDFATYYCQQGNSFPFTFGPGTKVEIKR | 198 |
| NLAG3-HDB169-S31 | AIRMTQSPSTLSASVGDRVTITCRASQGIAGWLAWYQQKPGKAPKLLIYAASSLQSGVPSRFSGSASGTDFTLTISNLQPEDFATYYCQQAKSFPLTFGGGTKVEIKR | 199 |
| NLAG3-HDB169-S32 | DIVMTQSPDSLAVSLGERATINCKSSQSVLYSSNNKNYLAWYQQKPGQPPKLLIYWASTRESGVPDRFSGTGSGTDFTLTISSLQAEDVAVYYCQQSYSTPWTFGQGTKLEIK | 200 |
| NLAG3-HDB169-S61 | DIVMTQSPSSVSAFVGDRVTITCRASQGVSSWLAWFQQKPGKAPKLLIYAASTLQSGVPSRFSGRGYGTEFTLTISSLQPEDLATYYCQQVKSFPLTFGGGTKVDIKR | 201 |
| NLAG3-HDB169-S64 | DIVMTQSPDSLAVSLGERATINCKSSQSLFYHSNNHNYLAWYQQKPGQPPKLLIYWASTRQSGVPDRFTGSGSGTDFTLTISSLQAEDVAVYYCQQYYNTPWTFGQGTKVEIKR | 202 |
| NLAG3-HDB169-S86 | AIRMTQSPSTLSASVGDRVTITCRASQGIAGWLAWYQQKPGKAPKLLIYAASSLQSGVPSRFSGSASGTDFTLTISNLQPEDFATYYCQQAKSFPLTFGGGTKVEIKR | 203 |

TABLE 3-continued

Light chain variable regions

| Antibody No. | VL | SEQ ID NO: |
|---|---|---|
| NLAG3-HDB169-S87 | DIVMTQSPSSVSAFVGDRVTITCRASQGVSSWLAWFQQKPGKAPKLLIYA ASTLQSGVPSRFSGRGYGTEFTLTISSLQPEDLATYYCQQVKSFPLTFGG GTKVDIKR | 204 |
| NLAG3-HDB169-T94 | DIVMTQSPSSLSASVGDRVTITCRASQGISSSLAWYQQKPGKAPNLLIYT ASTLQNGVPSRFSGSGSTDFTLTISGLQPEDFATYYCQQTKNFPLTFGG GTRLEIKR | 205 |
| NLAG3-HDB169-T97 | EIVLTQSPDSLAVSLGERATINCKSSQSVLYSSNNKNYLAWYQQRPGQPP KLLISWASTRESGVPDRFSGSGSGADFSLTISSLQAEDVAVYYCQQYYST PWTFGQGTKLEIKR | 206 |
| NLAG3-HDB169-T99 | VIWMTQSPSSLSASVGDSVTITCQASRDISNSLSWHQQKPGKAPKLLIYA ASSLQSGVPSRFSGSGSGTDFTLTISSLQPEDFATYYCQQTKSFPLTFGG GTKVEIKR | 207 |
| NLAG3-HDB169-S103 | EIVMTQSPSSLSASVGDRVTISCRASQSISRYLNWYQQKPGQAPKLLIYA AFSLQSGVPSRFSGSGSGTDFTLTISSLQPEDFATYYCQQSYNTPRTFGQ GTKLEIKR | 208 |
| NLAG3-HDB169-S107 | DVVMTQSPSTVSASVGDRITITCRASRSISNWLAWYQQKPGKAPKLLIYA ASSLQSGVPSRFSGSGSGTDFTLTISSLQPEDFATYYCQQAKSFPLTFGG GTKVEIK | 209 |
| NLAG3-HDB169-S109 | DIQLTQSPDSLAVSLGERATINCKSSQSVFYRSNQKNYLAWYQQKPGQTP RLLIYGASSRATGIPDRFSGSGSGTDFTLTISSLQPEDFATYYCQQSYRA PWTFGQGTKVEIKR | 210 |
| NLAG3-HDB169-S119 | EIVLTQSPGTLSLSPGERATLSCRASQSVSSYLAWYQQKPGQAPRLLIYG ISSRATGIPDRFSGSGSGTDFTLTISSLQPEDFATYYCQQANNFPLTFGG GTKLEIKR | 211 |
| NLAG3-HDB169-S120 | EIVLTQSPSSVSASVGDRVTITCRASRGISSWLAWYQQKPGKAPKLLIYA ASTLQSGVPSRFSGSGSGTDFTLTISSLQPEDFATYYCQQAKSFPLTFGG GTKVEIKR | 212 |
| NLAG3-HDB169-S127 | EIVLTQSPGTLSLSPGERATLSCRASQSVSSYLAWYQQKPGQAPRLLIYG ISSRATGIPDRFSGSGSGTDFTLTISSLQPEDFATYYCQQANNFPLTFGG GTKLEIKR | 213 |
| NLAG3-HDB169-S128 | AIQMTQSPSSLSASVGDRVTITCRASQGISSWLAWYQQKPGKAPKLLIYA ASSLQSGVPSRFSGSGSGTDFTLTISRLQPEDFATYYCQQAKSFPLTFGG GTKVEIKR | 214 |
| NLAG3-HDB169-S136 | AIRMTQSPSSLSASVGDRVTITCRASQSISSYLNWYQQKPGKAPNLLIYA VSTLQSGVPSRFSGSGSGTVFTLTISSLQPEDFATYFCQQGNSFPLTFGG GTKVEIKR | 215 |
| NLAG3-HDB169-S139 | DIQLTQSPSTLSASVGDRVTITCRASQAISNLLAWYQQKPGKPPNLLIYD ISTLQNGVPSRFSGSGSGTDFTLTINSLQPEDFAIYYCQQSKNFPVTFGG GTKVEIKR | 216 |
| NLAG3-HDB169-S150 | DIQLTQSPSSVSASVGDRVTITCRASQGISSWLAWYQQKPGKAPKLLIYG ASTLQSGVPSRFSGSGSGADYTLTISSLQPEDFATYYCQQANSFPLTFAG GTKLEIKR | 217 |
| NLAG3-HDB169-S157 | DIQLTQSPSSLSASPGDRVTITCRASQGISTWLAWYQQKPGNAPKLLIYA ASSLQSGVPSRFSGSKSGTEYTLTISSLQPEDFATYYCQQLESYPLTFGG GTKVEIKR | 218 |
| NLAG3-HDB169-S164 | AIRMTQSPDSLVVSLGERATINCKSSQSVLYSSNNKNYLAWYQQKPGQPP KLLIYWASTRESGVPDRFSGSGSGTDFTLSISSLQAEDVAVYYCQQYYSS PTFGGGTKVEIKR | 219 |
| NLAG3-HDB169-S177 | DVVMTQSPFFLSASVGDRVTITCRASQGIASNLAWYQQKPGKAPKLLIYA ASTLQSGVPSRFTGSGSGTEFTLTVTSLQPEDFATYYCQQLKTFPLTFGG GTKVEIKR | 220 |
| NLAG3-HDB323-S20 | VIWMTQSPSSLSASVGDRVTITCRASQGVSSYLAWYQQKPGKAPKLLIYA ASSLQSGVPSRFSGSGSGTEFTLTISSLQPEDFATYYCQQTNWFPLTFGP GTRLEIKR | 221 |
| NLAG3-HDB323-S21 | DIQMTQSPSSLSTSAGDTVTITCRASQSIYTYLNWYQQKPGKAPNLLIYG ASSLQSGVPSRFSGSGSGTDFTLTISSLQPEDFATYYCQQAQSFPITFGQ GTRLEIKR | 222 |

TABLE 3-continued

Light chain variable regions

| Antibody No. | VL | SEQ ID NO: |
|---|---|---|
| NLAG3-HDB323-S32 | VIWMTQSPSSVSASVGDRVTITCRASQGISSWLAWYQQKPGKAPKLLIYA ASSLQSGVPSRFSGSGSGTDFTLTISSLQPEDFATYYCQQAHSFPLTFGG GTKVEIKR | 223 |
| NLAG3-HDB323-S35 | AIQLTQSPSTLSASVGDRVTITCRASQFVSDWLAWYQQKPGKAPKLLIYA ASTLQSGVPSRFSGSGSGTDFTLTISSLQPEDLATYYCLQDYHFPLTFGG GTKLEIKR | 224 |
| NLAG3-HDB323-S52 | DVVMTQSPSSVSASVGDRVTITCRASQDIVNWLAWYQQKPGKAPKLLIYA ASTLESGAPSRFSASGSGTDFTLTISSLQPDDFATYYCQQGHSFPLTFGP GTKLEIKR | 225 |
| NLAG3-HDB323-S55 | DIVMTQSPSSLSASVGDRVTITCRASQSIYTYLNWYQQKPGKAPKLLIYD ASSLQSGVPSRFSGSGYGTEFTLTISGLQPEDFATYYCQQSYIFPLTFGR GTKVEIKR | 226 |
| NLAG3-HDB323-T89 | AIRMTQSPSFVSASVGDRVTIACRASQTISTWLAWYQQKPGKAPKVLISK ASNLQSGVPSRFSGSGSGTEFTLTISSLQPDDFATYYCQQYDTYWTFGQG TKVEIKR | 227 |
| NLAG3-HDB323-T92 | AIRMTQSPSFVSASVGDRVTIACRASQTISTWLAWYQQKPGKAPKVLISK ASNLQSGVPSRFSGSGSGTEFTLTISSLQPDDFATYYCQQYDTYWTFGQG TKVEIKR | 228 |
| NLAG3-HDB323-T94 | DIVMTQSPSFVSASVGDTVTITCRASQGISSYLAWYQQKPGKAPKLLIYA ASTLQSGVPSRFSGSGSGTEFTLTISSLQPEDFATYYCQQLNSYPLFTFG PGTKVEIKR | 229 |
| NLAG3-HDB323-S102 | DIQMTQSPSTLSASVGDRVTITCRASQSIGYWLAWYQQKPGKAPKLLIYR ASSLQSGVPSRFSGSGSATEFTLTITSLQPDDFATYFCQQYSSYWTFGQG TKVEIKR | 230 |
| NLAG3-HDB323-S103 | EIVLTQSPSSLSASVGDTVTITCRATQSISSWLAWYQQKPGKAPQRLISG ASTLQSGVPSRFSGSGSGTEFTLTISGLQPEDFATYYCLQHNTYPFTFGQ GTKVEIKR | 231 |
| NLAG3-HDB323-S107 | DIVMTQSPSSVSASVGDRVTITCRASQGVRNWLAWYQQKPGKAPKLLIYA ASHLQSGVPSRFSGSGSGTDFTLTISSLQTDDFATYYCQQGHSFPLTFGG GTKVEIKR | 232 |
| NLAG3-HDB323-S114 | DIVMTQSPSSVSASVGDRVTITCRASQGVRNWLAWYQQKPGKAPKLLIYA ASHLQSGVPSRFSGSGSGTDFTLTISSLQTDDFATYYCQQGHSFPLTFGG GTKVEIKR | 233 |
| NLAG3-HDB323-S135 | VIWMTQSPSTLSASVGDRVTITCRASQSINNYLAWYQQKPGKAPKLLIYD ASTLQSGVPSRFSGGGSGTDFTLTINSLQPDDFASYYCQQAHSFPFTFGG GTKLEIKR | 234 |
| NLAG3-HDB323-S143 | EIVMTQSPSSVSASVGDRVTITCRASQDITSWLAWYQQKPGKAPKLLIYA ASTLESGVPSRFSGSGSGTDFTLTITGLQPEDFATYYCQQANMFPLTFGG GTKVEIKR | 235 |
| NLAG3-HDB323-S146 | AIRMTQSPSSLSASVGDRVTITCRASQGIYDYLAWYQQKPGKAPSLLIYA ASNLERGVPSRFSGSGSGKYFILTISSLQPEDFATYYCQQANSFPLTFGG GTKVEIKR | 236 |
| NLAG3-HDB323-S161 | AIQLTQSPSSLSASVGDRVTITCRASEGISGWLAWYQQIPGKAPKLLIYA ASSLETGVPSRFSGSGYGTDFTLTISSLQPEDFATYYCQQADSFPFTFGP GTKVEIKR | 237 |

TABLE 4

Light chain variable regions

| Antibody No. | CDR L1 | SEQ ID NO: | CDR L2 | SEQ ID NO: | CDR L3 | SEQ ID NO: |
|---|---|---|---|---|---|---|
| NLAG3-HDB169-T03 | QANQDIHHYLN | 46 | DASILQS | 81 | QQADSFPIT | 104 |
| NLAG3-HDB169-T05 | KSSQSVLYSSSNKNYLA | 47 | WASTRES | 82 | QQSYSTPWT | 105 |
| NLAG3-HDB169-T06 | KSSQSVLYSSNNKNYLA | 48 | WASTRES | 82 | QQYYSTPWT | 106 |

TABLE 4-continued

Light chain variable regions

| Antibody No. | CDR L1 | SEQ ID NO: | CDR L2 | SEQ ID NO: | CDR L3 | SEQ ID NO: |
|---|---|---|---|---|---|---|
| NLAG3-HDB169-T07 | RSSQNLLHSDGYNYLN | 49 | LGSNRAT | 83 | QQSYSTPWT | 105 |
| NLAG3-HDB169-T08 | KSSQSVLYTSNNKNYLA | 50 | WASTRES | 82 | QQYYSTPWT | 106 |
| NLAG3-HDB169-T10 | KSSQSVLYSSNNKNYLA | 48 | WASTRES | 82 | QQSFTTPWT | 107 |
| NLAG3-HDB169-T13 | QASQDINRYLS | 51 | DASNLET | 84 | QQYDNLPPT | 108 |
| NLAG3-HDB169-T23 | QASQDISNYLN | 52 | AASSLQS | 85 | QQSYGSPVT | 109 |
| NLAG3-HDB169-S24 | QASQDISNYLN | 52 | DASNLET | 84 | QQADSFPIT | 104 |
| NLAG3-HDB169-S27 | RASQTISSHLN | 53 | AASSLQS | 85 | QQGNSFPFT | 110 |
| NLAG3-HDB169-S31 | RASQGIAGWLA | 54 | AASSLQS | 85 | QQAKSFPLT | 111 |
| NLAG3-HDB169-S32 | KSSQSVLYSSNNKNYLA | 48 | WASTRES | 82 | QQSYSTPWT | 105 |
| NLAG3-HDB169-S61 | RASQGVSSWLA | 55 | AASTLQS | 86 | QQVKSFPLT | 112 |
| NLAG3-HDB169-S64 | KSSQSLFYHSNNHNYLA | 56 | WASTRQS | 87 | QQYYNTPWT | 113 |
| NLAG3-HDB169-S86 | RASQGIAGWLA | 54 | AASSLQS | 85 | QQAKSFPLT | 111 |
| NLAG3-HDB169-S87 | RASQGVSSWLA | 55 | AASTLQS | 86 | QQVKSFPLT | 112 |
| NLAG3-HDB169-T94 | RASQGISSSLA | 57 | TASTLQN | 98 | QQTKNFPLT | 114 |
| NLAG3-HDB169-T97 | KSSQSVLYSSNNKNYLA | 48 | WASTRES | 82 | QQYYSTPWT | 106 |
| NLAG3-HDB169-T99 | QASRDISNSLS | 58 | AASSLQS | 85 | QQTKSFPLT | 116 |
| NLAG3-HDB169-S103 | RASQSISRYLN | 59 | AAFSLQS | 88 | QQSYNTPRT | 117 |
| NLAG3-HDB169-S107 | RASRSISNWLA | 60 | AASSLQS | 85 | QQAKSFPLT | 111 |
| NLAG3-HDB169-S109 | KSSQSVFYRSNQKNYLA | 61 | GASSRAT | 89 | QQSYRAPWT | 118 |
| NLAG3-HDB169-S119 | RASQSVSSYLA | 62 | GISSRAT | 90 | QQANNFPLT | 119 |
| NLAG3-HDB169-S120 | RASRGISSWLA | 63 | AASTLQS | 86 | QQAKSFPLT | 111 |
| NLAG3-HDB169-S127 | RASQSVSSYLA | 62 | GISSRAT | 90 | QQANNFPLT | 119 |
| NLAG3-HDB169-S128 | RASQGISSWLA | 64 | AASSLQS | 85 | QQAKSFPLT | 111 |
| NLAG3-HDB169-S136 | RASQSISSYLN | 65 | AVSTLQS | 91 | QQGNSFPLT | 120 |
| NLAG3-HDB169-S139 | RASQAISNLLA | 66 | DISTLQN | 92 | QQSKNFPVT | 121 |
| NLAG3-HDB169-S150 | RASQGISSWLA | 64 | GASTLQS | 93 | QQANSFPLT | 122 |
| NLAG3-HDB169-S157 | RASQGISTWLA | 67 | AASSLQS | 85 | QQLESYPLT | 123 |
| NLAG3-HDB169-S164 | KSSQSVLYSSNNKNYLA | 48 | WASTRES | 82 | QQYYSSPT | 124 |
| NLAG3-HDB169-S177 | RASQGIASNLA | 68 | AASTLQS | 86 | QQLKTFPLT | 125 |
| NLAG3-HDB323-S20 | RASQGVSSYLA | 69 | AASSLQS | 85 | QQTNWFPLT | 126 |
| NLAG3-HDB323-S21 | RASQSIYTYLN | 70 | GASSLQS | 94 | QQAQSFPIT | 127 |
| NLAG3-HDB323-S32 | RASQGISSWLA | 64 | AASSLQS | 85 | QQAHSFPLT | 128 |
| NLAG3-HDB323-S35 | RASQFVSDWLA | 71 | AASTLQS | 86 | LQDYHFPLT | 129 |
| NLAG3-HDB323-S52 | RASQDIVNWLA | 115 | AASTLES | 95 | QQGHSFPLT | 130 |
| NLAG3-HDB323-S55 | RASQSIYTYLN | 70 | DASSLQS | 96 | QQSYIFPLT | 131 |
| NLAG3-HDB323-T89 | RASQTISTWLA | 72 | KASNLQS | 97 | QQYDTYWT | 132 |
| NLAG3-HDB323-T92 | RASQTISTWLA | 72 | KASNLQS | 97 | QQYDTYWT | 132 |

TABLE 4-continued

Light chain variable regions

| Antibody No. | CDR L1 | SEQ ID NO: | CDR L2 | SEQ ID NO: | CDR L3 | SEQ ID NO: |
|---|---|---|---|---|---|---|
| NLAG3-HDB323-T94 | RASQGISSYLA | 73 | AASTLQS | 86 | QQLNSYPLFT | 133 |
| NLAG3-HDB323-S102 | RASQSIGYWLA | 74 | RASSLQS | 99 | QQYSSYWT | 134 |
| NLAG3-HDB323-S103 | RATQSISSWLA | 75 | GASTLQS | 93 | LQHNTYPFT | 135 |
| NLAG3-HDB323-S107 | RASQGVRNWLA | 76 | AASHLQS | 100 | QQGHSFPLT | 130 |
| NLAG3-HDB323-S114 | RASQGVRNWLA | 76 | AASHLQS | 100 | QQGHSFPLT | 136 |
| NLAG3-HDB323-S135 | RASQSINNYLA | 77 | DASTLQS | 101 | QQAHSFPFT | 137 |
| NLAG3-HDB323-S143 | RASQDITSWLA | 78 | AASTLES | 95 | QQANMFPLT | 138 |
| NLAG3-HDB323-S146 | RASQGIYDYLA | 79 | AASNLER | 102 | QQANSFPLT | 122 |
| NLAG3-HDB323-S161 | RAsEGISGWLA | 80 | AASSLET | 103 | QQADSFPFT | 139 |

Example 2

Figure 2:
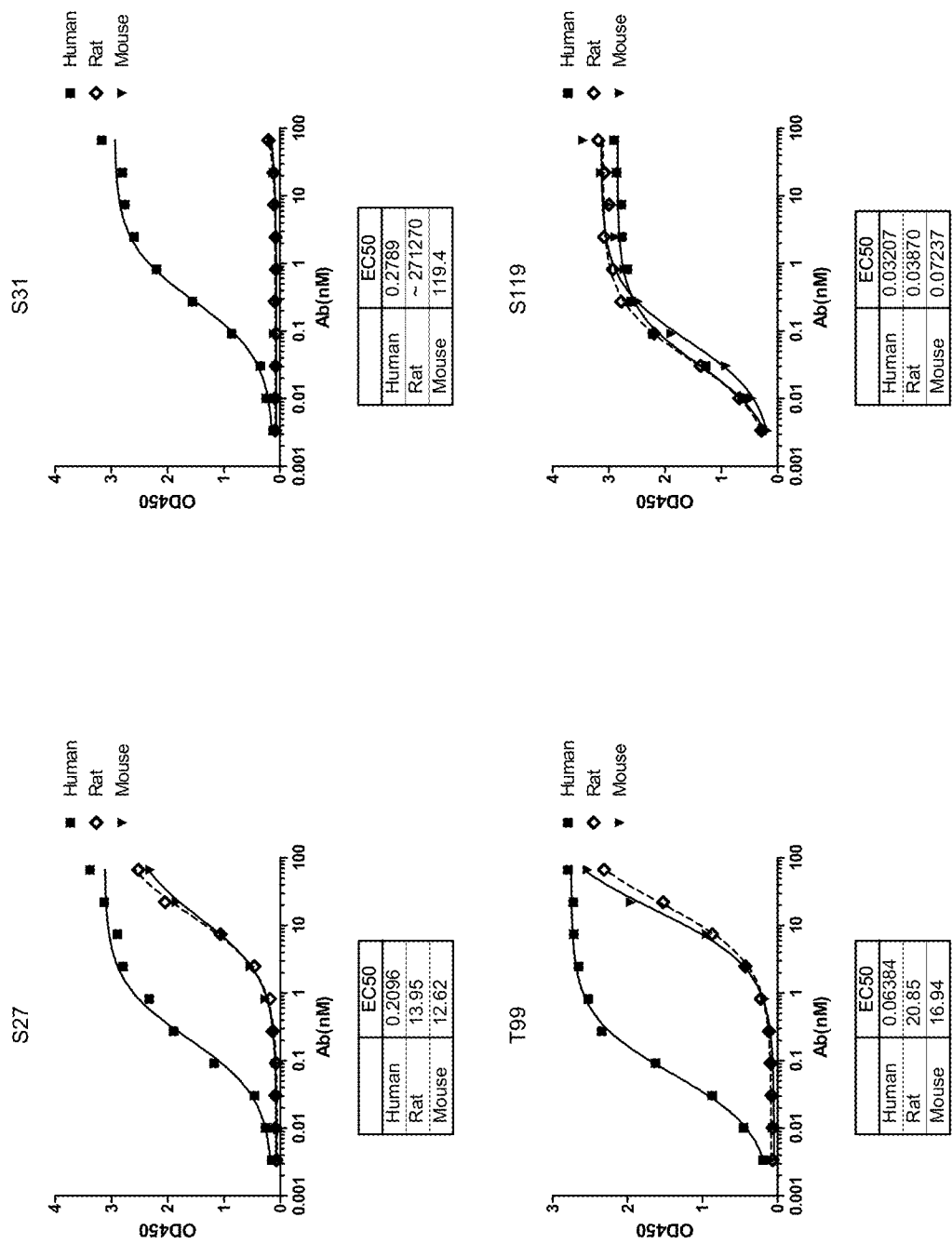
FIG. 2. The binding of human anti-LAG3 antibodies to LAG3 protein derived from various species. Anti-LAG-3 antibodies were evaluated for their binding properties to human, rat, and mouse LAG3 through enzyme-linked immunosorbent assay (ELISA).

The Binding of Human Anti-LAG3 Antibodies to LAG3 Protein Derived from Various Species To evaluate the capability of the anti-LAG-3 antibodies to bind to human, rat, and mouse LAG3 the antibodies identified in Example 1 were evaluated for their binding property through ELISA. The human, rat and mouse LAG3 ECD-Fc protein were coated to ELISA plate at 1 µg/ml with 100 µl/well. Antibodies from Example 1 were serially diluted with ELISA diluent buffer. To assess binding, LAG-3 antibodies at various concentrations 10 µg/ml, 3.333 µg/ml, 1.111 µg/ml, 0.370 µg/ml, 0.123 µg/ml, 0.041 µg/ml, 0.014 µg/ml, 0.005 µg/ml, 0.0015 µg/ml and 0.0005 µg/ml) were then added to LAG3 antigen coated plate for 1.5 hr RT. The resulting plates were washed and then labeled with anti-human IgG(Fab)-HRP antibody. The S31 can only bind to human LAG3. The S27 and T99 can bind to human LAG3 and rat/mouse LAG3 with lower potency. The S119 antibody can bind to human, rat and mouse LAG3 at high potency (FIG. 2).

Example 3

Figure 3:
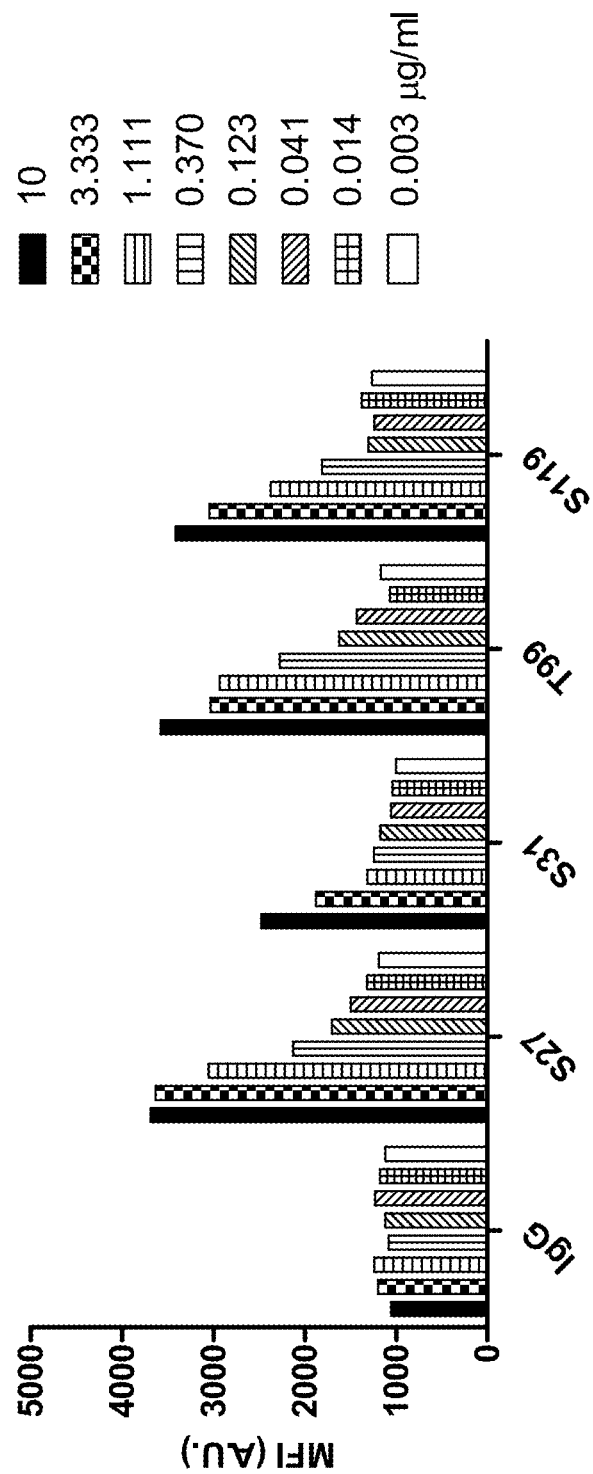
FIG. 3. The binding of human anti-LAG3 antibodies to cell surface LAG-3 antigen on activated human primary CD4$^+$ T cells. Anti-LAG-3 antibodies were assessed for binding to cell surface LAG-3 antigen on activated human primary CD4$^+$ T cells at various concentrations (10 μg/ml, 3.333 μg/ml, 1.111 μg/ml, 0.370 μg/ml, 0.123 μg/ml, 0.041 μg/ml, 0.014 μg/ml and 0.005 μg/ml).

The Binding of Human Anti-LAG3 Antibodies to Cell Surface LAG-3 Antigen on Activated Human Primary CD4+ T Cells LAG-3 is expressed on activated or exhausted T cells. CD4+ T cells were isolated using CD4 magnetic beads. The purified human CD4+ T cells were stimulated with Dynabeads® Human T-Activator CD3/CD28 for 72 hrs. Antibodies from Example 1 were serially diluted with FACS buffer. To assess binding, LAG-3 antibodies at various concentrations (10 µg/ml, 3.333 µg/ml, 1.111 µg/ml, 0.370 µg/ml, 0.123 µg/ml, 0.041 µg/ml, 0.014 µg/ml and 0.005 µg/ml) were then added to the activated human CD4 T cells in the presence of mouse anti-human LAG3 PE antibody (eBioscience, clone: 3DS223H) for 30 min on ice. The labeled cells were washed with FACS buffer and subsequently labeled with APC-conjugated anti-human IgG antibodies for 30 min on ice. The resulting cells were washed once with FACS buffer. Labeled cells were evaluated for fluorescence intensity by flow cytometry in a BD FACSCalibur™. As shown in FIG. 3, the S27, S31, T99 and S119 antibodies can dose-dependently bind to LAG3 expressed on the activated human CD4+ T cells.

Example 4

Figure 4:
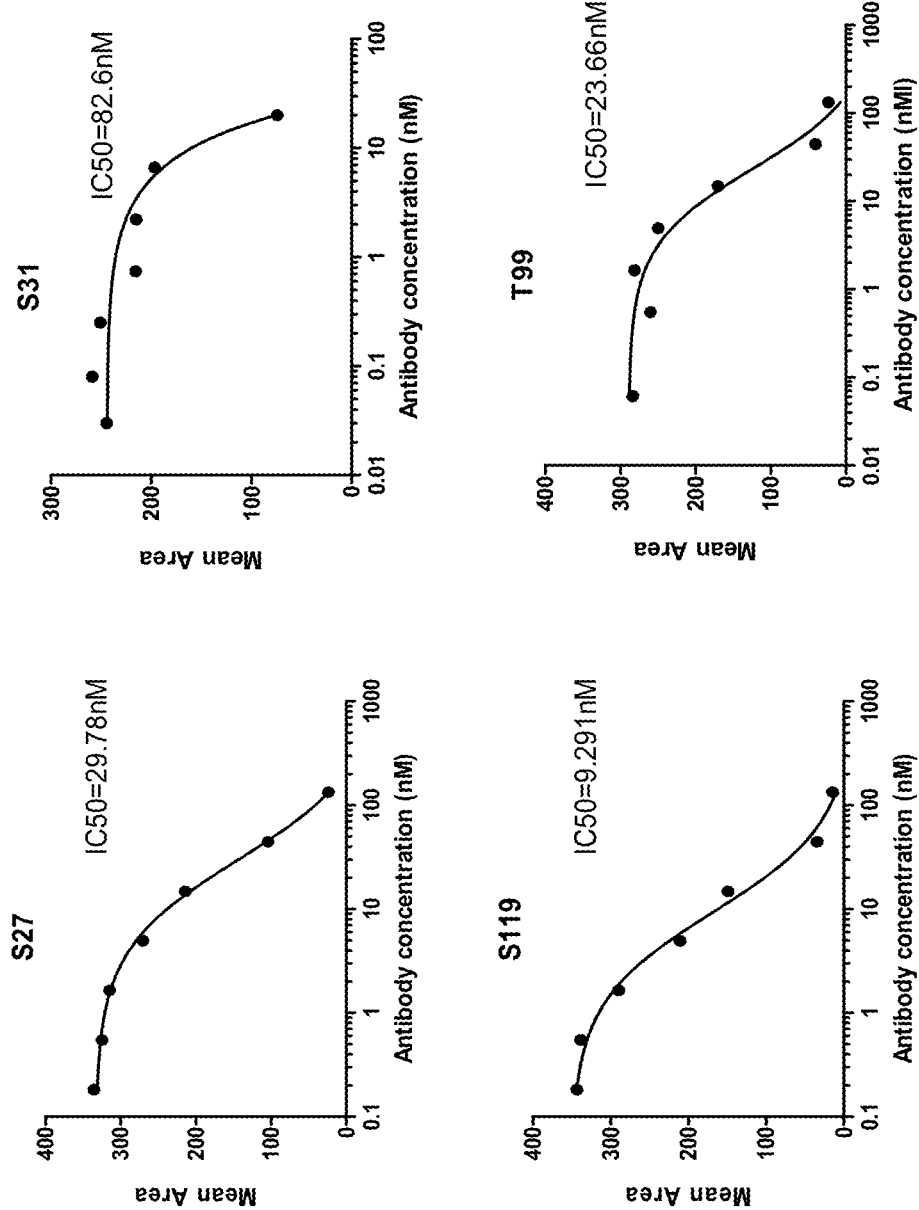
FIG. 4. Inhibition of soluble LAG-3 (sLAG) binding to MHC class II receptor by anti-LAG-3 antibody. Anti-LAG-3 antibodies were evaluated for their ability to block the binding of sLAG-3 to MHC class II receptor in an in vitro binding assay using biotin-labeled LAG-3-ECD-huFcLAG-3-Fc fusion proteins and Raji cells expressing MHC class II receptor.

Anti-LAG-3 Antibody Inhibition of Soluble LAG-3 (sLAG) Binding to MHC Class II Receptor To evaluate the ability of anti-LAG-3 antibodies to block the binding of sLAG-3 to MHC class II receptor, an in vitro binding assay was designed using biotin-labeled LAG-3-ECD-huFc fusion proteins and Raji cells expressing MHC class II receptor. Antibodies from Example 1 were serially diluted from 20 µg/mL with FACS buffer and pre-incubated with 6 µg/mL of biotin-LAG-3-ECD-huFcc for 30 min at room temperature. The antibody mixture was then added to FcR blocked Raji cells and incubated for 30 min on ice. Cells were then washed with FACS buffer and subsequently stained with streptavidin PE for 30 min on ice and subsequently washed once with FACS buffer. Labeled cells were evaluated for fluorescence intensity by flow cytometry in a BD FACSCalibur™. As shown in FIG. 4, the S27, S31, S119 and T99 antibodies can dose dependently inhibit the binding of LAG3 to its receptor MHC class II molecules.

Example 5

Figure 5:
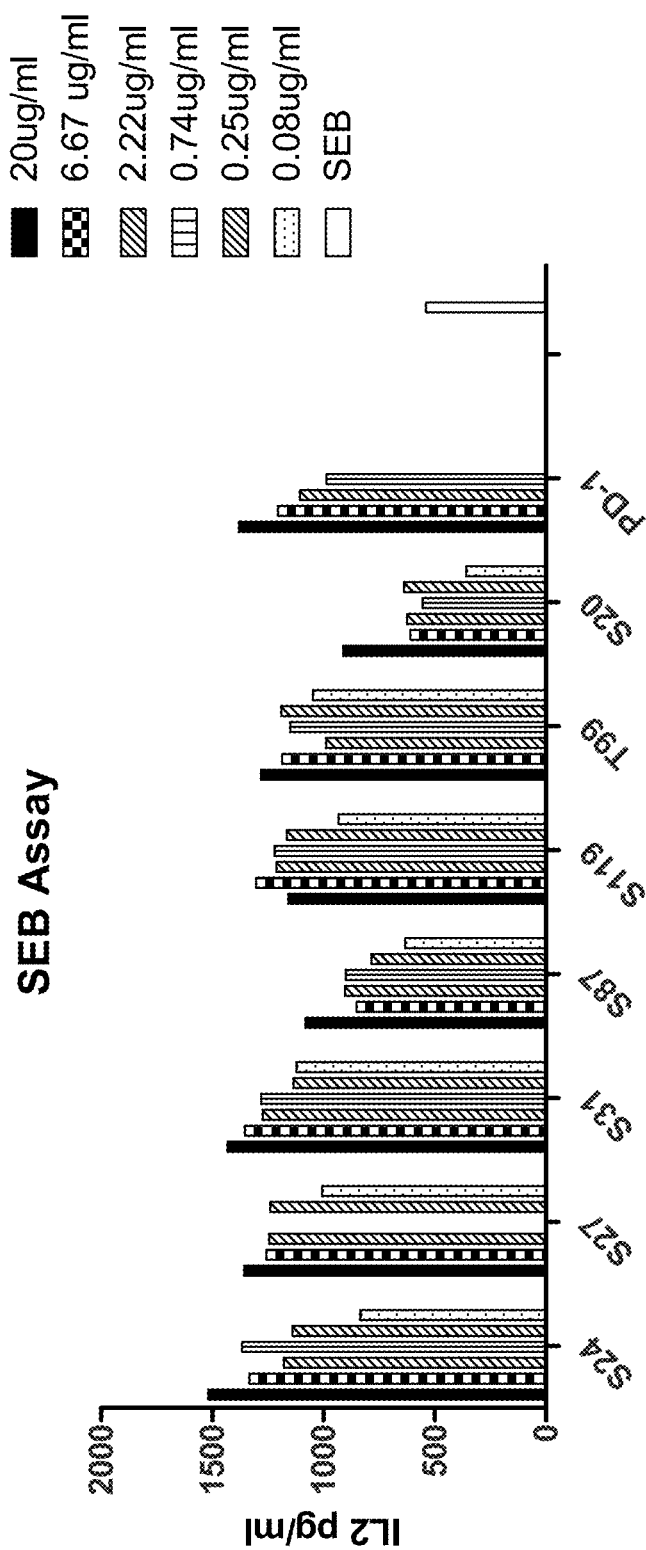
FIG. 5. Stimulation of IL-2 production in peripheral blood mononuclear cells (PBMCs) by anti-LAG-3 antibodies. Anti-LAG-3 antibodies were administrated into Staphylococcal Enterotoxin B (SEB) stimulated PBMCs at various concentrations starting from 20 μg/ml at 1:3 serial dilution for 6 doses. Three days later, IL-2 concentration in the culture supernatant was evaluated by enzyme-linked immunosorbent assay (ELISA).

Stimulation of IL-2 Production in Peripheral Blood Mononuclear Cells (PBMCs) by Anti-LAG-3 Antibodies Staphylococcal enterotoxin B (SEB) is a superantigen that simultaneously binds to MHC class II antigens and T cell receptors (TCRs), bringing them together in such a way as to induce T cell proliferation and cytokine production. $2 \times 10^5$ PBMCs were stimulated with SEB in the presence of the antibodies from Example 1 at various concentrations starting from 20 µg/ml at 1:3 serial dilutions for 6 doses. Three days later, IL-2 concentration in the culture supernatant was evaluated by ELISA. As shown in FIG. 5, similar to PD-1 antibody, anti-LAG3 antibodies(524, S27, S31, S87, S119, T99 and S20) can dose dependently enhanced IL-2 production as compared with SEB stimulation only.

Example 6

Figure 6:
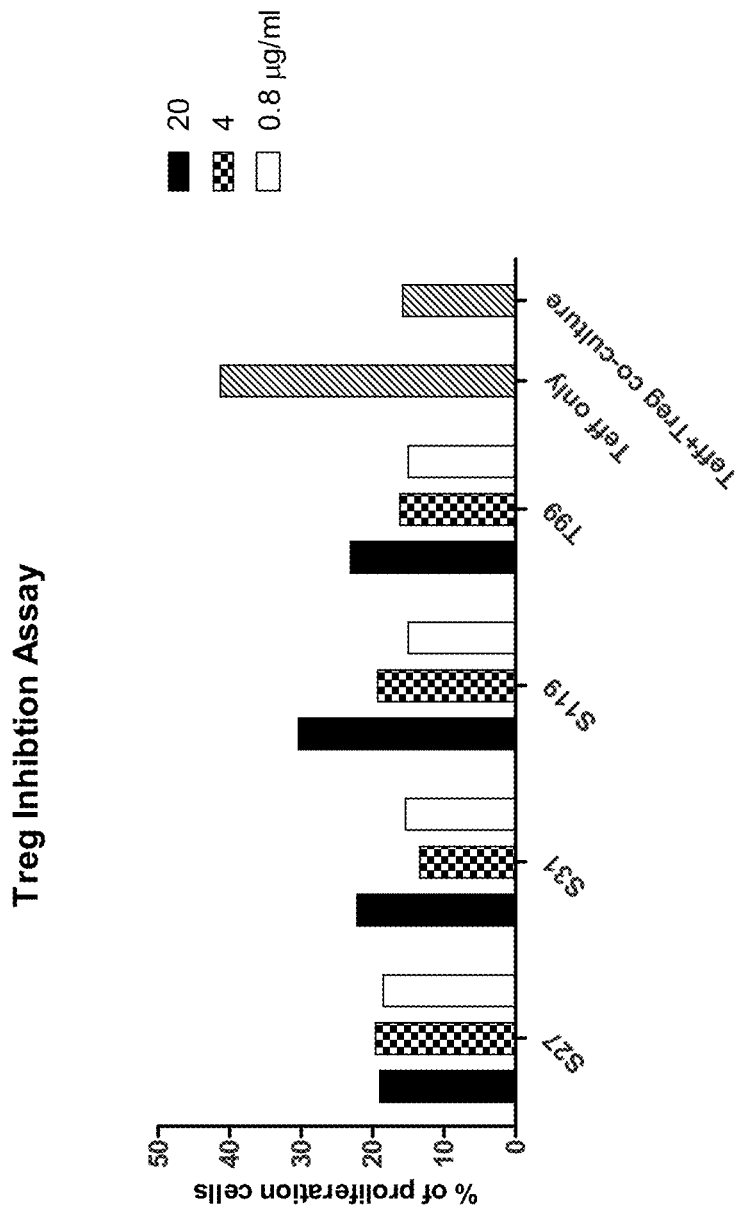
FIG. 6. Reversing the suppressive function of regulatory T cells ($T_{regs}$) on effector T cells ($T_{effs}$) using anti-LAG-3 antibodies. To evaluate the ability of anti-LAG-3 antibodies to reverse the suppressive effect of $T_{regs}$ on $T_{effs}$, the antibodies of Example 1 were used in an in vitro $T_{regs}$ suppression assay.

Reversing the Inhibition of Regulatory T Cells ($T_{regs}$) on Effector T Cells ($T_{effs}$) Using Anti-LAG-3 Antibodies LAG-3 is highly expressed on $T_{regs}$ (CD4$^+$CD25$^{hi}$) and mediates their suppressive function (*Journal of Immunology* 184:6545-51, 2010). To evaluate the ability of anti-LAG-3 antibodies on reversing the suppressive effect of $T_{regs}$ on effector T cells (CD4$^+$CD25$^-$CD127$^{hi}$), antibodies of Example 1 were used in an in vitro suppression assay. First, $T_{regs}$ (CD4$^+$CD25$^{hi}$CD127$^{low}$) and $T_{effs}$ (CD4$^+$CD25$^-$CD127$^{hi}$) were FACS-sorted by using a BD FACS Aria II system. $T_{effs}$ were then labeled with carboxyfluorescein succinimidyl ester (CFSE) and co-cultured with $T_{regs}$ at a 1:1 ratio in the presence of plate bound anti-CD3 antibodies and mitomycin C-treated antigen presenting cells. Anti-LAG-3 antibodies were next added to the cell culture and $T_{effs}$ cell proliferation were tested 5 days later. The results in FIG. 6, indicate that when Tregs were co-cultured with effector T cells, effector T cell proliferation and cytokine production was inhibited. S119 and T99 can reverse the inhibition of $T_{effs}$ by Tregs.

Example 7

Synergistic Effect of Anti-LAG3 and PD-1 Antibody Combo Treatment

Figure 7:
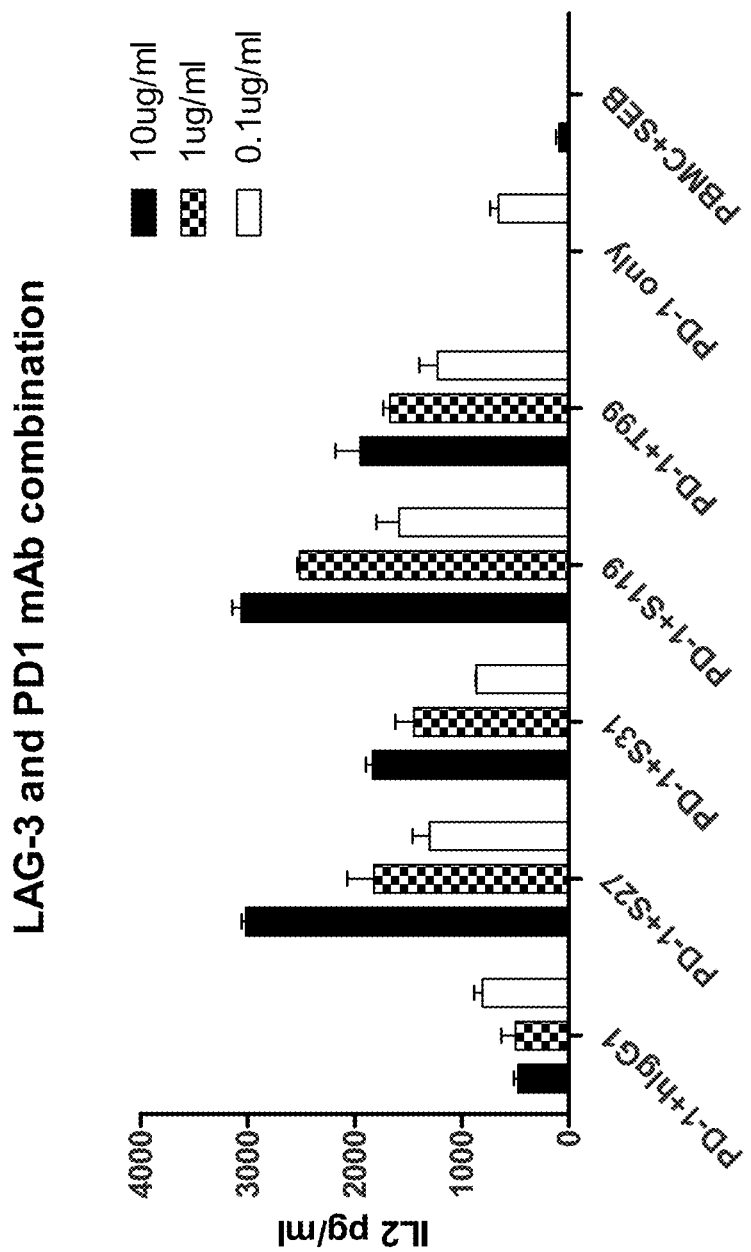
FIG. 7. Synergistic effect of anti-LAG3 and PD-1 antibody combo treatment. The anti-LAG3 antibodies were tested in combination with PD-1 antibody on SEB-stimulated PBMCs assay.

Staphylococcal enterotoxin B (SEB) is a superantigen that stimulate the human immune response. PD-1 blocking antibody can enhance the SEB stimulated IL-2 production. As shown in Example 5, anti-LAG3 antibodies can also enhance SEB mediated IL-2 production. To explore the effect of anti-LAG3 antibodies in combination with PD-1 antibody, we investigated the effect of anti-LAG3 antibody on SEB stimulation in the presence of suboptimal PD-1 stimulation. In the presence of 0.1 µg/ml PD-1 antibody, serial diluted anti-LAG3 antibodies were added to the SEB culture. IL-2 production was evaluated 72 hr later. The results in FIG. 7 indicate that anti-LAG-3 antibodies can enhance SEB stimulated T cell response in a dose-dependent manner in the presence of suboptimal PD-1 treatment, suggesting that anti-LAG3 and anti-PD-1 combo treatment have synergistic effect.

Example 8

Figure 8:
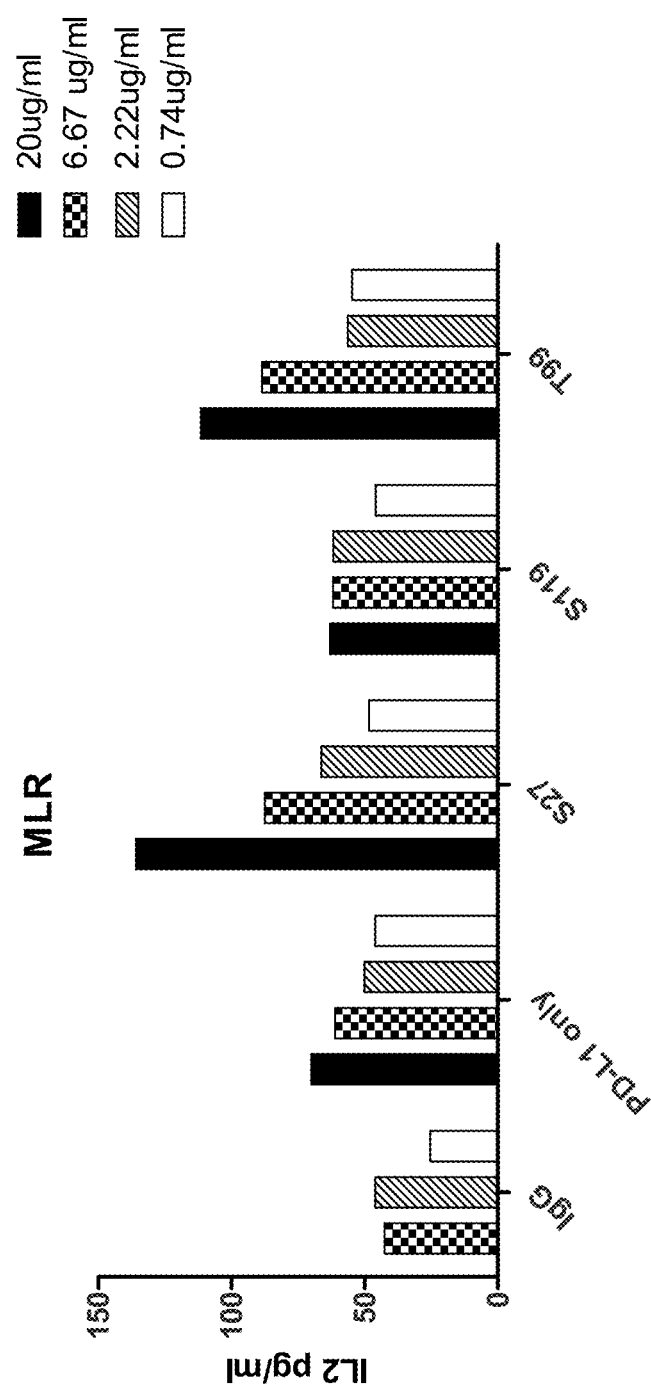
FIG. 8. Anti-LAG-3 antibodies enhance human T cell response in the presence of PD-L1 antibody. The anti-LAG3 antibodies were evaluated in combination with PD-L1 antibody on human mixed lymphocyte reaction (MLR) assay.

Anti-LAG-3 Antibodies Enhance Human T Cell Response in the Presence of PD-L1 Antibody To evaluate the effect of anti-LAG-3 antibodies in combination with PD-L1 antibody, the response of human T cells was assessed in a mixed lymphocyte reaction setting. Human DCs were differentiated from CD14$^+$ monocytes in the presence of GM-CSF and IL-4 for 7 days. CD4$^+$ T cells isolated from another donor were then co-cultured with DCs and serially diluted anti-LAG-3 antibodies and PD-L1 blocking antibody. 2 days after mixed culture, the culture supernatant was assayed for IL-2 production. The results in FIG. 8 indicate that anti-LAG-3 antibodies can significantly promote IL-2 production in conjunction with a PD-L1 antibody.

Example 9

LAG-3 Antibody BIACORE Analysis

The binding of the S20, S24, S27, S31, S87, S119, S120, S128, S136, S161 and T99 antibodies to recombinant his-tag human LAG3-ECD protein was examined by Biacore T200 using a capture method. Anti-LAG3 antibodies were captured using anti-human Fc antibody. The anti-human Fc antibody was coated on chip. Serial concentrations of his-tag human LAG3-ECD protein (0-4 nM) were injected over capture antibodies at the flow rate of 30 µl/min. The dissociation phase was 900s or 550s. The results are shown in the table below. The Biacore results for the anti-LAG3 antibodies have shown that these anti-LAG3 antibodies are high affinity binder to human LAG3.

|      | $K_a$ (M$^{-1}$s$^{-1}$) | $k_d$ (s$^{-1}$) | $K_D$ (M) |
| ---- | ---- | ---- | ---- |
| S20  | 1.65E+05 | 7.33E−06 | 4.43E−11 |
| S24  | 1.79E+06 | 1.20E−02 | 6.73E−09 |
| S27  | 7.04E+06 | 1.10E−04 | 1.56E−11 |
| S31  | 2.08E+06 | 6.25E−05 | 3.00E−11 |
| S87  | 9.28E+05 | 2.33E−06 | 2.51E−12 |
| S119 | 2.17E+07 | 1.49E−04 | 6.87E−12 |
| S120 | 1.40E+06 | 2.64E−03 | 1.88E−09 |
| S128 | 1.00E+06 | 8.17E−04 | 8.15E−10 |
| S136 | 7.98E+05 | 8.27E−05 | 1.04E−10 |
| S161 | 6.20E+05 | 5.53E−04 | 8.92E−10 |
| T99  | 7.62E+06 | 1.70E−04 | 2.24E−11 |

Example 10

Generation of Mouse Monoclonal Antibodies Against Human LAG3

This example shows how anti-human-LAG3 mouse monoclonal antibodies were generated using hybridoma technology.

Antigen:

Recombinant human LAG-3 fusion proteins were used as the immunogen to raise anti-human LAG-3 antibodies. A fusion protein comprising the entire extracellular region (domains 1-4) of human LAG-3 fused to a mouse immunoglobulin Fc domain (D1-D4 mFc) was used as the immunogen. For the ELISA binding test, a fusion protein comprising entire extracellular region (domains 1-4) or extracellular region without D1-D2 domain of human LAG-3 fused to human immunoglobulin Fc domain (D1-D4 huFc or ΔD1-D2 huFc respectively). The LAG-3 fusion proteins were prepared using standard recombinant DNA techniques.

Immunizations:

The LAG-3 fusion proteins were prepared using standard recombinant DNA techniques. Mice were immunized intraperitoneally (IP) and/or subcutaneously (SC). The mice were firstly SC immunized 50 mg immunogen and then IP immunized biweekly with 25 µg immunogen. The immune response was monitored by retroorbital bleeds. The plasma was screened by ELISA and cell-based receptor blocking assay (as described below). Mice with sufficient titers of anti-LAG-3 D1-D2 domain immunoglobulin and functional LAG3 blocker were used for fusions. Prior to sacrifice and removal of the spleens, the mice were boosted intraperitoneally with 25 µg of antigen followed by a subsequent boost with µg of antigen. The spleens were used for fusion. The hybridoma supernatant was tested for anti-LAG-3 D1-D2 domain binding and its function to block the binding of LAG3 to its receptor by cell based receptor blocking assay. Selection of Mice Producing Anti-LAG3 Blocking Antibodies.

To select mice producing anti-LAG3 blocking antibodies, sera from immunized mice was tested for binding to D1-D2 domain by ELISA. Briefly, sera were evaluated for their binding to D1-D4 huFc and its binding to ΔD1-D2 huFc was served as a counter screen. In short, D1-D4 huFc or ΔD1-D2 huFc was coated at 0.5 µg/ml overnight and then blocked by 5% BSA in PBS. The serially diluted sera were incubated with the coated antigen for 1 h at room temperature. The resulting plates were washed with PBS/T and incubated with goat anti-mouse IgG-HRP for 1 h at room temperature. The plates were developed with TMB substrate and analyzed by spectrophotometer at OD 450-630 nm. In parallel, sera were evaluated to their function to blocking the binding of LAG3 to MHCII molecules expressed on Raji cells as described Example 4. The mice with high titers specific to LAG3 D1-D2 domain and function to block the binding of LAG3 to Raji cells were selected for fusion and further screening.

Hybridoma clones 122H, 147H and 170H were selected for further analysis and sequencing.

Example 11

Binding Properties of Anti-LAG3 Mouse Monoclonal Antibodies

This example tested the binding properties of the anti-LAG3 mouse antibodies to the LAG3 proteins.
D1-D2 Specific Binders:

To evaluate the binding specificity, the purified 122H, 147H and 170H mouse monoclonal antibodies were subjected to ELISA binding test for D1-D4 huFc and ΔD1-D2 huFc antigens. Briefly, D1-D4 huFc or ΔD1-D2 huFc was coated at 0.5 µg/ml overnight and then blocked by 5% BSA in PBS. The serially diluted antibodies (starting from 1 µg/ml and 1:3 serial dilution for 10 doses) were incubated with the coated antigen for 1 hr at room temperature. The resulting plates were washed with PBS/T and incubated with goat anti-mouse IgG-HRP for 1 h at room temperature. the plates were developed with TMB substrate and analyzed by spectrophotometer at OD 450-630 nm.

Figure 9:
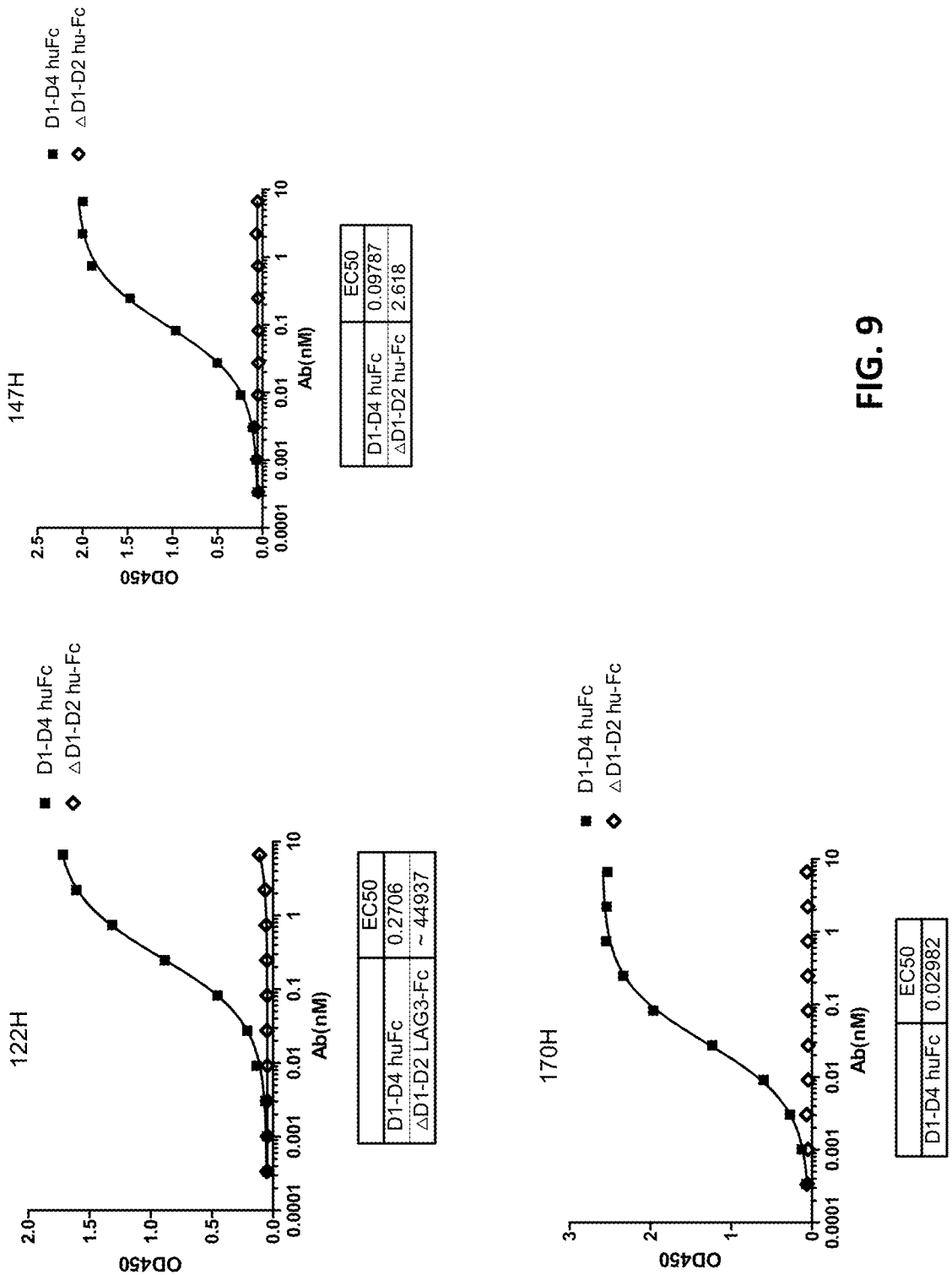
FIG. 9. ELISA results showing EC50 of the antibody for binding to full extracellular domain of LAG3 (D1-D4 huFc) but not D1-D2 deleted LAG3 (ΔD1-D2 huFc), demonstrating that 122H, 147H and 170H are potent and selective binder for D1 and D2 domain of human LAG3.

The results of the ELISA are summarized in FIG. 9, which show strong binding to full extracellular domain of LAG3 (D1-D4 huFc) but not D1-D2 deleted LAG3 (ΔD1-D2 huFc), confirm that 122H, 147H and 170H are potent and selective binder for D1 and D2 domain of human LAG3.

Example 12

Functional Properties of Anti-LAG3 Mouse Monoclonal Antibodies

Blocking the Binding of LAG3 to its Receptor

Figure 10:
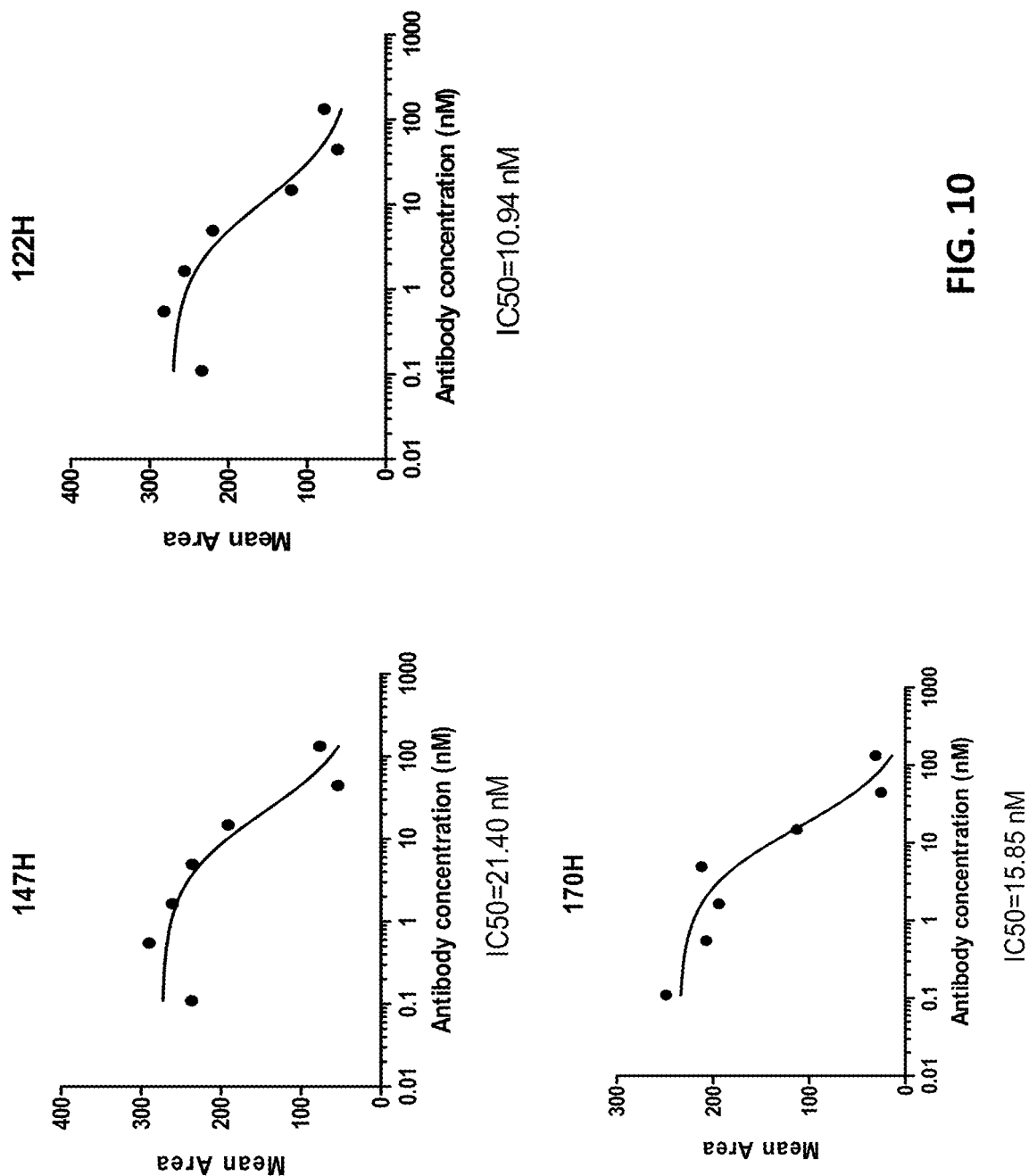
FIG. 10. 122H, 147H and 170H antibodies dose dependently inhibited the binding of LAG3 to its receptor MHC class II molecules.
Figure 11:
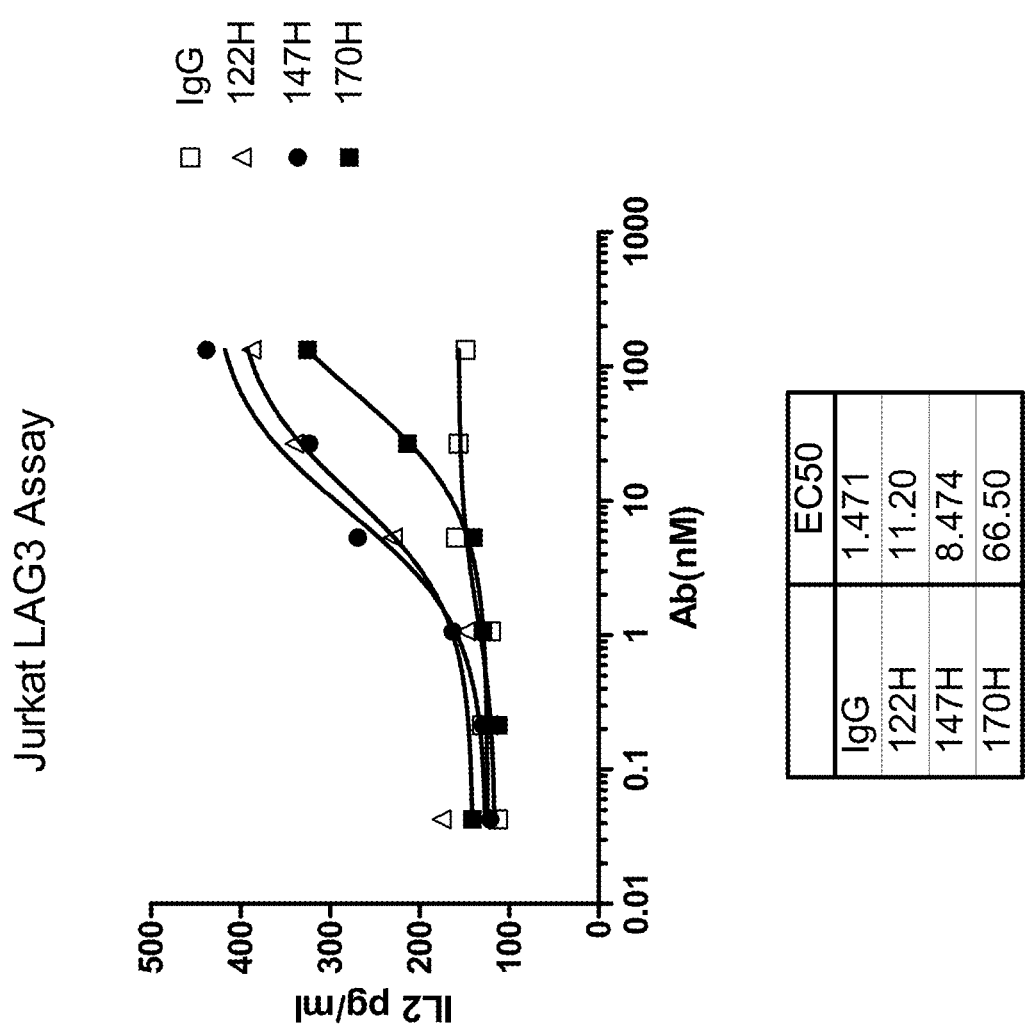
FIG. 11. 122H, 147H and 170H mouse monoclonal antibodies dose dependently promoted IL2 production by Jurkat T cells.

To evaluate the ability of anti-LAG-3 antibodies to block the binding of sLAG-3 to MHC class II receptor, an in vitro binding assay was designed using biotin-labeled LAG-3-ECD-huFc fusion proteins and Raji cells expressing MHC class II receptor. 122H, 147H and 170H mouse monoclonal antibodies were serially diluted (1:5 for 6 doses) from 20 µg/mL with FACS buffer and pre-incubated with 6 µg/mL of biotin-LAG-3-ECD-huFc for 30 min at room temperature. The antibody mixture was then added to FcR blocked Raji cells and incubated for 30 min on ice. Cells were then washed with FACS buffer and subsequently stained with streptavidin PE for 30 min on ice and subsequently washed once with FACS buffer. Labeled cells were evaluated for fluorescence intensity by flow cytometry in a BD FACSCalibur™. As shown in FIG. 10, the 122H, 147H and 170H antibodies can dose dependently inhibit the binding of LAG3 to its receptor MHC class II molecules.

Stimulation of Human T Cell Response by Anti-LAG3 Antibodies

To test the ability of the anti-LAG3 antibodies to stimulated T cell response, Jurkat T cell stimulation assay was used. Jurkat is human T cell leukemia cell line that can produce IL2 upon TCR stimulation. In this assay, Jurkat cells transfected with human LAG3 gene by lentivirus were used as the responder cells. The Raji cells which expressed MHCII was used as the antigen presenting cells (APC). Staphylococcal Enterotoxins (SE) are superantigen, which can crosslink the MHCII molecules and T cell receptor beta (TCRVβ) and stimulate T cell response. SE was used as the stimulator in this assay. In this system, ectopically expressed huLAG3 can suppress SE stimulated IL-2 production by Jurkat cells, while anti-LAG3 antibodies can reverse IL-2 production. In short, APCs ($2.5 \times 10^4$) were co-cultured with LAG3 expressing Jurkat T cells ($1 \times 10^5$) in the presence of SE stimulation. Anti-LAG3 antibodies (starting from 20 ug/ml and 1:5 serially diluted for 6 dose) were added at the beginning of the culture. 48 hr later, culture supernatant was evaluated for IL2 production by ELISA. As shown in FIG. 11, 122H, 147H and 170H mouse monoclonal antibodies can dose dependently promote IL2 production by Jurkat T cells, suggesting they can stimulate TCR stimulation by suppressing LAG3 signal to T cells.

Example 13

147H Mouse mAb Humanization Design

The mAb 147H variable region genes were employed to create a humanized mAb. In the first step of this process, the amino acid sequences of the VH and VK of mAb 147H were compared against the available database of human Ig gene sequences to find the overall best-matching human germline Ig gene sequences. For the light chain, the closest human match was the A19/JK4 gene, and for the heavy chain the closest human match was the VH1-f/JH6 gene. Humanized variable domain sequences were then designed where the CDR1 (SEQ ID NO:243), 2 (SEQ ID NO:244) and 3 (SEQ ID NO:245) of the 147H light chain were grafted onto framework sequences of the A19/JK4 gene, and the CDR1 (SEQ ID NO:240), 2 (SEQ ID NO:241), and 3 (SEQ ID NO:242) sequences of the 147H VH were grafted onto framework sequences of the VH1-f/JH6 gene. A 3D model was then generated to determine if there were any framework positions where replacing the mouse amino acid to the human amino acid could affect binding and/or CDR conformation. In the case of the heavy chain, R71, M69, R66, V67, M48, V37, R38, Y91 and Q1 (Kabat numbering) in human framework were identified and subjected to back-mutation to their mouse counterpart amino acid i.e.: R71A, M69L, R66K, V67A, M48I, V37I, R38K, Y91F and Q1E.

TABLE 5

Mouse antibody sequences

| Antibody chain or domain | Sequences (CDR residues with VH and VL are underlined) | SEQ ID NO: |
|---|---|---|
| 147H VH | QVQLQQSGSE LVRPGTSVKI SCKAS<u>GYTFT</u> <u>NYWLG</u>WIKQR PGHGLEWIG<u>D</u> <u>IYPGGDYINY</u> <u>NEKFKG</u>KATL SADTSSSTAY MQLSSLTSED SAVYFCAR<u>PN</u> <u>LPGDYW</u>GQGT SVTVSS | 238 |
| 147H VL | DIVMTQAAFS NPVTLGTSAS ISCR<u>SSKSLL</u> <u>HSNGITYLYW</u> YLQKPGQSPQ LLIY<u>QVSNLA</u> <u>S</u>GVPGRFSGS GSGTDFTLRI SRVEAEDVGV YYC<u>AQNLELP</u> <u>WT</u>FGGGTKLE IK | 239 |
| CDRH1 | GYTFTNYWLG | 240 |
| CDRH2 | DIYPGGDYIN YNEKFKG | 241 |
| CDRH3 | PNLPGDY | 242 |
| CDRL1 | RSSKSLLHSN GITYLY | 243 |
| CDRL2 | QVSNLAS | 244 |
| CDRL3 | AQNLELPWT | 245 |

The amino acid sequences of the humanized antibodies are listed: 147H-1, 147H-2, 147H-3, 147H-4, 147H-5, 147H-6, 147H-7, 147H-8, 147H-9, 147H-10, 147H-11, 147H-12, 147H-13, and 147H-14, each having a different heavy chain but all share a common light chain.

TABLE 6

Humanized antibodies and back mutations

| Antibody chain | Sequences (CDR underlined; back mutations bold and underlined) | SEQ ID NO: |
|---|---|---|
| 147H-1 VH | QVQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVTM <u>T</u>RDTSISTAY MELSRLRSDD TAVYYCAR<u>PN</u> <u>LPGDYW</u>GQGT TVTVSS | 246 |
| 147H-2 VH | QVQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVTM <u>T</u>ADTSISTAY MELSRLRSDD TAVYYCAR<u>PN</u> <u>LPGDYW</u>GQGT TVTVSS | 247 |
| 147H-3 VH | QVQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVT<u>L</u> <u>T</u>ADTSISTAY MELSRLRSDD TAVYYCAR<u>PN</u> <u>LPGDYW</u>GQGT TVTVSS | 248 |
| 147H-4 VH | QVQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u><u>KATL</u> <u>T</u>ADTSISTAY MELSRLRSDD TAVYYCAR<u>PN</u> <u>LPGDYW</u>GQGT TVTVSS | 249 |
| 147H-5 VH | QVQLVQSGAE VKKPGASVKV SCKAS<u>GYTFT</u> <u>NYWLG</u>WVRQA PGQGLEWI<u>GD</u> <u>IYPGGDYINY</u> <u>NEKFKG</u><u>KATL</u> <u>T</u>ADTSISTAY MELSRLRSDD TAVYYCAR<u>PN</u> <u>LPGDYW</u>GQGT TVTVSS | 250 |
| 147H-6 VH | QVQLVQSGAE VKKPGASVKV SCKAS<u>GYTFT</u> <u>NYWLG</u>W<u>IK</u>QA PGQGLEWIG<u>D</u> <u>IYPGGDYINY</u> <u>NEKFKG</u><u>KATL</u> <u>T</u>ADTSISTAY MELSRLRSDD TAVYYCAR<u>PN</u> <u>LPGDYW</u>GQGT TVTVSS | 251 |
| 147H-7 VH | QVQLVQSGAE VKKPGASVKV SCKAS<u>GYTFT</u> <u>NYWLG</u>W<u>IK</u>QA PGQGLEWIG<u>D</u> <u>IYPGGDYINY</u> <u>NEKFKG</u><u>KATL</u> <u>T</u>ADTSISTAY MELSRLRSDD TAVY<u>F</u>CAR<u>PN</u> <u>LPGDYW</u>GQGT TVTVSS | 252 |
| 147H-8 VH | <u>E</u>VQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVTM TRDTSISTAY MELSRLRSDD TAVYYCAR<u>PN</u> <u>LPGDYW</u>GQGT TVTVSS | 253 |
| 147H-9 VH | <u>E</u>VQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVTM <u>T</u>ADTSISTAY MELSRLRSDD TAVYYCAR<u>PN</u> <u>LPGDYW</u>GQGT TVTVSS | 254 |
| 147H-10 VH | <u>E</u>VQLVQSGAE VKKPGASVKV SCKAS<u>GYTFT</u> <u>NYWLG</u>WVRQA PGQGLEWMG<u>D</u> <u>IYPGGDYINY</u> <u>NEKFKG</u>RVT<u>L</u> <u>T</u>ADTSISTAY MELSRLRSDD TAVYYCAR<u>PN</u> <u>LPGDYW</u>GQGT TVTVSS | 255 |

TABLE 6-continued

Humanized antibodies and back mutations

| Antibody chain | Sequences (CDR underlined; back mutations bold and underlined) | SEQ ID NO: |
|---|---|---|
| 147H-11 VH | EVQLVQSGAE VKKPGASVKV SCKAS<u>GYTFT</u> <u>NYWLGW</u>VRQA PGQGLEWMGD <u>IYPGGDYINY NEKFKG</u>KATL TADTSISTAY MELSRLRSDD TAVYYCARPN <u>LPGDYWGQGT</u> TVTVSS | 256 |
| 147H-12 VH | EVQLVQSGAE VKKPGASVKV SCKAS<u>GYTFT</u> <u>NYWLGW</u>VRQA PGQGLEWIGD <u>IYPGGDYINY NEKFKG</u>KATL TADTSISTAY MELSRLRSDD TAVYYCARPN <u>LPGDYWGQGT</u> TVTVSS | 257 |
| 147H-13 VH | EVQLVQSGAE VKKPGASVKV SCKAS<u>GYTFT</u> <u>NYWLGW</u>IKQA PGQGLEWIGD <u>IYPGGDYINY NEKFKG</u>KATL TADTSISTAY MELSRLRSDD TAVYYCARPN <u>LPGDYWGQGT</u> TVTVSS | 258 |
| 147H-14 VH | EVQLVQSGAE VKKPGASVKV SCKAS<u>GYTFT</u> <u>NYWLGW</u>IKQA PGQGLEWIGD <u>IYPGGDYINY NEKFKG</u>KATL TADTSISTAY MELSRLRSDD TAVYFCARPN <u>LPGDYWGQGT</u> TVTVSS | 259 |
| 147H VL | DIVMTQSPLS LPVTPGEPAS ISC<u>RSSKSLL</u> <u>HSNGITYLYW</u> YLQKPGQSPQ LLIY<u>QVSNLA</u> SGVPDRFSGS GSGTDFTLKI SRVEAEDVGV YYC<u>AQNLELP</u> <u>WT</u>FGGGTKVE IK | 260 |

The humanized VH and VK genes were produced synthetically and then respectively cloned into vectors containing the human gamma 1 and human kappa constant domains. The pairing of the human VH and the human VK created 40 humanized antibodies.

Example 14

Binding Properties of Anti-LAG5 147H Humanized Monoclonal Antibodies

Affinity Ranking of Humanized Antibodies by Octet® RED96 System

To explore the binding kinetics of the humanized antibody, this example performed the affinity ranking by using Octet Red 96. As shown in the table below, 147H-6, 147H-7, 147H-13 and 147H-14 show better affinity.

| Antibody | KD (M) | kon(1/Ms) | kdis(1/s) |
|---|---|---|---|
| 147H-1 | 3.54E-08 | 1.09E+05 | 3.86E-03 |
| 147H-2 | 3.16E-08 | 9.93E+04 | 3.14E-03 |
| 147H-3 | 3.65E-08 | 9.25E+04 | 3.38E-03 |
| 147H-4 | 3.98E-08 | 8.62E+04 | 3.43E-03 |
| 147H-5 | 3.13E-08 | 9.58E+04 | 3.00E-03 |
| 147H-6 | 1.53E-08 | 1.20E+05 | 1.84E-03 |
| 147H-7 | 1.57E-08 | 1.52E+05 | 2.39E-03 |
| 147H-8 | 3.23E-08 | 1.65E+05 | 5.33E-03 |
| 147H-9 | 6.64E-08 | 6.74E+04 | 4.48E-03 |
| 147H-10 | 8.23E-08 | 4.91E+04 | 4.04E-03 |
| 147H-11 | 4.22E-08 | 1.07E+05 | 4.51E-03 |
| 147H-12 | 5.52E-08 | 6.23E+04 | 3.44E-03 |
| 147H-13 | 2.16E-08 | 1.08E+05 | 2.34E-03 |
| 147H-14 | 2.32E-08 | 1.08E+05 | 2.50E-03 |

Full Kinetic Affinity of Humanized Antibodies by Octet® RED96 System

To explore the binding kinetics of the humanized antibody, this example further performed the full kinetic affinity testing by running various dose of antigen (50 nM, 25 nM, 12.5 nM, 6.15 nM, 3.125 nM) by using Octet Red 96. The binding affinity was calculated by software in Octet® RED96 System. As shown in the table, 147H-6, 147H-7, 147H-13 and 147H-14 showed comparable affinity with 147H chimeric antibody.

| Antibody | KD (M) | kon(1/Ms) | kdis(1/s) |
|---|---|---|---|
| 147H chimeric | 2.71E-08 | 8.01E+04 | 2.17E-03 |
| 147H-6 | 2.48E-08 | 1.05E+05 | 2.59E-03 |
| 147H-6 | 2.65E-08 | 1.18E+05 | 3.12E-03 |
| 147H-13 | 1.82E-08 | 1.04E+05 | 1.90E-03 |
| 147H-14 | 2.07E-08 | 9.87E+04 | 2.04E-03 |

Example 15

Functional Properties of Anti-LAG3 Mouse Monoclonal Antibodies

Stimulation of Human T Cell Response by Anti-LAG3 Antibodies

Figure 12:
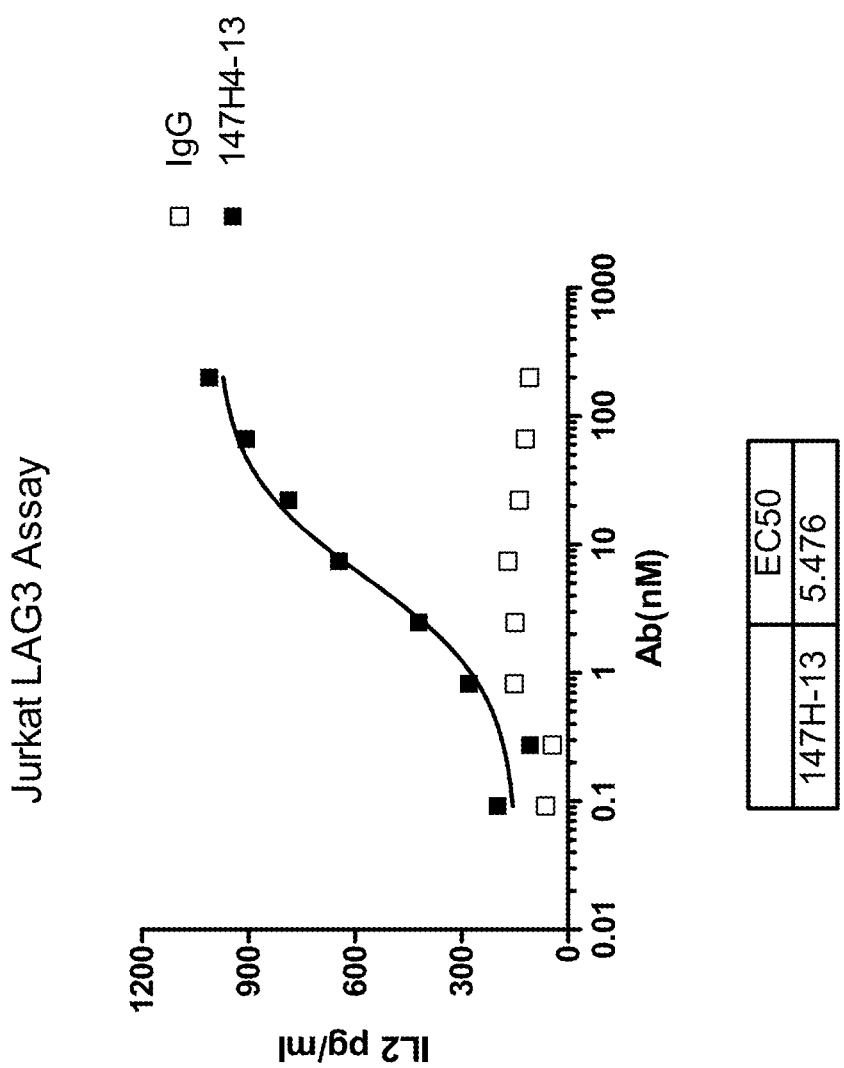
FIG. 12. Humanized monoclonal antibody 147H-13 dose dependently promoted the IL2 production by Jurkat T cells.
Figure 13:
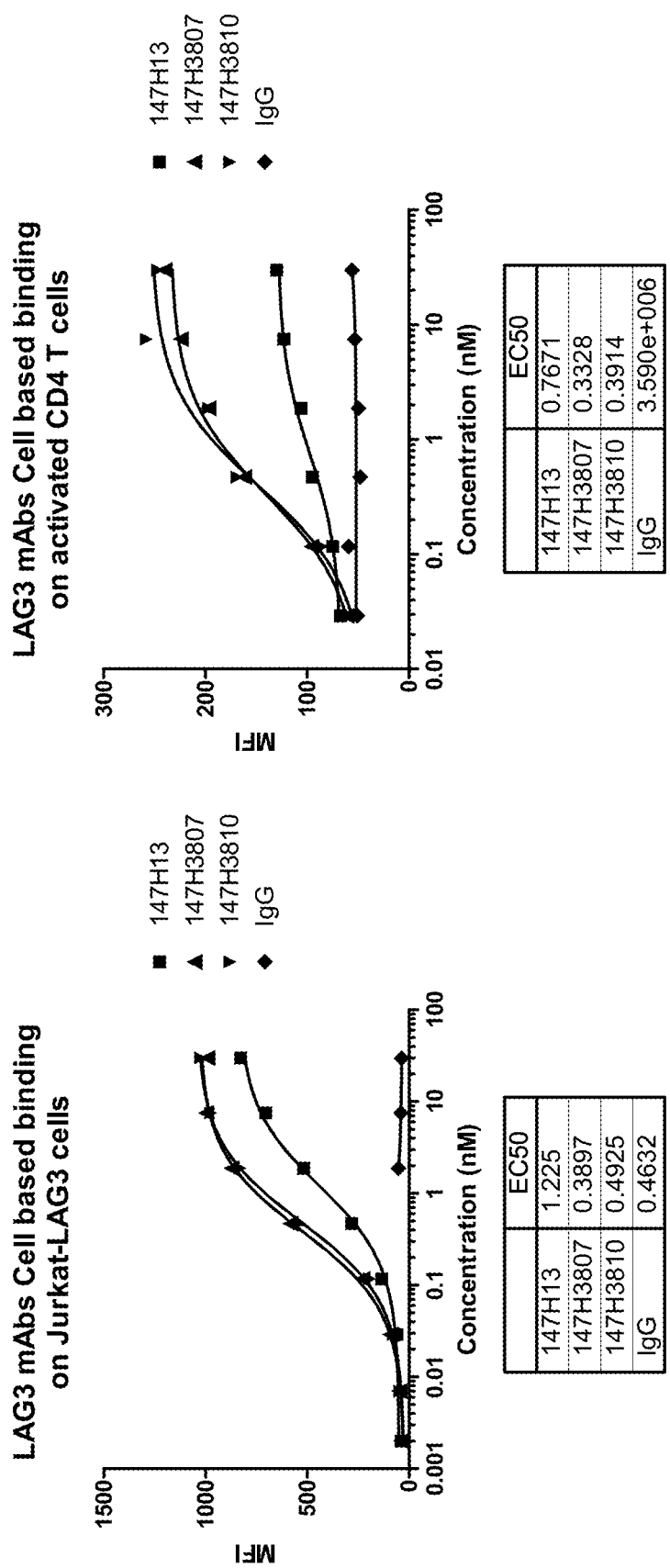
FIG. 13. Binding curves of anti-LAG3 antibodies on Jurkat-LAG3 cells and activated CD4 T cell.

To test the ability of anti-LAG3 antibodies to stimulated T cell response, Jurkat T cell stimulation assay was used as described in Example 12. Anti-LAG3 antibodies (starting from 30 μg/ml and 1:3 serially diluted for 6 doses) were added at the beginning of the culture. 48 hr later, culture supernatant was evaluated for IL2 production by ELISA. As shown in FIG. 12, 147H-13 humanized monoclonal antibodies can dose dependently promote IL2 production by Jurkat T cells, suggesting they can stimulate the TCR stimulation by suppressing LAG3 signal to T cells.

Example 16

Affinity Maturation of Anti-LAG3 147H Humanized Monoclonal Antibodies

To improve antigen binding affinity, this example performed affinity maturation of 147H4-13 using phage display technology. Strategy 1: The CDRH3 and CDRL3 of 147H-13 were targeted for codon-based mutagenesis. CDRH3 and CDRL3 were randomized at position H95-H102 and L89-L97 (Kabat numbering), respectively. Strategy 2: Each CDR was targeted for single codon based mutagenesis using CDR walking approach. Then CDRH1, CDRH2, CDRL1 combined to library 1. The CDRH3, CDRL2, CDRL3 combined to library 2.

In both strategies, libraries were subject to three or four rounds of affinity-based solution-phase phage display selection with decreasing concentration of antigen at each round. A relatively high antigen concentration (10 nM) was used for the first round. The antigen concentration was decreased 10-fold each of the subsequent three rounds or 100-fold each the subsequent two rounds to select for high affinity variants. Individual variants from the final round were tested for positive binding to antigen by ELISA screening. Off-rate ranking of individual variants was determined by Octet Red 96 (Fortebio, USA). Mutations with improved affinity were combined to generate new LAG3 antibodies. Affinity was further confirmed by Biacore which suggested N58V of CDR H2 significantly increased Koff, while N91Y of CDR L3 improved Kon.

TABLE 7

Antibody affinity maturation

| No. | Sequence (CDR underlined, mutation bold) |
|---|---|
| 147H3421 | VH: (SEQ ID NO: 261)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PN<br>LPKDHWGQGT</u> TVTVSS<br>VL: (SEQ ID NO: 262)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3422 | VH: (SEQ ID NO: 263)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PD<br>LPGDYWGQGT</u> TVTVSS<br>VL: (SEQ ID NO: 264)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3423 | VH: (SEQ ID NO: 265)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PG<br>LPKDYWGQGT</u> TVTVSS<br>VL: (SEQ ID NO: 266)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3424 | VH: (SEQ ID NO: 267)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PN<br>LPKDYWGQGT</u> TVTVSS<br>VL: (SEQ ID NO: 268)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3425 | VH: (SEQ ID NO: 269)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PN<br>LPRDYWGQGT</u> TVTVSS<br>VL: (SEQ ID NO: 270)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3426 | VH: (SEQ ID NO: 271)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PG<br>LPRDYWGQGT</u> TVTVSS<br>VL: (SEQ ID NO: 272)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |
| 147H 3427 | VH: (SEQ ID NO: 273)<br>EVQLVQSGAE VKKPGASVKV SCKAS<u>GYTFT NYWLG</u>WIKQA PGQGLEWIG<u>D<br>IYPGGDYINY NEKFKG</u>KATL TADTSISTAY MELSRLRSDD TAVYYCAR<u>PG<br>LPQDYWGQGT</u> TVTVSS<br>VL: (SEQ ID NO: 274)<br>DIVMTQSPLS LPVTPGEPAS ISC<u>RSSKSLL HSNAITYLYW</u> YLQKPGQSPQ<br>LLIY<u>QVSNLA</u> SGVPDRFSGS GSGTDFTLKI SRVEAEDVGV YYC<u>AQNLELP<br>WTF</u>GGGTKVE IK |

TABLE 7-continued

Antibody affinity maturation

No. Sequence (CDR underlined, mutation bold)

147H 3428
VH: (SEQ ID NO: 275)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PD
LPKD**<u>YWGQGT TVTVSS</u>
VL: (SEQ ID NO: 276)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYC<u>AQNLELP
WT</u>FGGGTKVE IK 147H 3429
VH: (SEQ ID NO: 277)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
L**PGDYWGQGT TVTVSS
VL: (SEQ ID NO: 278)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYCG<u>QNLELP
WT</u>FGGGTKVE IK 147H 3430
VH: (SEQ ID NO: 279)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
L**PGDYWGQGT TVTVSS
VL: (SEQ ID NO: 280)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYC<u>AQNLEMP
WT</u>FGGGTKVE IK 147H 3431
VH: (SEQ ID NO: 281)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
L**PGDYWGQGT TVTVSS
VL: (SEQ ID NO: 282)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYCGQNLEMP
WTFGGGTKVE IK 147H 3432
VH: (SEQ ID NO: 283)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
L**PGDYWGQGT TVTVSS
VL: (SEQ ID NO: 284)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYC<u>AQYLEEP
WT</u>FGGGTKVE IK 147H 3433
VH: (SEQ ID NO: 285)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
L**PGDYWGQGT TVTVSS
VL: (SEQ ID NO: 286)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYC<u>AQYLELP
WT</u>FGGGTKVE IK 147H 3508
VH: (SEQ ID NO: 287)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
LPKDH**WGQGT TVTVSS
VL: (SEQ ID NO: 288)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYCGQNLELP
WTFGGGTKVE IK 147H 3549
VH: (SEQ ID NO: 289)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR**PN
LPKDH**WGQGT TVTVSS
VL: (SEQ ID NO: 290)
DIVMTQSPLS LPVTPGEPAS ISC<u>RSSKSLL HSNAITYLYW</u> YLQKPGQSPQ
LLIY<u>QVSNLA</u> SGVPDRFSGS GSGTDFTLKI SRVEAEDVGV YYC<u>AQYLEEP
WT</u>FGGGTKVE IK

TABLE 7-continued

| Antibody affinity maturation | |
|---|---|
| No. | Sequence (CDR underlined, mutation bold) |

147H
3550

VH: (SEQ ID NO: 291)
EVQLVQSGAE VKKPGASVKV SCKAS<u>GYTFT</u> <u>NYWLG</u>WIKQA PGQGLEWIG<u>D</u>
<u>IYPGGDYINY</u> <u>NEKFKG</u>KATL TADTSISTAY MELSRLRSDD TAVYYCAR<u>PN</u>
<u>LPKDH</u>WGQGT TVTVSS
VL: (SEQ ID NO: 292)
DIVMTQSPLS LPVTPGEPAS ISC<u>RSSKSLL</u> <u>HSNAITYLYW</u> YLQKPGQSPQ
LLIY<u>QVSNLA</u> SGVPDRFSGS GSGTDFTLKI SRVEAEDVGV YYC<u>AQYLELP</u>
<u>WT</u>FGGGTKVE IK 147H
3663

VH: (SEQ ID NO: 293)
EVQLVQSGAE VKKPGASVKV SCKAS<u>GYTFE</u> <u>NYWLG</u>WIKQA PGQGLEWIG<u>D</u>
<u>IYPGGDYIVY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 294)
DIVMTQSPLS LPVTPGEPAS ISC<u>RSSKSLL</u> <u>HSNAITYLYW</u> YLQKPGQSPQ
LLIY<u>QVSNLA</u> RGVPDRFSGS GSGTDFTLKI SRVEAEDVGV YYC<u>AQNLELP</u>
<u>WT</u>FGGGTKVE IK 147H
3664

VH: (SEQ ID NO: 295)
EVQLVQSGAE VKKPGASVKV SCKAS<u>GYMFT</u> <u>NYWLG</u>WIKQA PGQGLEWIG<u>D</u>
<u>IYPGGDYINY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 296)
DIVMTQSPLS LPVTPGEPAS ISC<u>RSSKSLL</u> <u>HSNAITYLYW</u> YLQKPGQSPQ
LLIY<u>QKSNLA</u> SGVPDRFSGS GSGTDFTLKI SRVEAEDVGV YYC<u>AQNLELP</u>
<u>WT</u>FGGGTKVE IK 147H
3665

VH: (SEQ ID NO: 297)
EVQLVQSGAE VKKPGASVKV SCKAS<u>GYTFD</u> <u>NYWLG</u>WIKQA PGQGLEWIG<u>D</u>
<u>IYPGGDIINY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 298)
DIVMTQSPLS LPVTPGEPAS ISC<u>RSSKSLL</u> <u>HSNAITYLYW</u> YLQKPGQSPQ
LLIY<u>QVSNLA</u> VGVPDRFSGS GSGTDFTLKI SRVEAEDVGV YYC<u>AQNLELP</u>
<u>WT</u>FGGGTKVE IK 147H
3666

VH: (SEQ ID NO: 299)
EVQLVQSGAE VKKPGASVKV SCKAS<u>GYTFG</u> <u>NYWLG</u>WIKQA PGQGLEWIG<u>D</u>
<u>IYPGGDVINY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 300)
DIVMTQSPLS LPVTPGEPAS ISC<u>RSSKSLL</u> <u>HSNAITYLYW</u> YLQKPGQSPQ
LLIY<u>QVSNLA</u> LGVPDRFSGS GSGTDFTLKI SRVEAEDVGV YYC<u>AQNLELP</u>
<u>WT</u>FGGGTKVE IK 147H
3667

VH: (SEQ ID NO: 301)
EVQLVQSGAE VKKPGASVKV SCKAS<u>GYTFT</u> <u>NYWLW</u>WIKQA PGQGLEWIG<u>D</u>
<u>IFPGGDYINY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 302)
DIVMTQSPLS LPVTPGEPAS ISC<u>RSSKSLL</u> <u>HSNAITYLYW</u> YLQKPGQSPQ
LLIY<u>QVDNLA</u> SGVPDRFSGS GSGTDFTLKI SRVEAEDVGV YYC<u>AQNLELP</u>
<u>WT</u>FGGGTKVE IK 147H
3668

VH: (SEQ ID NO: 303)
EVQLVQSGAE VKKPGASVKV SCKAS<u>GYTFT</u> <u>NYWLG</u>WIKQA PGQGLEWIG<u>D</u>
<u>IYPGGDYIVY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 304)
DIVMTQSPLS LPVTPGEPAS ISC<u>RSSKSLL</u> <u>HSNAITYLYW</u> YLQKPGQSPQ
LLIY<u>QVSNLA</u> TGVPDRFSGS GSGTDFTLKI SRVEAEDVGV YYC<u>AQNLELP</u>
<u>WT</u>FGGGTKVE IK 147H
3669

VH: (SEQ ID NO: 305)
EVQLVQSGAE VKKPGASVKV SCKAS<u>GYLFT</u> <u>NYWLG</u>WIKQA PGQGLEWIG<u>D</u>
<u>IYPGGDYIVY</u> <u>NEKFKG</u>KATL TADTSISTAY MELSRLRSDD TAVYYCAR<u>PN</u>
<u>LPGDY</u>WGQGT TVTVSS
VL: (SEQ ID NO: 306)
DIVMTQSPLS LPVTPGEPAS ISC<u>RSSKSLL</u> <u>HSNAITYLYW</u> YLQKPGQSPQ
LLIY<u>QVSNLA</u> SGVPDRFSGS GSGTDFTLKI SRVEAEDVGV YYC<u>AQNLELP</u>
<u>WT</u>FGGGTKVE IK

TABLE 7-continued

Antibody affinity maturation

| No. | Sequence (CDR underlined, mutation bold) |
|---|---|

147H
3670
VH: (SEQ ID NO: 307)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR<u>PN
LPGDY</u>WGQGT TVTVSS
VL: (SEQ ID NO: 308)
DIVMTQSPLS LPVTPGEPAS ISC<u>RSSKSLL HSNAITYLY</u>W YLQKPGQSPQ
LLIYH<u>VSNLA</u> SGVPDRFSGS GSGTDFTLKI SRVEAEDVGV YYC<u>AQNLELP
WT</u>FGGGTKVE IK 147H
3675
VH: (SEQ ID NO: 309)
EVQLVQSGAE VKKPGASVKV SCKAS<u>GYTFT NYWLW</u>WIKQA PGQGLEWIG<u>D
IYPGGDLINY NEKFKG</u>KATL TADTSISTAY MELSRLRSDD TAVYYCAR<u>PN
LPGDY</u>WGQGT TVTVSS
VL: (SEQ ID NO: 310)
DIVMTQSPLS LPVTPGEPAS ISC<u>RSSKSLL HSNAITYLY</u>W YLQKPGQSPQ
LLIYH<u>VSNLA</u> SGVPDRFSGS GSGTDFTLKI SRVEAEDVGV YYC<u>AQNLELP
WT</u>FGGGTKVE IK 147H
3676
VH: (SEQ ID NO: 311)
EVQLVQSGAE VKKPGASVKV SCKAS<u>GYTFT NYWLS</u>WIKQA PGQGLEWIG<u>D
IYPGGDHINY NEKFKG</u>KATL TADTSISTAY MELSRLRSDD TAVYYCAR<u>PN
LPGDY</u>WGQGT TVTVSS
VL: (SEQ ID NO: 312)
DIVMTQSPLS LPVTPGEPAS ISC<u>RSSKSLL HSNAITYLY</u>W YLQKPGQSPQ
LLIY<u>QVSNLA</u> SGVPDRFSGS GSGTDFTLKI SRVEAEDVGV YYC<u>AQNLELP
WT</u>FGGGTKVE IK 147H
3677
VH: (SEQ ID NO: 313)
EVQLVQSGAE VKKPGASVKV SCKAS<u>GYTFT NYWLW</u>WIKQA PGQGLEWIGE
<u>IYPGGDYITY NEKFKG</u>KATL TADTSISTAY MELSRLRSDD TAVYYCAR<u>PN
LPGDY</u>WGQGT TVTVSS
VL: (SEQ ID NO: 314)
DIVMTQSPLS LPVTPGEPAS ISC<u>RSSKSLL HSNAITYLY</u>W YLQKPGQSPQ
LLIY<u>QVSNRA</u> SGVPDRFSGS GSGTDFTLKI SRVEAEDVGV YYC<u>AQNLELP
WT</u>FGGGTKVE IK 147H
3678
VH: (SEQ ID NO: 315)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR<u>PN
LPGDY</u>WGQGT TVTVSS
VL: (SEQ ID NO: 316)
DIVMTQSPLS LPVTPGEPAS ISC<u>RSSKSLL HSNAITYLY</u>W YLQKPGQSPQ
LLIY<u>QVDNLA</u> SGVPDRFSGS GSGTDFTLKI SRVEAEDVGV YYC<u>AQNLELP
WT</u>FGGGTKVE IK 147H
3679
VH: (SEQ ID NO: 317)
EVQLVQSGAE VKKPGASVKV SCKAS<u>FYTFT NYWLG</u>WIKQA PGQGLEWIG<u>D
IYPGGDYIVY NEKFKG</u>KATL TADTSISTAY MELSRLRSDD TAVYYCAR<u>PN
LPGDY</u>WGQGT TVTVSS
VL: (SEQ ID NO: 318)
DIVMTQSPLS LPVTPGEPAS ISC<u>RSSKSLL HSNAITYLY</u>W YLQKPGQSPQ
LLIY<u>QVSNLA</u> SGVPDRFSGS GSGTDFTLKI SRVEAEDVGV YYC<u>AQNLELP
WT</u>FGGGTKVE IK 147H
3790
VH: (SEQ ID NO: 319)
EVQLVQSGAE VKKPGASVKV SCKAS<u>GYTFT NYWLG</u>WIKQA PGQGLEWIG<u>D
IYPGGDYINY NEKFKG</u>KATL TADTSISTAY MELSRLRSDD TAVYYCAR<u>PN
LPKDY</u>WGQGT TVTVSS
VL: (SEQ ID NO: 320)
DIVMTQSPLS LPVTPGEPAS ISC<u>RSSKSLL HSNAITYLY</u>W YLQKPGQSPQ
LLIY<u>QVSNLA</u> TGVPDRFSGS GSGTDFTLKI SRVEAEDVGV YYC<u>AQNLELP
WT</u>FGGGTKVE IK 147H
3791
VH: (SEQ ID NO: 321)
EVQLVQSGAE VKKPGASVKV SCKAS<u>GYTFT NYWLG</u>WIKQA PGQGLEWIG<u>D
IYPGGDYIVY NEKFKG</u>KATL TADTSISTAY MELSRLRSDD TAVYYCAR<u>PN
LPGDY</u>WGQGT TVTVSS
VL: (SEQ ID NO: 322)
DIVMTQSPLS LPVTPGEPAS ISC<u>RSSKSLL HSNAITYLY</u>W YLQKPGQSPQ
LLIY<u>QVSNLA</u> SGVPDRFSGS GSGTDFTLKI SRVEAEDVGV YYC<u>GQNLELP
WT</u>FGGGTKVE IK

TABLE 7-continued

Antibody affinity maturation

No.        Sequence (CDR underlined, mutation bold)

147H       VH: (SEQ ID NO: 323)
3792       EVQLVQSGAE VKKPGASVKV SCKAS<u>GYTFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPGDY</u>WGQGT TVTVSS
           VL: (SEQ ID NO: 324)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>A</u>Q<u>Y</u>LELP
           <u>WT</u>FGGGTKVE IK

147H       VH: (SEQ ID NO: 325)
3793       EVQLVQSGAE VKKPGASVKV SCKAS<u>GYLFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPGDY</u>WGQGT TVTVSS
           VL: (SEQ ID NO: 326)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>GQNLELP</u>
           <u>WT</u>FGGGTKVE IK

147H       VH: (SEQ ID NO: 327)
3794       EVQLVQSGAE VKKPGASVKV SCKAS<u>GYLFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPGDY</u>WGQGT TVTVSS
           VL: (SEQ ID NO: 328)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>A</u>Q<u>Y</u>LELP
           <u>WT</u>FGGGTKVE IK

147H       VH: (SEQ ID NO: 329)
3807       EVQLVQSGAE VKKPGASVKV SCKAS<u>GYTFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPKDH</u>WGQGT TVTVSS
           VL: (SEQ ID NO: 330)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>A</u>Q<u>Y</u>LELP
           <u>WT</u>FGGGTKVE IK

147H       VH: (SEQ ID NO: 331)
3808       EVQLVQSGAE VKKPGASVKV SCKAS<u>GYTFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPKDH</u>WGQGT TVTVSS
           VL: (SEQ ID NO: 332)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>GQY</u>LELP
           <u>WT</u>FGGGTKVE IK

147H       VH: (SEQ ID NO: 333)
3809       EVQLVQSGAE VKKPGASVKV SCKAS<u>GYLFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPKDH</u>WGQGT TVTVSS
           VL: (SEQ ID NO: 334)
           DIVMTQSPLS LPVTPGEPAS ISC<u>RSSKSLL</u> <u>HSNAITYLY</u>W YLQKPGQSPQ
           LLIY<u>QVSNLA</u> SGVPDRFSGS GSGTDFTLKI SREAEDVGV YYC<u>A</u>Q<u>Y</u>LELP
           <u>WT</u>FGGGTKVE IK

147H       VH: (SEQ ID NO: 335)
3810       EVQLVQSGAE VKKPGASVKV SCKAS<u>GYLFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPKDH</u>WGQGT TVTVSS
           VL: (SEQ ID NO: 336)
           DIVMTQSPLS LPVTPGEPAS ISC<u>RSSKSLL</u> <u>HSNAITYLY</u>W YLQKPGQSPQ
           LLIY<u>QVSNLA</u> TGVPDRFSGS GSGTDFTLKI SREAEDVGV YYC<u>A</u>Q<u>Y</u>LELP
           <u>WT</u>FGGGTKVE IK

147H       VH: (SEQ ID NO: 337)
3811       EVQLVQSGAE VKKPGASVKV SCKAS<u>GYLFT</u> <u>NYWLG</u>WIKQA PGQGLEWIG<u>D</u>
           <u>IYPGGDYIVY</u> <u>NEKFKG</u>KATL TADTSISTAY MELSRLRSDD TAVYYCAR<u>PN</u>
           <u>LPKDH</u>WGQGT TVTVSS
           VL: (SEQ ID NO: 338)
           DIVMTQSPLS LPVTPGEPAS ISC<u>RSSKSLL</u> <u>HSNAITYLY</u>W YLQKPGQSPQ
           LLIY<u>QVSNLA</u> TGVPDRFSGS GSGTDFTLKI SREAEDVGV YYC<u>GQY</u>LELP
           <u>WT</u>FGGGTKVE IK

TABLE 8

Summary of mutations and mutated CDR regions:

| | Original sequence (SEQ ID NO: _) | Example substitutions | Example mutated sequences (SEQ ID NO: _) |
|---|---|---|---|
| CDRH1 | GYTFTNYWLG (240) | Y27: F<br>T28: M, L<br>T30: E, D, G<br>G35: W, S | GYTFENYWLG (339)<br>GYMFTNYWLG (340)<br>GYTFDNYWLG (341)<br>GYTFGNYWLG (342)<br>GYTFTNYWLW (343)<br>GYLFTNYWLG (344)<br>GYTFTNYWLS (345)<br>GFTFTNYWLG (346) |
| CDRH2 | DIYPGGDYINYNEKFKG (241) | D50: E<br>Y52: F<br>Y56: I, V, L, H<br>N58: V, T | DIYPGGDYIVYNEKFKG (347)<br>DIYPGGDIINYNEKFKG (348)<br>DIYPGGDVINYNEKFKG (349)<br>DIFPGGDTINYNEKFKG (350)<br>DIYPGGDLINYNEKFKG (351)<br>DIYPGGDHINYNEKFKG (352)<br>EIYPGGDYITYNEKFKG (353) |
| CDRH3 | PNLPGDY (242) | N96: D, G<br>G99: K, R, Q<br>Y102: H | PNLPKDH (354)<br>PDLPGDY (355)<br>PGLPKDY (356)<br>PNLPKDY (357)<br>PNLPRDY (358)<br>PGLPRDY (359)<br>PGLPQDY (360)<br>PDLPKDY (361) |
| CDRL1 | RSSKSLLHSNGITYLY (243) | N28: Q | RSSKSLLHSQGITYLY (376) |
| CDRL2 | QVSNLAS (244) | Q50: H<br>V51: K<br>S52: D<br>L54: R<br>S56: R, V, L, T | QVSNLAR (362)<br>QKSNLAS (363)<br>QVSNLAV (364)<br>QVSNLAL (365)<br>QVDNLAS (366)<br>QVSNLAT (367)<br>HVSNLAS (368)<br>QVSNRAS (369) |
| CDRL3 | AQNLELPWT (245) | A89: G<br>N91: Y<br>L94: M, E | GQNLELPWT (370)<br>AQNLEMPWT (371)<br>GQNLEMPWT (372)<br>AQYLEEPWT (373)<br>AQYLELPWT (374)<br>GQYLELPWT (375) |

Example 17

Binding Properties of Affinity Matured Anti-LAG5 147H Humanized Monoclonal Antibodies The binding kinetics of affinity matured antibodies to recombinant his-tag human LAG3-ECD protein was examined by Biacore T200, as stated in Example 9. The results were shown in Table below. The Biacore results showed that these anti-LAG3 antibodies had better affinity than parent 147H-13.

| | KD (M) | kon(1/Ms) | kdis(1/s) |
|---|---|---|---|
| 147H-13 | 1.4E−08 | 2.2E+06 | 3.0E−02 |
| 147H 3421 | 8.1E−09 | 1.4E+06 | 1.2E−02 |
| 147H 3508 | 1.4E−09 | 2.9E+06 | 4.2E−03 |
| 147H 3549 | 9.2E−10 | 7.4E+06 | 6.8E−03 |
| 147H 3550 | 9.8E−10 | 8.7E+06 | 8.5E−03 |
| 147H 3663 | 6.8E−09 | 7.9E+05 | 5.4E−03 |
| 147H 3669 | 8.8E−09 | 7.2E+05 | 6.3E−03 |
| 147H 3790 | 5.9E−09 | 7.7E+05 | 4.5E−03 |
| 147H 3791 | 1.2E−09 | 2.1E+06 | 2.5E−03 |
| 147H 3792 | 5.9E−10 | 4.9E+06 | 2.9E−03 |
| 147H 3793 | 1.3E−09 | 1.8E+06 | 2.3E−03 |
| 147H 3794 | 7.2E−10 | 3.7E+06 | 2.7E−03 |
| 147H 3807 | 5.1E−10 | 4.0E+06 | 2.0E−03 |
| 147H B3808 | 7.5E−10 | 4.3E+06 | 3.2E−03 |
| 147H 3809 | 4.7E−10 | 4.3E+06 | 2.0E−03 |
| 147H 3810 | 4.1E−10 | 4.7E+06 | 1.9E−03 |
| 147H 3811 | 5.9E−10 | 4.9E+06 | 2.9E−03 |

To confirm the capability of affinity matured anti-LAG-3 antibodies binding to human LAG3, 2 antibodies with highest affinity (B3807 and B3810) along with parent antibody 147H-13 were evaluated using ELISA, which was described in Example 2. EC50 of B3807, B3810 along with parent antibody was showed in table below. Both 3807 and B3810 showed superior binding capability than parent antibody 147H-13.

| Name | EC50 (nM) |
|---|---|
| 147H-13 | 6.5 |
| 147H 3807 | 0.41 |
| 147H 3810 | 0.49 |

To further confirm affinity matured anti-LAG-3 antibodies could bind to cell-derived human LAG3, both inducible hLAG3 expressed Jurkat cells and activated PBMCs were used to test the binding capability of B3807 and B3810. In brief, Jurkat cells were resuspended in FACS buffer. Anti-LAG-3 antibodies and isotype control were 4-fold serially diluted in FACS buffer with a dose ranging from 20 nM to 30 pM. The serially diluted antibodies were added to the cell suspension and incubated for 30 minutes on ice. Then after removal of unbound antibodies, cells were stained with anti-human IgG conjugated with Alexa Fluor 633 (Thermo, A21091). Fluorescence measurement was acquired on FACSCelesta flow cytometer and analyzed in Flowjo to determine the mean fluorescence intensities (MFI). To test anti-LAG3 antibodies' ability of binding to native human LAG3, PBMCs from health donor were stimulated with anti-CD3 (BD, 555336) and anti-CD28 (BD, 555725) both at a concentration of 1 ug/ml. Following 3 days' stimulation, cells were harvested and incubated with anti-LAG3 antibodies for 30 mins on ice. The cells were stained with anti-human CD4 and anti-human IgG. Analysis of antibodies binding to CD4+ cells were carried out on FACSCelesta flow cytometry. The results of cytometry analysis were summarized in table below which showed EC50 of antibodies binding to cell-derived human LAG3. FIG. 13 is a graph showing the binding curve of anti-LAG3 antibodies. EC50 of tested antibodies was showed below.

| Cell-based binding assay | EC50 (nM) | | |
|---|---|---|---|
| | 147H-13 | 147H 3807 | 147H 3810 |
| Jurkat-LAG3 | 1.2 | 0.4 | 0.5 |
| Activated CD4 T cells | 0.77 | 0.33 | 0.39 |

Example 18

Blocking of LAG3 Binding to MHC Class II

To measure the ability of anti-LAG3 monoclonal antibodies to block the interaction between human LAG3 and MHCII, the LAG3 and MHC II binding assay (Cisbio, 64ICP03PEG) were performed utilizing homogeneous TR-FRET technology, following the protocol provided by the kit manufacturer. Anti-human LAG3 antibodies were 3-fold diluted ranging from 100 nM to 5 pM (10 points). Fluorescence data was acquired on a PerkinElmer Envision plate reader and a four-parameter dose-response curve was fitted to obtain IC50 of each antibody. IC50 of tested antibodies was showed in table below.

| Name | IC50 (nM) |
|---|---|
| 147H-13 | 2.2-7.6 |
| 147H 3421 | 1.5 |
| 147H 3508 | 0.55 |
| 147H 3549 | 0.44 |
| 147H 3550 | 0.39 |
| 147H 3663 | 2.7 |
| 147H 3668 | 0.9 |
| 147H 3669 | 1.2 |
| 147H 3792 | 0.73 |
| 147H 3794 | 0.63 |
| 147H 3807 | 0.31 |
| 147H 3808 | 0.5 |
| 147H 3809 | 0.96 |
| 147H 3810 | 0.63 |
| 147H 3811 | 0.59 |

Example 19

Stimulation of Human T Cell Response by Anti-LAG3 Antibodies

Figure 14:
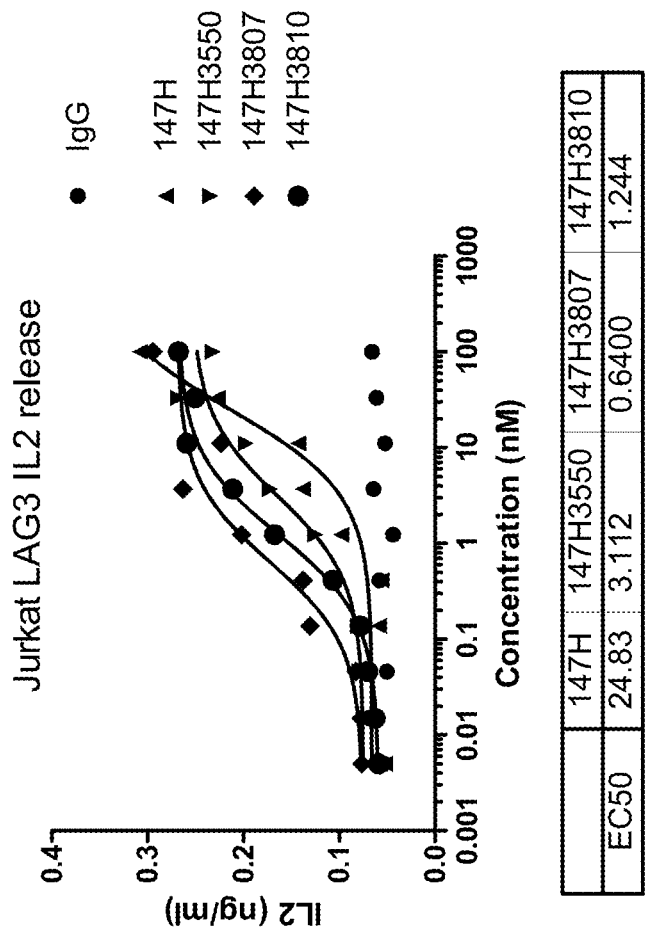
FIG. 14. The effect of affinity maturated anti-LAG3 antibodies on stimulating IL2 release by Jurkat T cells.

To test the ability of anti-LAG3 antibodies to stimulate T cell response, hLAG3-expressed Jurkat cells were used, as described in Example 13. Similarly, in each well of 96-well plate, Jurkat cells ($1 \times 10^5$) were incubated with Raji cells ($1 \times 10^4$) in the presence of 0.1 ng/ml SE. Anti-LAG3 antibodies were 3-fold diluted and added to the cells at a final concentration ranging from 100 nM to 5 pm. 48 hours later, IL2 from the culture medium was measured using a homogeneous TR-FRET assay. (PerkinElmer, TRF1221M) FIG. 14 shows the curve of anti-LAG3 antibodies in stimulating IL2 release. Affinity matured clones showed better potency in stimulating T cell response.

Example 20

The Effect of Anti-LAG3 Antibodies on Blocking the Binding of Galectin-3 or LSECtin to LAG3

Figure 15:
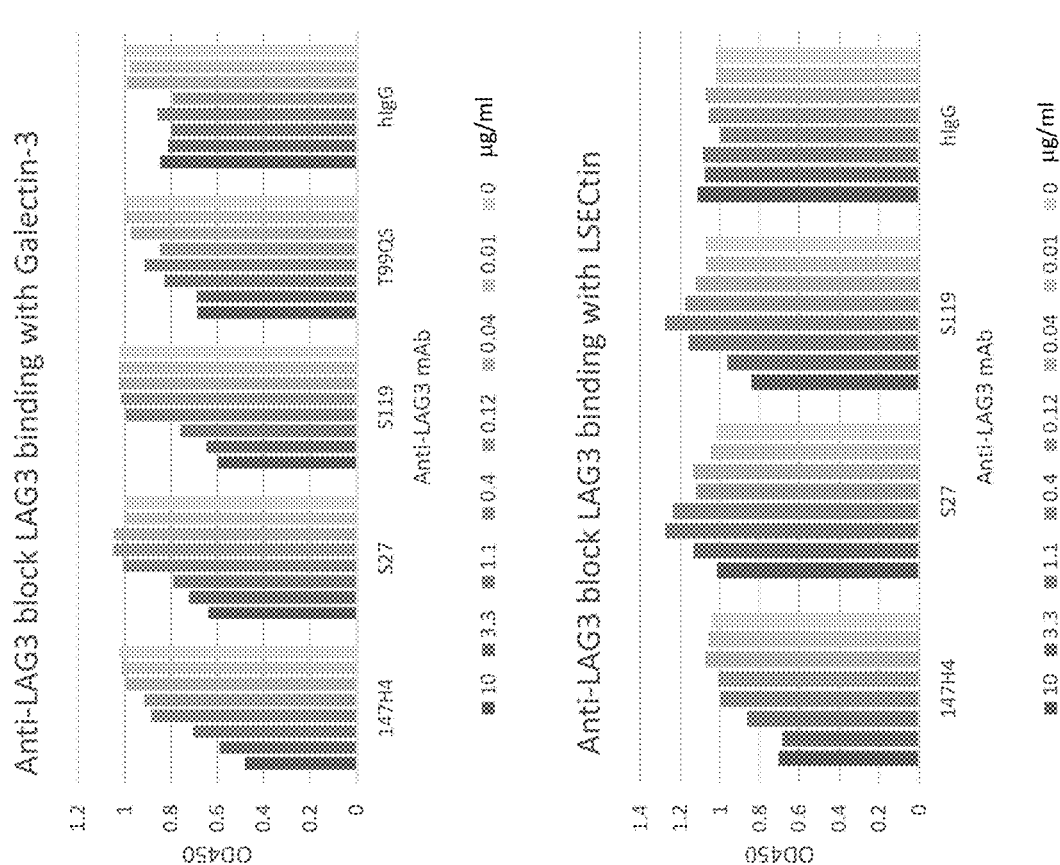
FIG. 15. The effect of anti-LAG3 antibodies on blocking the binding of Galectin-3 or LSECtin to LAG3.

It has been reported that LAG3 has other ligands including Galectin-3 (Cancer Immunol Res. 2015; 3:412-423) and LSECtin (J Biol Chem. 2004; 279:18748-18758). Interactions with these two potential alternative ligands may serve to broaden LAG3's impact on T-cell function, particularly with regard to an intrinsic role for LAG3 on $CD8^+$ T cells in the tumor microenvironment. Recombinant Galectin-3 or LSECtin were coated on the 96 well plated overnight at 4° C. Serially diluted anti-LAG3 antibodies (starting from 10 µg/ml and 1:3 dilution) and biotin-labeled LAG3-Fc protein were incubated with Glectin-3 or LSECtin coated wells at room temperature for 2 hours. After extensive wash with the wash buffer, streptavidin-HRP was added. As shown in FIG. 15, the 147H, S27 and S119 antibodies dose-dependently inhibited the binding of Galectin-3 or LSECtin to LAG3 protein.

Example 21

Figure 16:
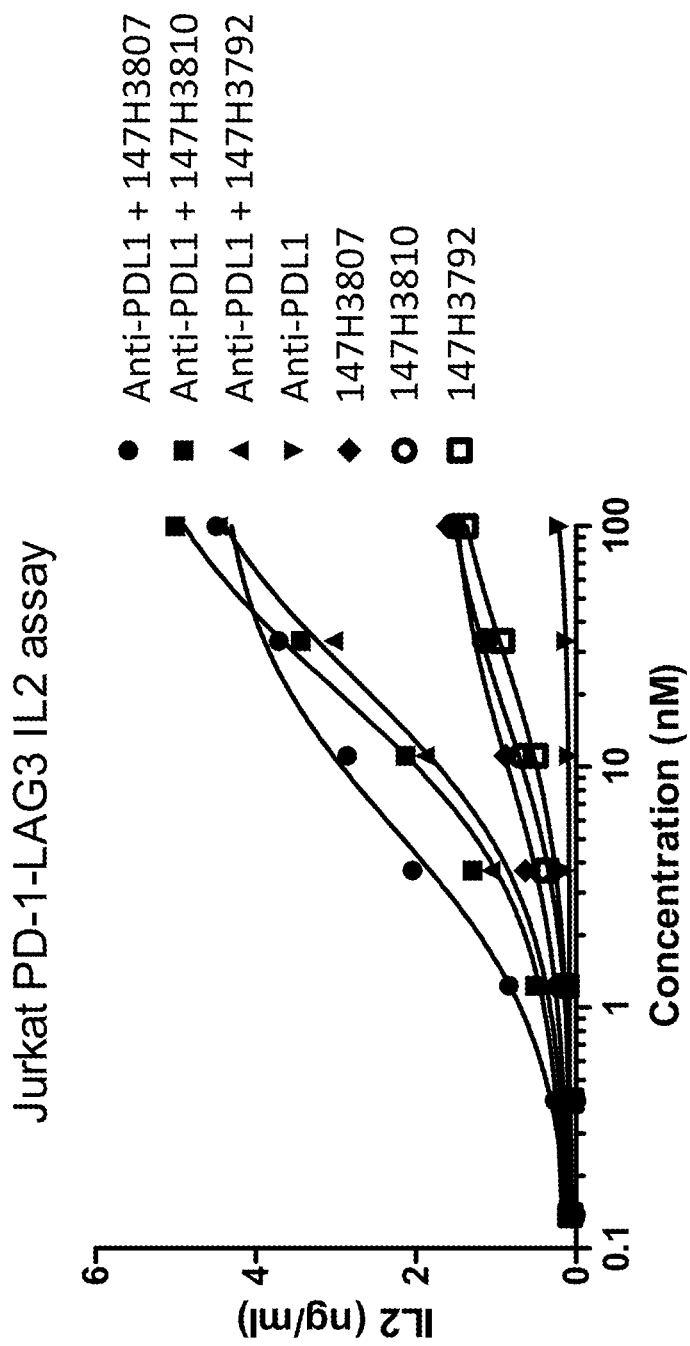
FIG. 16. Anti LAG3 antibodies in combination with anti PD-L1 antibody significantly produced more IL-2 than each alone.

Synergistic Effect of Combination Treatment of Anti-Human LAG3 and Anti-Human PD-L1 Antibody To evaluate the effect of anti-LAG-3 antibodies in combination with PD-L1 antibody, Jurkat T cell stimulation assay were used. Jurkat cells were overexpressed with human LAG3 and human PD-1, and Raji cells which endogenously expressed MHCII were transfected with human PD-L1. SE was used as the stimulator in this assay. In brief, PD-L1 expressing Raji ($1 \times 10^4$) was co-cultured with LAG3-PD-1 expressing Jurkat T cells ($1 \times 10^5$) in the presence of SE stimulation. The anti-LAG3 antibodies with or without an anti-PD-L1 antibody were serially diluted and added at the beginning of the culture. 48 hr later, the culture supernatant was collected for IL2 release using TR-FRET assay (PerkinElmer, TRF1221M). As shown in FIG. 16, anti LAG3 antibodies in combination with the anti PD-L1 antibody can significantly produce more IL-2 than its corresponding mono-antibodies.

Figure 17:
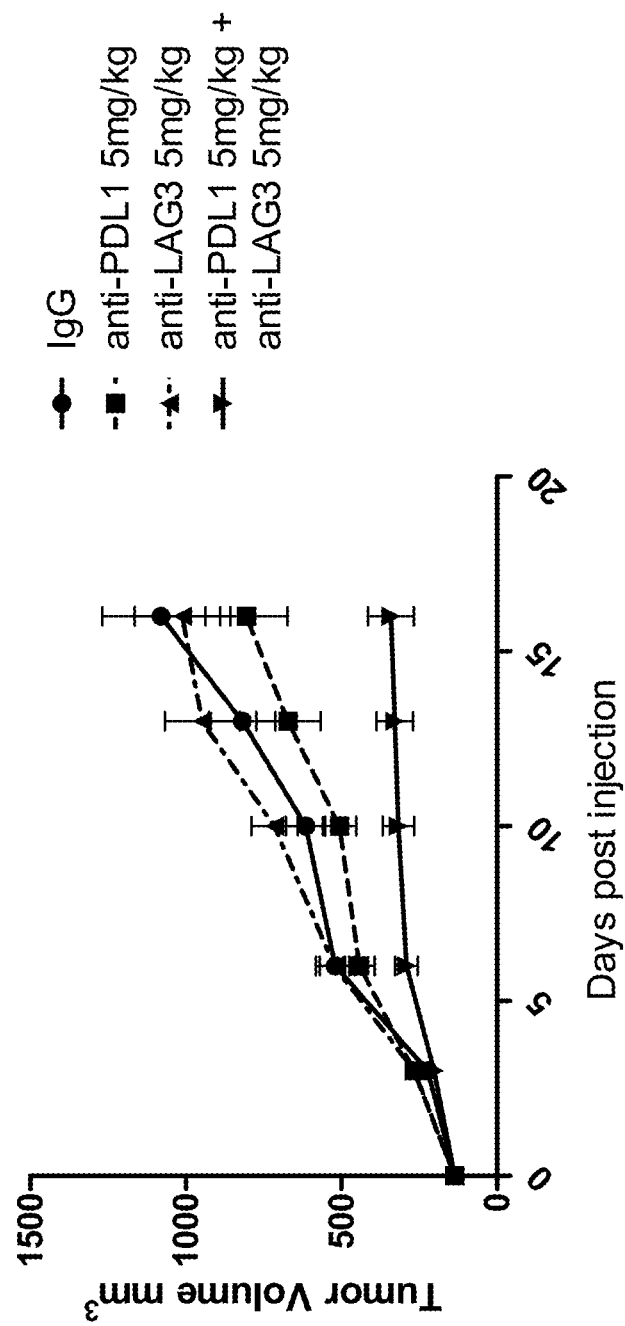
FIG. 17. Combination of anti-PD-L1 antibody and 147H-13 demonstrated robust inhibition of MC38 tumor growth.

Double humanized mice that express the extracellular domain of human PD-1 and human LAG3 were used. Mouse colon adenocarcinoma cells (MC38) were engineered to express human PD-L1. Double humanized mice (hLAG3/hPD-1) were subcutaneously implanted with $5 \times 10^5$ MC38-hPD-L1 cells on day 0. On day 10, mice with an average tumor volume of 137 mm$^3$ were selected and randomized into four treatment groups (N=7/group). Mouse were intraperitoneally administered isotype control (5 mg/kg), anti-PD-L1 antibody (5 mg/kg), anti-LAG3 antibody 147H-13 (5 mg/kg) and anti-PD-L1 antibody (5 mg/kg)+anti-LAG3 antibody (5 mg/kg) every other day for 8 doses, starting from day 10. The anti-PD-L1 antibody used in this example binds with high affinity to human PD-L1 and blocks the interaction with PD-1. Tumor volumes were monitored by caliper measurement twice per week for the duration of the experiment (29 days). Neither the PD-L1 antibody nor 147H-13 showed tumor inhibition at 5 mg/kg. By contrast, combination of the PD-L1 antibody and 147H-13 demonstrated robust inhibition of MC38 tumor growth, with a TGI of 74.2% at the end of the study (FIG. 17). Thus, in an established MC38 colon adenocarcinoma model, a combination treatment of anti-PD-L1 and anti-LAG3 antibodies was significantly more efficacious than the corresponding monotherapies.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A method of treating cancer in a patient in need thereof, comprising administering to the patient an antibody or fragment thereof, wherein the antibody or fragment thereof has specificity to a human Lymphocyte Activation Gene-3 (LAG-3) protein and comprises a heavy chain variable region comprising heavy chain complementarity determining regions CDRH1, CDRH2, and CDRH3, and a light chain variable region comprising light chain complementarity determining regions CDRL1, CDRL2, and CDRL3, and wherein the CDRH1 comprises the amino acid sequence of SEQ ID NO:240;

the CDRH2 comprises the amino acid sequence of SEQ ID NO:241 or SEQ ID NO:347;

the CDRH3 comprises the amino acid sequence of SEQ ID NO:242 or SEQ ID NO:354;

the CDRL1 comprises the amino acid sequence of SEQ ID NO:243, SEQ ID NO:376 or amino acid residues 24-39 of SEQ ID NO:330;

the CDRL2 comprises the amino acid sequence of SEQ ID NO:244; and the CDRL3 comprises the amino acid sequence of SEQ ID NO:245 or SEQ ID NO:374.

2. The method of claim 1, wherein the cancer is selected from the group consisting of a leukemia, a lymphoma, ovarian cancer, breast cancer, endometrial cancer, colon cancer, rectal cancer, bladder cancer, urothelial cancer, lung cancer, bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck, testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, meduloblastoma, astrocytoma, glioma, meningioma, gastrinoma, neuroblastoma, melanoma, myelodysplastic syndrome, and a sarcoma.

3. The method of claim 2, wherein the leukemia is selected from the group consisting of systemic mastocytosis, acute lymphocytic leukemia (ALL), T cell ALL, acute myeloid leukemia (AML), myelogenous leukemia, chronic lymphocytic leukemia (CLL), multiple myeloma (MM), chronic myeloid leukemia (CML), myeloproliferative disorder/neoplasm, myelodysplastic syndrome, monocytic cell leukemia, and plasma cell leukemia; wherein said lymphoma is selected from the group consisting of histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia.

4. A method of treating cancer in a patient in need thereof, comprising:

(a) treating a T cell, in vitro, with an antibody or fragment thereof; and (b) administering the treated T cell to the patient, wherein the antibody or fragment thereof has specificity to a human Lymphocyte Activation Gene-3 (LAG-3) protein and comprises a heavy chain variable region comprising heavy chain complementarity determining regions CDRH1, CDRH2, and CDRH3, and a light chain variable region comprising light chain complementarity determining regions CDRL1, CDRL2, and CDRL3, and wherein the CDRH1 comprises the amino acid sequence of SEQ ID NO:240;

the CDRH2 comprises the amino acid sequence of SEQ ID NO:241 or SEQ ID NO:347;

the CDRH3 comprises the amino acid sequence of SEQ ID NO:242 or SEQ ID NO:354;

the CDRL1 comprises the amino acid sequence of SEQ ID NO:243, SEQ ID NO:376 or amino acid residues 24-39 of SEQ ID NO:330;

the CDRL2 comprises the amino acid sequence of SEQ ID NO:244; and the CDRL3 comprises the amino acid sequence of SEQ ID NO:245 or SEQ ID NO:374.

5. A method of treating cancer in a patient in need thereof, comprising administering to the patient an antibody or fragment thereof, wherein the antibody or fragment thereof has specificity to a human Lymphocyte Activation Gene-3 (LAG-3) protein and comprises (a) a heavy chain variable region comprising the amino acid sequence of SEQ ID NO:329 and a light chain variable region comprising the amino acid sequence of SEQ ID NO:330, or (b) a heavy chain variable region comprising the amino acid sequence of SEQ ID NO:335 and a light chain variable region comprising the amino acid sequence of SEQ ID NO:336.

6. The method of claim 1, wherein the CDRH1 comprises the amino acid sequence of SEQ ID NO:240;

the CDRH2 comprises the amino acid sequence of SEQ ID NO:241;

the CDRH3 comprises the amino acid sequence of SEQ ID NO:242;

the CDRL1 comprises the amino acid sequence of SEQ ID NO:243;

the CDRL2 comprises the amino acid sequence of SEQ ID NO:244; and the CDRL3 comprises the amino acid sequence of SEQ ID NO:245.

7. The method of claim 6, wherein the heavy chain variable region comprises the amino acid sequence of SEQ ID NO:238, and the light chain variable region comprises the amino acid sequences of SEQ ID NO:239.

8. The method of claim 6, wherein the heavy chain variable region comprises an amino acid sequence of selected from the group consisting SEQ ID NO:251, 252, 258 and 259, and the light chain variable region comprises the amino acid sequences of SEQ ID NO:260.

9. The method of claim 1, wherein the CDRH1 comprises the amino acid sequence of SEQ ID NO:240;

the CDRH2 comprises the amino acid sequence of SEQ ID NO:347;

the CDRH3 comprises the amino acid sequence of SEQ ID NO:354;

the CDRL1 comprises the amino acid sequence of amino acid residues 24-39 of SEQ ID NO:330;

the CDRL2 comprises the amino acid sequence of SEQ ID NO:244; and the CDRL3 comprises the amino acid sequence of SEQ ID NO:374.

10. The method of claim 9, wherein the heavy chain variable region comprises the amino acid sequence of SEQ ID NO:329, and the light chain variable region comprises the amino acid sequences of SEQ ID NO:330.

11. The method of claim 1, wherein the CDRH1 comprises the amino acid sequence of SEQ ID NO:240;

the CDRH2 comprises the amino acid sequence of SEQ ID NO:347;

the CDRH3 comprises the amino acid sequence of SEQ ID NO:354;

the CDRL1 comprises the amino acid sequence of SEQ ID NO:376;

the CDRL2 comprises the amino acid sequence of SEQ ID NO:244; and the CDRL3 comprises the amino acid sequence of SEQ ID NO:374.

* * * * *

SEQUENCE LISTING

```
<160> NUMBER OF SEQ ID NOS: 376

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Ala Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Ser Tyr Ala Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic
```

<400> SEQUENCE: 4

Ala Ile Ser Gly Ser Gly Gly Ser Thr Tyr Tyr Ala Asp Ser Val Lys
1               5                   10                  15
Gly

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Ala Arg Gly Ser Ser Trp Phe Asp Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Ala Ser Ser Tyr His Gly Gly Gly Tyr His Arg Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Thr Thr Ser Lys Tyr Ser Gly Ser Ala Leu Arg Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Ala Arg Asp Arg Thr Gly Ala Phe Asp Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Ala Arg His Glu Thr Val Ala Gly Ser Phe Asp Tyr
1               5                   10

<210> SEQ ID NO 10
<211> LENGTH: 15
<212> TYPE: PRT
<213> ORGANISM: Artificial Sequence
<220> FEATURE:

<223> OTHER INFORMATION: Synthetic

<400> SEQUENCE: 10

Ala Arg Thr Gly Tyr Tyr Gly Gly Asn Ser Gly Ala Phe Asp Ile
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Ala Arg Ala Gly Thr Gly Met Asp Leu Val Phe Asn Ser
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ala Arg Gly Leu Ala Arg Gly Asp Leu Asn Phe Gly Tyr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Thr Arg Glu Pro His Phe Asp Tyr
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Thr Thr Ala Ala Pro Gly Ser Tyr Tyr Leu Val Phe His Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Ala Arg Asp Ala Gly Pro Val Gly Tyr Tyr Gly Met Asp Val
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

Ala Gly Asp Gly Leu Tyr Gly Ser Gly Ser Phe Gly Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Ala Lys Asp Ile Arg Trp Phe Tyr Gly Met Asp Val
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Ala Arg His Glu Ser Gly Ile Ala Gly Gly His Phe Asp Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Ala Lys Asp Ile Arg Trp Tyr Tyr Gly Met Asp Val
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Ala Lys Gly Val Arg Gly Thr Tyr Gln Ile Gly Tyr Tyr Gly Met Asp
1               5                   10                  15

Val

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Ala Arg Gln Gly Thr Ala Met Ala Leu Asp Tyr
1               5                   10

<210> SEQ ID NO 22
<211> LENGTH: 14
<212> TYPE: PRT
<213> ORGANISM: Artificial Sequence
<220> FEATURE:

```
<223> OTHER INFORMATION: Synthetic

<400> SEQUENCE: 22

Val Arg Asp Leu Gln Asp Trp Asn Tyr Gly Gly Ala Ala Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Ala Arg Asp Asp Tyr Tyr Tyr Gly Gln Phe Asp Ser
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Ala Arg Glu Ile Thr Gly Thr Ser Tyr Thr Ala Leu Asp Ser
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic

<400> SEQUENCE: 25

Ala Arg Gly His Ile Asp Gly Gln Ala Ala Gly Asp Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic

<400> SEQUENCE: 26

Ala Ala Ser Thr Leu Arg Val Pro Asn Pro Pro Tyr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Ala Arg Ser Gly Asp Arg Tyr Asp Phe Trp Ser Gly Tyr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic
```

<400> SEQUENCE: 28

Thr Arg Gly Gln Asp Ser Thr Trp Tyr Ser Ser Phe Asp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Ala Ala Ser Thr Leu Arg Leu Pro Asn Pro Pro Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Ala Thr Thr Gln Thr Ser Phe Tyr Ser His Gly Met Asp Val
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Ala Arg Val Arg Lys Thr Pro Phe Trp Gly Ala Leu Asp Ser
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic

<400> SEQUENCE: 32

Ala Arg Gly Phe Thr Tyr Gly Asp Phe Ile Phe Asp Tyr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Ala Arg Asp Val Arg Gly Val Thr Tyr Leu Gly Met Asp Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

```
<400> SEQUENCE: 34

Ala Arg Val Arg Lys Thr Pro Phe Trp Gly Thr Leu Asp Ser
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Ala Arg Val Arg Arg Thr Pro Phe Trp Gly Ala Leu Asp Ser
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Ala Lys Arg Lys Gly Leu Gly Ser Pro Thr Asp Tyr Tyr Tyr Gly Met
1               5                   10                  15

Asp Val

<210> SEQ ID NO 37
<211> LENGTH: 14
<212> TYPE: PRT
<213> ORGANISM: Artificial Sequence
<220> FEATURE:
<223> OTHER INFORMATION: Synthetic

<400> SEQUENCE: 37

Val Arg Pro Glu Tyr Asp Thr Tyr Tyr Tyr Gly Met Asp Val
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Ala Lys Gly Gly Gly Ser Tyr Asp Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Ala Arg Ala Leu Asn Gly Met Asp Val
1               5

<210> SEQ ID NO 40
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 40

Thr Arg Pro Leu Gln Gly Ile Ala Ala Ala Asp Ser Tyr Tyr Tyr
1               5                   10                  15

Ala Met Asp Val
            20

<210> SEQ ID NO 41
<211> LENGTH: 13
<212> TYPE: PRT
<213> ORGANISM: Artificial Sequence
<220> FEATURE:
<223> OTHER INFORMATION: Synthetic

<400> SEQUENCE: 41

Ala Arg Leu His Ser Tyr Leu Ser Glu Glu Phe Asp Pro
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Ala Lys Leu Ser Ala Val Asn Thr Tyr Ile Asp Asp
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Ala Arg Val Thr Lys Thr Pro Phe Trp Gly Thr Leu Asp Tyr
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic

<400> SEQUENCE: 44

Ala Arg Val Ser Gln Ser Pro Val Trp Gly Tyr Phe Asp Tyr
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Ala Lys Asp Gly Tyr Tyr Asp Phe Trp Ser Gly Tyr Ser Asp Tyr
1               5                   10                  15

<210> SEQ ID NO 46
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 46

Gln Ala Asn Gln Asp Ile His His Tyr Leu Asn
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Lys Ser Ser Gln Ser Val Leu Tyr Ser Ser Ser Asn Lys Asn Tyr Leu
1               5                   10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Lys Ser Ser Gln Ser Val Leu Tyr Ser Asn Asn Lys Asn Tyr Leu
1               5                   10                  15

Ala

<210> SEQ ID NO 49
<211> LENGTH: 16
<212> TYPE: PRT
<213> ORGANISM: Artificial Sequence
<220> FEATURE:
<223> OTHER INFORMATION: Synthetic

<400> SEQUENCE: 49

Arg Ser Ser Gln Asn Leu Leu His Ser Asp Gly Tyr Asn Tyr Leu Asn
1               5                   10                  15

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Lys Ser Ser Gln Ser Val Leu Tyr Thr Ser Asn Asn Lys Asn Tyr Leu
1               5                   10                  15

Ala

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

Gln Ala Ser Gln Asp Ile Asn Arg Tyr Leu Ser
1               5                   10
```

<210> SEQ ID NO 52
<211> LENGTH: 11
<212> TYPE: PRT
<213> ORGANISM: Artificial Sequence
<220> FEATURE:
<223> OTHER INFORMATION: Synthetic

<400> SEQUENCE: 52

Gln Ala Ser Gln Asp Ile Ser Asn Tyr Leu Asn
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic

<400> SEQUENCE: 53

Arg Ala Ser Gln Thr Ile Ser Ser His Leu Asn
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Arg Ala Ser Gln Gly Ile Ala Gly Trp Leu Ala
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

Arg Ala Ser Gln Gly Val Ser Ser Trp Leu Ala
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Lys Ser Ser Gln Ser Leu Phe Tyr His Ser Asn Asn His Asn Tyr Leu
1               5                   10                  15

Ala

<210> SEQ ID NO 57
<211> LENGTH: 11
<212> TYPE: PRT
<213> ORGANISM: Artificial Sequence
<220> FEATURE:
<223> OTHER INFORMATION: Synthetic

<400> SEQUENCE: 57

Arg Ala Ser Gln Gly Ile Ser Ser Ser Leu Ala
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Gln Ala Ser Arg Asp Ile Ser Asn Ser Leu Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Arg Ala Ser Gln Ser Ile Ser Arg Tyr Leu Asn
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Arg Ala Ser Arg Ser Ile Ser Asn Trp Leu Ala
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

Lys Ser Ser Gln Ser Val Phe Tyr Arg Ser Asn Gln Lys Asn Tyr Leu
1               5                   10                  15

Ala

<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Arg Ala Ser Gln Ser Val Ser Ser Tyr Leu Ala
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Arg Ala Ser Arg Gly Ile Ser Ser Trp Leu Ala

```
<210> SEQ ID NO 64
<211> LENGTH: 11
<212> TYPE: PRT
<213> ORGANISM: Artificial Sequence
<220> FEATURE:
<223> OTHER INFORMATION: Synthetic

<400> SEQUENCE: 64

Arg Ala Ser Gln Gly Ile Ser Ser Trp Leu Ala
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic

<400> SEQUENCE: 65

Arg Ala Ser Gln Ser Ile Ser Ser Tyr Leu Asn
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic

<400> SEQUENCE: 66

Arg Ala Ser Gln Ala Ile Ser Asn Leu Leu Ala
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic

<400> SEQUENCE: 67

Arg Ala Ser Gln Gly Ile Ser Thr Trp Leu Ala
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic

<400> SEQUENCE: 68

Arg Ala Ser Gln Gly Ile Ala Ser Asn Leu Ala
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Arg Ala Ser Gln Gly Val Ser Ser Tyr Leu Ala
1               5                   10
```

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Arg Ala Ser Gln Ser Ile Tyr Thr Tyr Leu Asn
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Arg Ala Ser Gln Phe Val Ser Asp Trp Leu Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Arg Ala Ser Gln Thr Ile Ser Thr Trp Leu Ala
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Arg Ala Ser Gln Gly Ile Ser Ser Tyr Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Arg Ala Ser Gln Ser Ile Gly Tyr Trp Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Arg Ala Thr Gln Ser Ile Ser Ser Trp Leu Ala
1               5                   10

```
<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

Arg Ala Ser Gln Gly Val Arg Asn Trp Leu Ala
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic

<400> SEQUENCE: 77

Arg Ala Ser Gln Ser Ile Asn Asn Tyr Leu Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

Arg Ala Ser Gln Asp Ile Thr Ser Trp Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Arg Ala Ser Gln Gly Ile Tyr Asp Tyr Leu Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Arg Ala Ser Glu Gly Ile Ser Gly Trp Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic

<400> SEQUENCE: 81

Asp Ala Ser Ile Leu Gln Ser
1               5
```

```
<210> SEQ ID NO 82
<211> LENGTH: 7
<212> TYPE: PRT
<213> ORGANISM: Artificial Sequence
<220> FEATURE:
<223> OTHER INFORMATION: Synthetic

<400> SEQUENCE: 82

Trp Ala Ser Thr Arg Glu Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Leu Gly Ser Asn Arg Ala Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic

<400> SEQUENCE: 84

Asp Ala Ser Asn Leu Glu Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Ala Ala Ser Ser Leu Gln Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ala Ala Ser Thr Leu Gln Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Trp Ala Ser Thr Arg Gln Ser
1               5

<210> SEQ ID NO 88
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 88

Ala Ala Phe Ser Leu Gln Ser
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic

<400> SEQUENCE: 89

Gly Ala Ser Ser Arg Ala Thr
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic

<400> SEQUENCE: 90

Gly Ile Ser Ser Arg Ala Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic

<400> SEQUENCE: 91

Ala Val Ser Thr Leu Gln Ser
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Asp Ile Ser Thr Leu Gln Asn
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Gly Ala Ser Thr Leu Gln Ser
1               5

<210> SEQ ID NO 94
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 94

Gly Ala Ser Ser Leu Gln Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Ala Ala Ser Thr Leu Glu Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Asp Ala Ser Ser Leu Gln Ser
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Lys Ala Ser Asn Leu Gln Ser
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Thr Ala Ser Thr Leu Gln Asn
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Arg Ala Ser Ser Leu Gln Ser
1               5

<210> SEQ ID NO 100
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 100

Ala Ala Ser His Leu Gln Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Asp Ala Ser Thr Leu Gln Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ala Ala Ser Asn Leu Glu Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Ala Ala Ser Ser Leu Glu Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Gln Gln Ala Asp Ser Phe Pro Ile Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic

<400> SEQUENCE: 105

Gln Gln Ser Tyr Ser Thr Pro Trp Thr
1               5

<210> SEQ ID NO 106
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 106

Gln Gln Tyr Tyr Ser Thr Pro Trp Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Gln Gln Ser Phe Thr Thr Pro Trp Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

Gln Gln Tyr Asp Asn Leu Pro Pro Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic

<400> SEQUENCE: 109

Gln Gln Ser Tyr Gly Ser Pro Val Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic

<400> SEQUENCE: 110

Gln Gln Gly Asn Ser Phe Pro Phe Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111

Gln Gln Ala Lys Ser Phe Pro Leu Thr
1               5

<210> SEQ ID NO 112
<211> LENGTH: 9
<212> TYPE: PRT
<213> ORGANISM: Artificial Sequence
<220> FEATURE:
```

<223> OTHER INFORMATION: Synthetic

<400> SEQUENCE: 112

Gln Gln Val Lys Ser Phe Pro Leu Thr
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic

<400> SEQUENCE: 113

Gln Gln Tyr Tyr Asn Thr Pro Trp Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Gln Gln Thr Lys Asn Phe Pro Leu Thr
1               5

<210> SEQ ID NO 115
<211> LENGTH: 11
<212> TYPE: PRT
<213> ORGANISM: Artificial Sequence
<220> FEATURE:
<223> OTHER INFORMATION: Synthetic

<400> SEQUENCE: 115

Arg Ala Ser Gln Asp Ile Val Asn Trp Leu Ala
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Gln Gln Thr Lys Ser Phe Pro Leu Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic

<400> SEQUENCE: 117

Gln Gln Ser Tyr Asn Thr Pro Arg Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic

<400> SEQUENCE: 118

Gln Gln Ser Tyr Arg Ala Pro Trp Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic

<400> SEQUENCE: 119

Gln Gln Ala Asn Asn Phe Pro Leu Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Gln Gln Gly Asn Ser Phe Pro Leu Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Gln Gln Ser Lys Asn Phe Pro Val Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Gln Gln Ala Asn Ser Phe Pro Leu Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic

<400> SEQUENCE: 123

Gln Gln Leu Glu Ser Tyr Pro Leu Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic

```
<400> SEQUENCE: 124

Gln Gln Tyr Tyr Ser Ser Pro Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic

<400> SEQUENCE: 125

Gln Gln Leu Lys Thr Phe Pro Leu Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic

<400> SEQUENCE: 126

Gln Gln Thr Asn Trp Phe Pro Leu Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127

Gln Gln Ala Gln Ser Phe Pro Ile Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Ala His Ser Phe Pro Leu Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

Leu Gln Asp Tyr His Phe Pro Leu Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic

<400> SEQUENCE: 130
```

```
Gln Gln Gly His Ser Phe Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gln Gln Ser Tyr Ile Phe Pro Leu Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gln Gln Tyr Asp Thr Tyr Trp Thr
1               5

<210> SEQ ID NO 133
<211> LENGTH: 10
<212> TYPE: PRT
<213> ORGANISM: Artificial Sequence
<220> FEATURE:
<223> OTHER INFORMATION: Synthetic

<400> SEQUENCE: 133

Gln Gln Leu Asn Ser Tyr Pro Leu Phe Thr
1               5                   10

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Gln Gln Tyr Ser Ser Tyr Trp Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic

<400> SEQUENCE: 135

Leu Gln His Asn Thr Tyr Pro Phe Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136
```

```
Gln Gln Gly His Ser Phe Pro Leu Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic

<400> SEQUENCE: 137

Gln Gln Ala His Ser Phe Pro Phe Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Gln Gln Ala Asn Met Phe Pro Leu Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic

<400> SEQUENCE: 139

Gln Gln Ala Asp Ser Phe Pro Phe Thr
1               5

<210> SEQ ID NO 140
<211> LENGTH: 116
<212> TYPE: PRT
<213> ORGANISM: Artificial Sequence
<220> FEATURE:
<223> OTHER INFORMATION: Synthetic

<400> SEQUENCE: 140

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Trp Phe Asp Tyr Trp Gly Gln Gly Thr Leu Val
                100                 105                 110

Thr Val Ser Ser
            115

<210> SEQ ID NO 141
<211> LENGTH: 119
```

```
<212> TYPE: PRT
<213> ORGANISM: Artificial Sequence
<220> FEATURE:
<223> OTHER INFORMATION: Synthetic

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Tyr His Gly Gly Tyr His Arg Tyr Trp Gly Gln Gly
            100                 105                 110

Thr Leu Val Thr Val Ser Ser
        115

<210> SEQ ID NO 142
<211> LENGTH: 119
<212> TYPE: PRT
<213> ORGANISM: Artificial Sequence
<220> FEATURE:
<223> OTHER INFORMATION: Synthetic

<400> SEQUENCE: 142

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Lys Tyr Ser Gly Ser Ala Leu Arg Tyr Trp Gly Gln Gly
            100                 105                 110

Thr Leu Val Thr Val Ser Ser
        115

<210> SEQ ID NO 143
<211> LENGTH: 117
<212> TYPE: PRT
<213> ORGANISM: Artificial Sequence
<220> FEATURE:
<223> OTHER INFORMATION: Synthetic

<400> SEQUENCE: 143

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                    20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Gly Ala Phe Asp Tyr Trp Gly Gln Gly Thr Leu
            100                 105                 110

Val Thr Val Ser Ser
        115

<210> SEQ ID NO 144
<211> LENGTH: 119
<212> TYPE: PRT
<213> ORGANISM: Artificial Sequence
<220> FEATURE:
<223> OTHER INFORMATION: Synthetic

<400> SEQUENCE: 144

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Thr Val Ala Gly Ser Phe Asp Tyr Trp Gly Gln Gly
            100                 105                 110

Thr Leu Val Thr Val Ser Ser
        115

<210> SEQ ID NO 145
<211> LENGTH: 122
<212> TYPE: PRT
<213> ORGANISM: Artificial Sequence
<220> FEATURE:
<223> OTHER INFORMATION: Synthetic

<400> SEQUENCE: 145

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Thr Gly Tyr Tyr Gly Gly Asn Ser Gly Ala Phe Asp Ile Trp
            100                 105                 110

Gly Gln Gly Thr Met Val Thr Val Ser Ser
            115                 120

<210> SEQ ID NO 146
<211> LENGTH: 120
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Thr Gly Met Asp Leu Val Phe Asn Ser Trp Gly Gln
            100                 105                 110

Gly Thr Leu Val Thr Val Ser Ser
            115                 120

<210> SEQ ID NO 147
<211> LENGTH: 120
<212> TYPE: PRT
<213> ORGANISM: Artificial Sequence
<220> FEATURE:
<223> OTHER INFORMATION: Synthetic

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Ala Arg Gly Asp Leu Asn Phe Gly Tyr Trp Gly Gln
            100                 105                 110

Gly Thr Leu Val Thr Val Ser Ser
            115                 120

<210> SEQ ID NO 148
```

```
<211> LENGTH: 115
<212> TYPE: PRT
<213> ORGANISM: Artificial Sequence
<220> FEATURE:
<223> OTHER INFORMATION: Synthetic

<400> SEQUENCE: 148

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Pro His Phe Asp Tyr Trp Gly Gln Gly Thr Leu Val Thr
            100                 105                 110

Val Ser Ser
        115

<210> SEQ ID NO 149
<211> LENGTH: 121
<212> TYPE: PRT
<213> ORGANISM: Artificial Sequence
<220> FEATURE:
<223> OTHER INFORMATION: Synthetic

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Ala Ala Pro Gly Ser Tyr Tyr Leu Val Phe His Tyr Trp Gly
            100                 105                 110

Gln Gly Thr Leu Val Thr Val Ser Ser
        115                 120

<210> SEQ ID NO 150
<211> LENGTH: 121
<212> TYPE: PRT
<213> ORGANISM: Artificial Sequence
<220> FEATURE:
<223> OTHER INFORMATION: Synthetic

<400> SEQUENCE: 150

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Pro Val Gly Tyr Tyr Gly Met Asp Val Trp Gly
            100                 105                 110

Gln Gly Thr Thr Val Thr Val Ser Ser
            115                 120

<210> SEQ ID NO 151
<211> LENGTH: 120
<212> TYPE: PRT
<213> ORGANISM: Artificial Sequence
<220> FEATURE:
<223> OTHER INFORMATION: Synthetic

<400> SEQUENCE: 151

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Asp Gly Leu Tyr Gly Ser Gly Ser Phe Gly Tyr Trp Gly Gln
            100                 105                 110

Gly Thr Pro Val Thr Val Ser Ser
            115                 120

<210> SEQ ID NO 152
<211> LENGTH: 120
<212> TYPE: PRT
<213> ORGANISM: Artificial Sequence
<220> FEATURE:
<223> OTHER INFORMATION: Synthetic

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Lys Asp Ile Arg Trp Phe Tyr Gly Met Asp Val Trp Gly Gln Gly
            100                 105                 110

Thr Thr Val Thr Val Ser Ser Trp
        115                 120

<210> SEQ ID NO 153
<211> LENGTH: 121
<212> TYPE: PRT
<213> ORGANISM: Artificial Sequence
<220> FEATURE:
<223> OTHER INFORMATION: Synthetic

<400> SEQUENCE: 153

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Ser Gly Ile Ala Gly Gly His Phe Asp Tyr Trp Gly
            100                 105                 110

Gln Gly Thr Leu Val Thr Val Ser Ser
        115                 120

<210> SEQ ID NO 154
<211> LENGTH: 120
<212> TYPE: PRT
<213> ORGANISM: Artificial Sequence
<220> FEATURE:
<223> OTHER INFORMATION: Synthetic

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Pro Val Gly Tyr Tyr Gly Met Asp Val Trp Gly
            100                 105                 110

Gln Gly Thr Thr Val Thr Val Ser
        115                 120

-continued

<210> SEQ ID NO 155
<211> LENGTH: 119
<212> TYPE: PRT
<213> ORGANISM: Artificial Sequence
<220> FEATURE:
<223> OTHER INFORMATION: Synthetic

<400> SEQUENCE: 155

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Ile Arg Trp Tyr Tyr Gly Met Asp Val Trp Gly Gln Gly
            100                 105                 110

Thr Thr Val Thr Val Ser Ser
        115
```

<210> SEQ ID NO 156
<211> LENGTH: 124
<212> TYPE: PRT
<213> ORGANISM: Artificial Sequence
<220> FEATURE:
<223> OTHER INFORMATION: Synthetic

<400> SEQUENCE: 156

```
Gln Val Gln Leu Val Gln Ser Gly Ala Glu Val Lys Lys Pro Gly Ser
1               5                   10                  15

Ser Val Lys Val Phe Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Val Arg Gly Thr Tyr Gln Ile Tyr Tyr Gly Met Asp
            100                 105                 110

Val Trp Gly Gln Gly Thr Thr Val Thr Val Ser Ser
        115                 120
```

<210> SEQ ID NO 157
<211> LENGTH: 118
<212> TYPE: PRT
<213> ORGANISM: Artificial Sequence
<220> FEATURE:
<223> OTHER INFORMATION: Synthetic

<400> SEQUENCE: 157

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                      55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Thr Ala Met Ala Leu Asp Tyr Trp Gly Gln Gly Thr
            100                 105                 110

Leu Val Thr Val Ser Ser
            115
```

<210> SEQ ID NO 158
<211> LENGTH: 121
<212> TYPE: PRT
<213> ORGANISM: Artificial Sequence
<220> FEATURE:
<223> OTHER INFORMATION: Synthetic

<400> SEQUENCE: 158

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                      55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Leu Gln Asp Trp Asn Tyr Gly Gly Ala Ala Tyr Trp Gly
            100                 105                 110

Gln Gly Thr Leu Val Thr Val Ser Ser
            115                 120
```

<210> SEQ ID NO 159
<211> LENGTH: 119
<212> TYPE: PRT
<213> ORGANISM: Artificial Sequence
<220> FEATURE:
<223> OTHER INFORMATION: Synthetic

<400> SEQUENCE: 159

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                      55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                85                  90                  95

Ala Arg Asp Asp Tyr Tyr Tyr Gly Gln Phe Asp Ser Trp Gly Gln Gly
            100                 105                 110

Thr Leu Val Thr Val Ser Ser
        115

<210> SEQ ID NO 160
<211> LENGTH: 121
<212> TYPE: PRT
<213> ORGANISM: Artificial Sequence
<220> FEATURE:
<223> OTHER INFORMATION: Synthetic

<400> SEQUENCE: 160

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Thr Gly Thr Ser Tyr Thr Ala Leu Asp Ser Trp Gly
            100                 105                 110

Gln Gly Thr Leu Val Thr Val Ser Ser
        115                 120

<210> SEQ ID NO 161
<211> LENGTH: 120
<212> TYPE: PRT
<213> ORGANISM: Artificial Sequence
<220> FEATURE:
<223> OTHER INFORMATION: Synthetic

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Ile Asp Gly Gln Ala Ala Gly Asp Tyr Trp Gly Gln
            100                 105                 110

Gly Thr Leu Val Thr Val Ser Ser
        115                 120
```

```
<210> SEQ ID NO 162
<211> LENGTH: 119
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Leu Arg Val Pro Asn Pro Pro Tyr Trp Gly Gln Gly
            100                 105                 110

Thr Leu Val Thr Val Ser Ser
        115

<210> SEQ ID NO 163
<211> LENGTH: 120
<212> TYPE: PRT
<213> ORGANISM: Artificial Sequence
<220> FEATURE:
<223> OTHER INFORMATION: Synthetic

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asp Arg Tyr Asp Phe Trp Ser Gly Tyr Trp Gly Gln
            100                 105                 110

Gly Thr Leu Val Thr Val Ser Ser
        115                 120

<210> SEQ ID NO 164
<211> LENGTH: 119
<212> TYPE: PRT
<213> ORGANISM: Artificial Sequence
<220> FEATURE:
<223> OTHER INFORMATION: Synthetic

<400> SEQUENCE: 164

Gln Val Gln Leu Val Gln Ser Gly Ala Glu Val Lys Lys Pro Gly Ser
```

```
                1               5                   10                  15
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Ala Ser Thr Leu Arg Val Pro Asn Pro Pro Tyr Trp Gly Gln Gly
                100                 105                 110

Thr Leu Val Thr Val Ser Ser
            115
```

<210> SEQ ID NO 165
<211> LENGTH: 121
<212> TYPE: PRT
<213> ORGANISM: Artificial Sequence
<220> FEATURE:
<223> OTHER INFORMATION: Synthetic

<400> SEQUENCE: 165

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Asp Ala Gly Pro Val Gly Tyr Tyr Gly Met Asp Val Trp Gly
                100                 105                 110

Gln Gly Thr Met Val Thr Val Ser Ser
            115                 120
```

<210> SEQ ID NO 166
<211> LENGTH: 121
<212> TYPE: PRT
<213> ORGANISM: Artificial Sequence
<220> FEATURE:
<223> OTHER INFORMATION: Synthetic

<400> SEQUENCE: 166

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60
```

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Gln Asp Ser Thr Trp Tyr Ser Ser Phe Asp Tyr Trp Gly
            100                 105                 110

Gln Gly Thr Leu Val Thr Val Ser Ser
            115                 120
```

<210> SEQ ID NO 167
<211> LENGTH: 119
<212> TYPE: PRT
<213> ORGANISM: Artificial Sequence
<220> FEATURE:
<223> OTHER INFORMATION: Synthetic

<400> SEQUENCE: 167

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Leu Arg Leu Pro Asn Pro Pro Tyr Trp Gly Gln Gly
            100                 105                 110

Thr Leu Val Thr Val Ser Ser
        115
```

<210> SEQ ID NO 168
<211> LENGTH: 121
<212> TYPE: PRT
<213> ORGANISM: Artificial Sequence
<220> FEATURE:
<223> OTHER INFORMATION: Synthetic

<400> SEQUENCE: 168

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Gln Thr Ser Phe Tyr Ser His Gly Met Asp Val Trp Gly
            100                 105                 110

Gln Gly Thr Thr Val Thr Val Ser Ser
            115                 120
```

<210> SEQ ID NO 169
<211> LENGTH: 119
<212> TYPE: PRT
<213> ORGANISM: Artificial Sequence
<220> FEATURE:
<223> OTHER INFORMATION: Synthetic

<400> SEQUENCE: 169

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
        115

<210> SEQ ID NO 170
<211> LENGTH: 120
<212> TYPE: PRT
<213> ORGANISM: Artificial Sequence
<220> FEATURE:
<223> OTHER INFORMATION: Synthetic

<400> SEQUENCE: 170

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Thr Tyr Gly Asp Phe Ile Phe Asp Tyr Trp Gly Gln
            100                 105                 110

Gly Thr Leu Val Thr Val Ser Ser
        115                 120

<210> SEQ ID NO 171
<211> LENGTH: 121
<212> TYPE: PRT
<213> ORGANISM: Artificial Sequence
<220> FEATURE:
<223> OTHER INFORMATION: Synthetic

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Val Arg Gly Val Thr Tyr Leu Gly Met Asp Val Trp Gly
            100                 105                 110

Gln Gly Thr Thr Val Thr Val Ser Ser
            115                 120

<210> SEQ ID NO 172
<211> LENGTH: 119
<212> TYPE: PRT
<213> ORGANISM: Artificial Sequence
<220> FEATURE:
<223> OTHER INFORMATION: Synthetic

<400> SEQUENCE: 172

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
            85                  90                  95

Val Arg Lys Thr Pro Phe Trp Gly Thr Leu Asp Ser Trp Gly Arg Gly
            100                 105                 110

Thr Leu Val Thr Val Ser Ser
            115

<210> SEQ ID NO 173
<211> LENGTH: 119
<212> TYPE: PRT
<213> ORGANISM: Artificial Sequence
<220> FEATURE:
<223> OTHER INFORMATION: Synthetic

<400> SEQUENCE: 173

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
50                  55                  60

```
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Arg Arg Thr Pro Phe Trp Gly Ala Leu Asp Ser Trp Gly Arg Gly
            100                 105                 110

Thr Leu Val Thr Val Ser Ser
        115
```

<210> SEQ ID NO 174
<211> LENGTH: 119
<212> TYPE: PRT
<213> ORGANISM: Artificial Sequence
<220> FEATURE:
<223> OTHER INFORMATION: Synthetic

<400> SEQUENCE: 174

```
Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
             20                  25                  30

Ser Trp Val Arg Gln Ala Pro Gly Lys Gly Leu Glu Trp Val Ser Ala
         35                  40                  45

Ile Ser Gly Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Arg Lys Thr Pro Phe Trp Gly Ala Leu Asp Ser Trp Gly Arg Gly
            100                 105                 110

Thr Leu Val Thr Val Ser Ser
        115
```

<210> SEQ ID NO 175
<211> LENGTH: 123
<212> TYPE: PRT
<213> ORGANISM: Artificial Sequence
<220> FEATURE:
<223> OTHER INFORMATION: Synthetic

<400> SEQUENCE: 175

```
Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
             20                  25                  30

Ser Trp Val Arg Gln Ala Pro Gly Lys Gly Leu Glu Trp Val Ser Ala
         35                  40                  45

Ile Ser Gly Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Arg Lys Gly Leu Gly Ser Pro Thr Asp Tyr Tyr Tyr Gly Met Asp Val
            100                 105                 110

Trp Gly Gln Gly Thr Thr Val Thr Val Ser Ser
```

115           120

<210> SEQ ID NO 176
<211> LENGTH: 119
<212> TYPE: PRT
<213> ORGANISM: Artificial Sequence
<220> FEATURE:
<223> OTHER INFORMATION: Synthetic

<400> SEQUENCE: 176

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
        115

<210> SEQ ID NO 177
<211> LENGTH: 119
<212> TYPE: PRT
<213> ORGANISM: Artificial Sequence
<220> FEATURE:
<223> OTHER INFORMATION: Synthetic

<400> SEQUENCE: 177

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Thr Leu Asp Ser Trp Gly Arg Gly
            100                 105                 110

Ser Leu Val Thr Val Ser Ser
        115

<210> SEQ ID NO 178
<211> LENGTH: 119
<212> TYPE: PRT
<213> ORGANISM: Artificial Sequence
<220> FEATURE:
<223> OTHER INFORMATION: Synthetic

<400> SEQUENCE: 178

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Val Arg
                85                  90                  95

Pro Glu Tyr Asp Thr Tyr Tyr Tyr Gly Met Asp Val Trp Gly Gln Gly
            100                 105                 110

Thr Thr Val Thr Val Ser Ser
            115

<210> SEQ ID NO 179
<211> LENGTH: 114
<212> TYPE: PRT
<213> ORGANISM: Artificial Sequence
<220> FEATURE:
<223> OTHER INFORMATION: Synthetic

<400> SEQUENCE: 179

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Gly Gly Gly Ser Tyr Asp Tyr Trp Gly Gln Gly Thr Leu Val Thr Val
            100                 105                 110

Ser Ser

<210> SEQ ID NO 180
<211> LENGTH: 114
<212> TYPE: PRT
<213> ORGANISM: Artificial Sequence
<220> FEATURE:
<223> OTHER INFORMATION: Synthetic

<400> SEQUENCE: 180

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
        50                  55                  60

```
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ala Leu Asn Gly Met Asp Val Trp Gly Gln Gly Thr Met Val Thr Val
            100                 105                 110

Ser Ser
```

<210> SEQ ID NO 181
<211> LENGTH: 125
<212> TYPE: PRT
<213> ORGANISM: Artificial Sequence
<220> FEATURE:
<223> OTHER INFORMATION: Synthetic

<400> SEQUENCE: 181

```
Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                 20                  25                  30

Ser Trp Val Arg Gln Ala Pro Gly Lys Gly Leu Glu Trp Val Ser Ala
             35                  40                  45

Ile Ser Gly Ser Gly Gly Ser Thr Tyr Tyr Ala Asp Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Thr Arg
                 85                  90                  95

Pro Leu Gln Gly Ile Ala Ala Asp Ser Tyr Tyr Tyr Tyr Ala Met
            100                 105                 110

Asp Val Trp Gly Gln Gly Thr Thr Val Thr Val Ser Ser
        115                 120                 125
```

<210> SEQ ID NO 182
<211> LENGTH: 118
<212> TYPE: PRT
<213> ORGANISM: Artificial Sequence
<220> FEATURE:
<223> OTHER INFORMATION: Synthetic

<400> SEQUENCE: 182

```
Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                 20                  25                  30

Ser Trp Val Arg Gln Ala Pro Gly Lys Gly Leu Glu Trp Val Ser Ala
             35                  40                  45

Ile Ser Gly Ser Gly Gly Ser Thr Tyr Tyr Ala Asp Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Leu His Ser Tyr Leu Ser Glu Glu Phe Asp Pro Trp Gly Gln Gly Thr
            100                 105                 110

Leu Val Thr Val Ser Ser
        115
```

<210> SEQ ID NO 183
<211> LENGTH: 119
<212> TYPE: PRT
<213> ORGANISM: Artificial Sequence
<220> FEATURE:
<223> OTHER INFORMATION: Synthetic

<400> SEQUENCE: 183

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
                100                 105                 110

Thr Leu Val Thr Val Ser Ser
        115
```

<210> SEQ ID NO 184
<211> LENGTH: 117
<212> TYPE: PRT
<213> ORGANISM: Artificial Sequence
<220> FEATURE:
<223> OTHER INFORMATION: Synthetic

<400> SEQUENCE: 184

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Ser Gly Ser Gly Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Leu Ser Ala Val Asn Thr Tyr Ile Asp Asp Trp Gly Gln Gly Thr Leu
                100                 105                 110

Val Thr Val Ser Ser
        115
```

<210> SEQ ID NO 185
<211> LENGTH: 119
<212> TYPE: PRT
<213> ORGANISM: Artificial Sequence
<220> FEATURE:
<223> OTHER INFORMATION: Synthetic

<400> SEQUENCE: 185

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Thr Lys Thr Pro Phe Trp Gly Thr Leu Asp Tyr Trp Gly Gln Gly
            100                 105                 110

Thr Leu Val Thr Val Ser Ser
        115

<210> SEQ ID NO 186
<211> LENGTH: 119
<212> TYPE: PRT
<213> ORGANISM: Artificial Sequence
<220> FEATURE:
<223> OTHER INFORMATION: Synthetic

<400> SEQUENCE: 186

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Arg Thr Pro Phe Trp Gly Ala Leu Asp Ser Trp Gly Arg Gly
            100                 105                 110

Thr Leu Val Thr Val Ser Ser
        115

<210> SEQ ID NO 187
<211> LENGTH: 119
<212> TYPE: PRT
<213> ORGANISM: Artificial Sequence
<220> FEATURE:
<223> OTHER INFORMATION: Synthetic

<400> SEQUENCE: 187

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

```
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Ser Gln Ser Pro Val Trp Gly Tyr Phe Asp Tyr Trp Gly Gln Gly
            100                 105                 110

Met Leu Val Thr Val Ser Ser
        115
```

<210> SEQ ID NO 188
<211> LENGTH: 120
<212> TYPE: PRT
<213> ORGANISM: Artificial Sequence
<220> FEATURE:
<223> OTHER INFORMATION: Synthetic

<400> SEQUENCE: 188

```
Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
             35                  40                  45

Ile Ser Gly Ser Gly Gly Ser Thr Tyr Tyr Ala Asp Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Asp Gly Tyr Tyr Asp Phe Trp Ser Gly Tyr Ser Asp Tyr Trp Gly Gln
            100                 105                 110

Gly Thr Leu Val Thr Val Ser Ser
        115                 120
```

<210> SEQ ID NO 189
<211> LENGTH: 108
<212> TYPE: PRT
<213> ORGANISM: Artificial Sequence
<220> FEATURE:
<223> OTHER INFORMATION: Synthetic

<400> SEQUENCE: 189

```
Asp Ile Gln Leu Thr Gln Ser Pro Ser Ser Leu Ser Ala Phe Val Gly
 1               5                  10                  15

Asp Arg Val Thr Ile Thr Cys Gln Ala Asn Gln Asp Ile His His Tyr
                20                  25                  30

Leu Asn Trp Tyr Gln Gln Lys Pro Gly Lys Ala Pro Lys Leu Leu Ile
             35                  40                  45

Tyr Asp Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Ala Asp Ser Phe Pro Ile
                 85                  90                  95

Thr Phe Gly Gln Gly Thr Arg Leu Glu Ile Lys Arg
            100                 105
```

```
<210> SEQ ID NO 190
<211> LENGTH: 114
<212> TYPE: PRT
<213> ORGANISM: Artificial Sequence
<220> FEATURE:
<223> OTHER INFORMATION: Synthetic

<400> SEQUENCE: 190

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ser Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Thr Pro Trp Thr Phe Gly Pro Gly Thr Lys Leu Glu Ile
            100                 105                 110

Lys Arg

<210> SEQ ID NO 191
<211> LENGTH: 114
<212> TYPE: PRT
<213> ORGANISM: Artificial Sequence
<220> FEATURE:
<223> OTHER INFORMATION: Synthetic

<400> SEQUENCE: 191

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly His
        35                  40                  45

Pro Pro Lys Leu Leu Val Tyr Trp Ala Ser Thr Arg Glu Ser Gly Val
    50                  55                  60

Pro Ala Arg Phe Ser Ala Ser Gly Ser Gly Thr Asp Phe Thr Leu Ala
65                  70                  75                  80

Ile Ser Asn Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys Arg

<210> SEQ ID NO 192
<211> LENGTH: 113
<212> TYPE: PRT
<213> ORGANISM: Artificial Sequence
<220> FEATURE:
<223> OTHER INFORMATION: Synthetic

<400> SEQUENCE: 192

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Asn Leu Leu His Ser
```

```
                20                  25                  30
Asp Gly Tyr Asn Tyr Leu Asn Trp Tyr Leu Gln Lys Pro Gly Gln Ser
            35                  40                  45

Pro Gln Leu Leu Ile Tyr Leu Gly Ser Asn Arg Ala Thr Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
                85                  90                  95

Tyr Ser Thr Pro Trp Thr Phe Gly Gln Gly Thr Lys Val Glu Ile Lys
            100                 105                 110

Arg

<210> SEQ ID NO 193
<211> LENGTH: 114
<212> TYPE: PRT
<213> ORGANISM: Artificial Sequence
<220> FEATURE:
<223> OTHER INFORMATION: Synthetic

<400> SEQUENCE: 193

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Pro Trp Thr Phe Gly Gln Gly Thr Lys Leu Glu Ile
            100                 105                 110

Lys Arg

<210> SEQ ID NO 194
<211> LENGTH: 114
<212> TYPE: PRT
<213> ORGANISM: Artificial Sequence
<220> FEATURE:
<223> OTHER INFORMATION: Synthetic

<400> SEQUENCE: 194

Ala Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Ser Ala Thr Tyr Tyr Cys Gln Gln
                85                  90                  95
```

```
Ser Phe Thr Thr Pro Trp Thr Phe Gly Gln Gly Thr Lys Val Glu Ile
                100                 105                 110
Lys Arg

<210> SEQ ID NO 195
<211> LENGTH: 108
<212> TYPE: PRT
<213> ORGANISM: Artificial Sequence
<220> FEATURE:
<223> OTHER INFORMATION: Synthetic

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Ser Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Ala Ser Gly Thr Asp Phe Thr Phe Ala Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Thr Phe Gly Gln Gly Thr Arg Leu Glu Ile Lys Arg
                100                 105

<210> SEQ ID NO 196
<211> LENGTH: 108
<212> TYPE: PRT
<213> ORGANISM: Artificial Sequence
<220> FEATURE:
<223> OTHER INFORMATION: Synthetic

<400> SEQUENCE: 196

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Gly Ser Pro Val
                85                  90                  95

Thr Phe Gly Gln Gly Thr Lys Leu Glu Ile Lys Arg
                100                 105

<210> SEQ ID NO 197
<211> LENGTH: 108
<212> TYPE: PRT
<213> ORGANISM: Artificial Sequence
<220> FEATURE:
<223> OTHER INFORMATION: Synthetic

<400> SEQUENCE: 197

Glu Ile Val Met Thr Gln Ser Pro Ser Ser Leu Ser Ala Ser Val Gly
```

```
1               5                   10                  15
Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Glu Phe Thr Leu Thr Ile Ser Ser Leu Arg Pro
65                  70                  75                  80

Glu Asp Phe Ala Thr Tyr Phe Cys Gln Gln Ala Asp Ser Phe Pro Ile
                85                  90                  95

Thr Phe Gly Gln Gly Thr Arg Leu Glu Ile Lys Arg
                100                 105
```

<210> SEQ ID NO 198
<211> LENGTH: 108
<212> TYPE: PRT
<213> ORGANISM: Artificial Sequence
<220> FEATURE:
<223> OTHER INFORMATION: Synthetic

<400> SEQUENCE: 198

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser His
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Asn Ser Phe Pro Phe
                85                  90                  95

Thr Phe Gly Pro Gly Thr Lys Val Glu Ile Lys Arg
                100                 105
```

<210> SEQ ID NO 199
<211> LENGTH: 108
<212> TYPE: PRT
<213> ORGANISM: Artificial Sequence
<220> FEATURE:
<223> OTHER INFORMATION: Synthetic

<400> SEQUENCE: 199

```
Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Gly Ile Ala Gly Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Ala Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Lys Ser Phe Pro Leu
                85                  90                  95
```

```
Thr Phe Gly Gly Gly Thr Lys Val Glu Ile Lys Arg
            100                 105
```

```
<210> SEQ ID NO 200
<211> LENGTH: 113
<212> TYPE: PRT
<213> ORGANISM: Artificial Sequence
<220> FEATURE:
<223> OTHER INFORMATION: Synthetic

<400> SEQUENCE: 200

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Thr Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Thr Pro Trp Thr Phe Gly Gln Gly Thr Lys Leu Glu Ile
            100                 105                 110

Lys
```

```
<210> SEQ ID NO 201
<211> LENGTH: 108
<212> TYPE: PRT
<213> ORGANISM: Artificial Sequence
<220> FEATURE:
<223> OTHER INFORMATION: Synthetic

<400> SEQUENCE: 201

Asp Ile Val Met Thr Gln Ser Pro Ser Ser Val Ser Ala Phe Val Gly
1               5                  10                  15

Asp Arg Val Thr Ile Thr Cys Arg Ala Ser Gln Gly Val Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Arg Gly Tyr Gly Thr Glu Phe Thr Leu Thr Ile Ser Ser Leu Gln Pro
65                  70                  75                  80

Glu Asp Leu Ala Thr Tyr Tyr Cys Gln Gln Val Lys Ser Phe Pro Leu
                85                  90                  95

Thr Phe Gly Gly Gly Thr Lys Val Asp Ile Lys Arg
            100                 105
```

```
<210> SEQ ID NO 202
<211> LENGTH: 114
<212> TYPE: PRT
<213> ORGANISM: Artificial Sequence
<220> FEATURE:
<223> OTHER INFORMATION: Synthetic

<400> SEQUENCE: 202

Asp Ile Val Met Thr Gln Ser Pro Asp Ser Leu Ala Val Ser Leu Gly
1               5                  10                  15
```

Glu Arg Ala Thr Ile Asn Cys Lys Ser Ser Gln Ser Leu Phe Tyr His
                 20                  25                  30

Ser Asn Asn His Asn Tyr Leu Ala Trp Tyr Gln Gln Lys Pro Gly Gln
             35                  40                  45

Pro Pro Lys Leu Leu Ile Tyr Trp Ala Ser Thr Arg Gln Ser Gly Val
 50                  55                  60

Pro Asp Arg Phe Thr Gly Ser Gly Ser Gly Thr Asp Phe Thr Leu Thr
65                   70                  75                  80

Ile Ser Ser Leu Gln Ala Glu Asp Val Ala Val Tyr Tyr Cys Gln Gln
                 85                  90                  95

Tyr Tyr Asn Thr Pro Trp Thr Phe Gly Gln Gly Thr Lys Val Glu Ile
                100                 105                 110

Lys Arg

<210> SEQ ID NO 203
<211> LENGTH: 108
<212> TYPE: PRT
<213> ORGANISM: Artificial Sequence
<220> FEATURE:
<223> OTHER INFORMATION: Synthetic

<400> SEQUENCE: 203

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Gly Ile Ala Gly Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Ala Ser Gly Thr Asp Phe Thr Leu Thr Ile Ser Asn Leu Gln Pro
65                   70                  75                  80

Glu Asp Phe Ala Thr Tyr Tyr Cys Gln Gln Ala Lys Ser Phe Pro Leu
                 85                  90                  95

Thr Phe Gly Gly Gly Thr Lys Val Glu Ile Lys Arg
                100                 105

<210> SEQ ID NO 204
<211> LENGTH: 108
<212> TYPE: PRT
<213> ORGANISM: Artificial Sequence
<220> FEATURE:
<223> OTHER INFORMATION: Synthetic

<400> SEQUENCE: 204

Asp Ile Val Met Thr Gln Ser Pro Ser Ser Val Ser Ala Phe Val Gly
1               5                   10                  15

Asp Arg Val Thr Ile Thr Cys Arg Ala Ser Gln Gly Val Ser Ser Trp
                 20                  25                  30

Leu Ala Trp Phe Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Arg Gly Tyr Gly Thr Glu Phe Thr Leu Thr Ile Ser Ser Leu Gln Pro
65                   70                  75                  80

Glu Asp Leu Ala Thr Tyr Tyr Cys Gln Gln Val Lys Ser Phe Pro Leu
                 85                  90                  95

-continued

Thr Phe Gly Gly Gly Thr Lys Val Asp Ile Lys Arg
            100                 105

<210> SEQ ID NO 205
<211> LENGTH: 108
<212> TYPE: PRT
<213> ORGANISM: Artificial Sequence
<220> FEATURE:
<223> OTHER INFORMATION: Synthetic

<400> SEQUENCE: 205

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Asn Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Lys Asn Phe Pro Leu
                85                  90                  95

Thr Phe Gly Gln Gly Thr Arg Leu Glu Ile Lys Arg
            100                 105

<210> SEQ ID NO 206
<211> LENGTH: 114
<212> TYPE: PRT
<213> ORGANISM: Artificial Sequence
<220> FEATURE:
<223> OTHER INFORMATION: Synthetic

<400> SEQUENCE: 206

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Arg Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Ala Asp Phe Ser Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Leu Glu Ile
            100                 105                 110

Lys Arg

<210> SEQ ID NO 207
<211> LENGTH: 108
<212> TYPE: PRT
<213> ORGANISM: Artificial Sequence
<220> FEATURE:
<223> OTHER INFORMATION: Synthetic

<400> SEQUENCE: 207

Val Ile Trp Met Thr Gln Ser Pro Ser Ser Leu Ser Ala Ser Val Gly

```
                1               5                   10                  15
            Asp Ser Val Thr Ile Thr Cys Gln Ala Ser Arg Asp Ile Ser Asn Ser
                            20                  25                  30

Leu Ser Trp His Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln Thr Lys Ser Phe Pro Leu
                            85                  90                  95

Thr Phe Gly Gly Gly Thr Lys Val Glu Ile Lys Arg
                        100                 105

<210> SEQ ID NO 208
<211> LENGTH: 108
<212> TYPE: PRT
<213> ORGANISM: Artificial Sequence
<220> FEATURE:
<223> OTHER INFORMATION: Synthetic

<400> SEQUENCE: 208

Glu Ile Val Met Thr Gln Ser Pro Ser Ser Leu Ser Ala Ser Val Gly
            1               5                   10                  15

Asp Arg Val Thr Ile Ser Cys Arg Ala Ser Gln Ser Ile Ser Arg Tyr
                            20                  25                  30

Leu Asn Trp Tyr Gln Gln Lys Pro Gly Gln Ala Pro Lys Leu Leu Ile
                        35                  40                  45

Tyr Ala Ala Phe Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln Ser Tyr Asn Thr Pro Arg
                            85                  90                  95

Thr Phe Gly Gln Gly Thr Lys Leu Glu Ile Lys Arg
                        100                 105

<210> SEQ ID NO 209
<211> LENGTH: 107
<212> TYPE: PRT
<213> ORGANISM: Artificial Sequence
<220> FEATURE:
<223> OTHER INFORMATION: Synthetic

<400> SEQUENCE: 209

Asp Val Val Met Thr Gln Ser Pro Ser Thr Val Ser Ala Ser Val Gly
            1               5                   10                  15

Asp Arg Ile Thr Ile Thr Cys Arg Ala Ser Arg Ser Ile Ser Asn Trp
                            20                  25                  30

Leu Ala Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln Ala Lys Ser Phe Pro Leu
                            85                  90                  95
```

Thr Phe Gly Gly Gly Thr Lys Val Glu Ile Lys
            100                 105

<210> SEQ ID NO 210
<211> LENGTH: 114
<212> TYPE: PRT
<213> ORGANISM: Artificial Sequence
<220> FEATURE:
<223> OTHER INFORMATION: Synthetic

<400> SEQUENCE: 210

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Arg
            20                  25                  30

Ser Asn Gln Lys Asn Tyr Leu Ala Trp Tyr Gln Gln Lys Pro Gly Gln
        35                  40                  45

Thr Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Arg Ala Pro Trp Thr Phe Gly Gln Gly Thr Lys Val Glu Ile
            100                 105                 110

Lys Arg

<210> SEQ ID NO 211
<211> LENGTH: 108
<212> TYPE: PRT
<213> ORGANISM: Artificial Sequence
<220> FEATURE:
<223> OTHER INFORMATION: Synthetic

<400> SEQUENCE: 211

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ile Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Leu Glu Ile Lys Arg
            100                 105

<210> SEQ ID NO 212
<211> LENGTH: 108
<212> TYPE: PRT
<213> ORGANISM: Artificial Sequence
<220> FEATURE:
<223> OTHER INFORMATION: Synthetic

<400> SEQUENCE: 212

Glu Ile Val Leu Thr Gln Ser Pro Ser Ser Val Ser Ala Ser Val Gly
1               5                   10                  15

```
Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys Arg
            100                 105
```

<210> SEQ ID NO 213
<211> LENGTH: 108
<212> TYPE: PRT
<213> ORGANISM: Artificial Sequence
<220> FEATURE:
<223> OTHER INFORMATION: Synthetic

<400> SEQUENCE: 213

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ile Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Leu Glu Ile Lys Arg
            100                 105
```

<210> SEQ ID NO 214
<211> LENGTH: 108
<212> TYPE: PRT
<213> ORGANISM: Artificial Sequence
<220> FEATURE:
<223> OTHER INFORMATION: Synthetic

<400> SEQUENCE: 214

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys Arg
```

<210> SEQ ID NO 215
<211> LENGTH: 108
<212> TYPE: PRT
<213> ORGANISM: Artificial Sequence
<220> FEATURE:
<223> OTHER INFORMATION: Synthetic

<400> SEQUENCE: 215

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Val Ser Thr Leu Gln Ser Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Phe Cys Gln Gln Gly Asn Ser Phe Pro Leu
                85                  90                  95

Thr Phe Gly Gly Gly Thr Lys Val Glu Ile Lys Arg
            100                 105

<210> SEQ ID NO 216
<211> LENGTH: 108
<212> TYPE: PRT
<213> ORGANISM: Artificial Sequence
<220> FEATURE:
<223> OTHER INFORMATION: Synthetic

<400> SEQUENCE: 216

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ala Ile Ser Asn Leu
            20                  25                  30

Leu Ala Trp Tyr Gln Gln Lys Pro Gly Lys Pro Pro Asn Leu Leu Ile
        35                  40                  45

Tyr Asp Ile Ser Thr Leu Gln Asn Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Ile Tyr Tyr Cys Gln Gln Ser Lys Asn Phe Pro Val
                85                  90                  95

Thr Phe Gly Gly Gly Thr Lys Val Glu Ile Lys Arg
            100                 105

<210> SEQ ID NO 217
<211> LENGTH: 108
<212> TYPE: PRT
<213> ORGANISM: Artificial Sequence
<220> FEATURE:
<223> OTHER INFORMATION: Synthetic

<400> SEQUENCE: 217

Asp Ile Gln Leu Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

```
Leu Ala Trp Tyr Gln Gln Lys Pro Gly Lys Ala Pro Lys Leu Leu Ile
            35                  40                  45

Tyr Gly Ala Ser Thr Leu Gln Ser Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Ala Gly Gly Thr Lys Leu Glu Ile Lys Arg
                100                 105

<210> SEQ ID NO 218
<211> LENGTH: 108
<212> TYPE: PRT
<213> ORGANISM: Artificial Sequence
<220> FEATURE:
<223> OTHER INFORMATION: Synthetic

<400> SEQUENCE: 218

Asp Ile Gln Leu Thr Gln Ser Pro Ser Ser Leu Ser Ala Ser Pro Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Asn Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Lys Ser Gly Thr Glu Tyr Thr Leu Thr Ile Ser Ser Leu Gln Pro
65                  70                  75                  80

Glu Asp Phe Ala Thr Tyr Tyr Cys Gln Gln Leu Glu Ser Tyr Pro Leu
                85                  90                  95

Thr Phe Gly Gly Gly Thr Lys Val Glu Ile Lys Arg
                100                 105

<210> SEQ ID NO 219
<211> LENGTH: 113
<212> TYPE: PRT
<213> ORGANISM: Artificial Sequence
<220> FEATURE:
<223> OTHER INFORMATION: Synthetic

<400> SEQUENCE: 219

Ala Ile Arg Met Thr Gln Ser Pro Asp Ser Leu Val Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Ser
65                  70                  75                  80

Ile Ser Ser Leu Gln Ala Glu Asp Val Ala Val Tyr Tyr Cys Gln Gln
                85                  90                  95

Tyr Tyr Ser Ser Pro Thr Phe Gly Gly Gly Thr Lys Val Glu Ile Lys
                100                 105                 110

Arg
```

<210> SEQ ID NO 220
<211> LENGTH: 108
<212> TYPE: PRT
<213> ORGANISM: Artificial Sequence
<220> FEATURE:
<223> OTHER INFORMATION: Synthetic

<400> SEQUENCE: 220

Asp Val Val Met Thr Gln Ser Pro Phe Phe Leu Ser Ala Ser Val Gly
1               5                   10                  15

Asp Arg Val Thr Ile Thr Cys Arg Ala Ser Gln Gly Ile Ala Ser Asn
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Thr Gly
    50                  55                  60

Ser Gly Ser Gly Thr Glu Phe Thr Leu Thr Val Thr Ser Leu Gln Pro
65                  70                  75                  80

Glu Asp Phe Ala Thr Tyr Tyr Cys Gln Gln Leu Lys Thr Phe Pro Leu
                85                  90                  95

Thr Phe Gly Gly Gly Thr Lys Val Glu Ile Lys Arg
            100                 105

<210> SEQ ID NO 221
<211> LENGTH: 108
<212> TYPE: PRT
<213> ORGANISM: Artificial Sequence
<220> FEATURE:
<223> OTHER INFORMATION: Synthetic

<400> SEQUENCE: 221

Val Ile Trp Met Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Asn Trp Phe Pro Leu
                85                  90                  95

Thr Phe Gly Pro Gly Thr Arg Leu Glu Ile Lys Arg
            100                 105

<210> SEQ ID NO 222
<211> LENGTH: 108
<212> TYPE: PRT
<213> ORGANISM: Artificial Sequence
<220> FEATURE:
<223> OTHER INFORMATION: Synthetic

<400> SEQUENCE: 222

Asp Ile Gln Met Thr Gln Ser Pro Ser Ser Leu Ser Thr Ser Ala Gly
1               5                   10                  15

Asp Thr Val Thr Ile Thr Cys Arg Ala Ser Gln Ser Ile Tyr Thr Tyr
            20                  25                  30

Leu Asn Trp Tyr Gln Gln Lys Pro Gly Lys Ala Pro Asn Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Gln Ser Phe Pro Ile
                 85                  90                  95

Thr Phe Gly Gln Gly Thr Arg Leu Glu Ile Lys Arg
            100                 105

<210> SEQ ID NO 223
<211> LENGTH: 108
<212> TYPE: PRT
<213> ORGANISM: Artificial Sequence
<220> FEATURE:
<223> OTHER INFORMATION: Synthetic

<400> SEQUENCE: 223

Val Ile Trp Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Ser Phe Pro Leu
                 85                  90                  95

Thr Phe Gly Gly Gly Thr Lys Val Glu Ile Lys Arg
            100                 105

<210> SEQ ID NO 224
<211> LENGTH: 108
<212> TYPE: PRT
<213> ORGANISM: Artificial Sequence
<220> FEATURE:
<223> OTHER INFORMATION: Synthetic

<400> SEQUENCE: 224

Ala Ile Gln Leu Thr Gln Ser Pro Ser Thr Leu Ser Ala Ser Val Gly
 1               5                  10                  15

Asp Arg Val Thr Ile Thr Cys Arg Ala Ser Gln Phe Val Ser Asp Trp
                 20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Leu Gln Asp Tyr His Phe Pro Leu
                 85                  90                  95

Thr Phe Gly Gly Gly Thr Lys Leu Glu Ile Lys Arg
            100                 105

<210> SEQ ID NO 225

<211> LENGTH: 108
<212> TYPE: PRT
<213> ORGANISM: Artificial Sequence
<220> FEATURE:
<223> OTHER INFORMATION: Synthetic

<400> SEQUENCE: 225

Asp Val Val Met Thr Gln Ser Pro Ser Ser Val Ala Ser Val Gly
1               5                   10                  15

Asp Arg Val Thr Ile Thr Cys Arg Ala Ser Gln Asp Ile Val Asn Trp
            20                  25                  30

Leu Ala Trp Tyr Gln Gln Lys Pro Gly Lys Ala Pro Lys Leu Leu Ile
            35                  40                  45

Tyr Ala Ala Ser Thr Leu Glu Ser Gly Ala Pro Ser Arg Phe Ser Ala
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly His Ser Phe Pro Leu
            85                  90                  95

Thr Phe Gly Pro Gly Thr Lys Leu Glu Ile Lys Arg
            100                 105

<210> SEQ ID NO 226
<211> LENGTH: 108
<212> TYPE: PRT
<213> ORGANISM: Artificial Sequence
<220> FEATURE:
<223> OTHER INFORMATION: Synthetic

<400> SEQUENCE: 226

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Thr Tyr
            20                  25                  30

Leu Asn Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Ser Gly
50                  55                  60

Ser Gly Tyr Gly Thr Glu Phe Thr Leu Thr Ile Ser Gly Leu Gln Pro
65                  70                  75                  80

Glu Asp Phe Ala Thr Tyr Tyr Cys Gln Gln Ser Tyr Ile Phe Pro Leu
            85                  90                  95

Thr Phe Gly Arg Gly Thr Lys Val Glu Ile Lys Arg
            100                 105

<210> SEQ ID NO 227
<211> LENGTH: 107
<212> TYPE: PRT
<213> ORGANISM: Artificial Sequence
<220> FEATURE:
<223> OTHER INFORMATION: Synthetic

<400> SEQUENCE: 227

Ala Ile Arg Met Thr Gln Ser Pro Ser Phe Val Ser Ala Ser Val Gly
1               5                   10                  15

Asp Arg Val Thr Ile Ala Cys Arg Ala Ser Gln Thr Ile Ser Thr Trp
            20                  25                  30

Leu Ala Trp Tyr Gln Gln Lys Pro Gly Lys Ala Pro Lys Val Leu Ile
            35                  40                  45

Ser Lys Ala Ser Asn Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys Arg
            100                 105

<210> SEQ ID NO 228
<211> LENGTH: 107
<212> TYPE: PRT
<213> ORGANISM: Artificial Sequence
<220> FEATURE:
<223> OTHER INFORMATION: Synthetic

<400> SEQUENCE: 228

Ala Ile Arg Met Thr Gln Ser Pro Ser Phe Val Ser Ala Ser Val Gly
1               5                   10                  15

Asp Arg Val Thr Ile Ala Cys Arg Ala Ser Gln Thr Ile Ser Thr Trp
                20                  25                  30

Leu Ala Trp Tyr Gln Gln Lys Pro Gly Lys Ala Pro Lys Val Leu Ile
            35                  40                  45

Ser Lys Ala Ser Asn Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys Arg
            100                 105

<210> SEQ ID NO 229
<211> LENGTH: 109
<212> TYPE: PRT
<213> ORGANISM: Artificial Sequence
<220> FEATURE:
<223> OTHER INFORMATION: Synthetic

<400> SEQUENCE: 229

Asp Ile Val Met Thr Gln Ser Pro Ser Phe Val Ser Ala Ser Val Gly
1               5                   10                  15

Asp Thr Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Phe Thr Phe Gly Pro Gly Thr Lys Val Glu Ile Lys Arg
            100                 105

<210> SEQ ID NO 230
<211> LENGTH: 107
<212> TYPE: PRT
<213> ORGANISM: Artificial Sequence
<220> FEATURE:
<223> OTHER INFORMATION: Synthetic

<400> SEQUENCE: 230

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Tyr Trp
            20                  25                  30

Leu Ala Trp Tyr Gln Gln Lys Pro Gly Lys Ala Pro Lys Leu Leu Ile
        35                  40                  45

Tyr Arg Ala Ser Ser Leu Gln Ser Gly Val Pro Ser Arg Phe Ser Gly
50                  55                  60

Ser Gly Ser Ala Thr Glu Phe Thr Leu Thr Ile Thr Ser Leu Gln Pro
65                  70                  75                  80

Asp Asp Phe Ala Thr Tyr Phe Cys Gln Gln Tyr Ser Ser Tyr Trp Thr
                85                  90                  95

Phe Gly Gln Gly Thr Lys Val Glu Ile Lys Arg
            100                 105

<210> SEQ ID NO 231
<211> LENGTH: 108
<212> TYPE: PRT
<213> ORGANISM: Artificial Sequence
<220> FEATURE:
<223> OTHER INFORMATION: Synthetic

<400> SEQUENCE: 231

Glu Ile Val Leu Thr Gln Ser Pro Ser Ser Leu Ser Ala Ser Val Gly
1               5                   10                  15

Asp Thr Val Thr Ile Thr Cys Arg Ala Thr Gln Ser Ile Ser Ser Trp
            20                  25                  30

Leu Ala Trp Tyr Gln Gln Lys Pro Gly Lys Ala Pro Gln Arg Leu Ile
        35                  40                  45

Ser Gly Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Gln Gly Thr Lys Val Glu Ile Lys Arg
            100                 105

<210> SEQ ID NO 232
<211> LENGTH: 108
<212> TYPE: PRT
<213> ORGANISM: Artificial Sequence
<220> FEATURE:
<223> OTHER INFORMATION: Synthetic

<400> SEQUENCE: 232

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Val Arg Asn Trp
            20                  25                  30

Leu Ala Trp Tyr Gln Gln Lys Pro Gly Lys Ala Pro Lys Leu Leu Ile
        35                  40                  45

Tyr Ala Ala Ser His Leu Gln Ser Gly Val Pro Ser Arg Phe Ser Gly
50                  55                  60

```
Ser Gly Ser Gly Thr Asp Phe Thr Leu Thr Ile Ser Ser Leu Gln Thr
 65                  70                  75                  80

Asp Asp Phe Ala Thr Tyr Tyr Cys Gln Gln Gly His Ser Phe Pro Leu
             85                  90                  95

Thr Phe Gly Gly Gly Thr Lys Val Glu Ile Lys Arg
            100                 105

<210> SEQ ID NO 233
<211> LENGTH: 108
<212> TYPE: PRT
<213> ORGANISM: Artificial Sequence
<220> FEATURE:
<223> OTHER INFORMATION: Synthetic

<400> SEQUENCE: 233

Asp Ile Val Met Thr Gln Ser Pro Ser Ser Val Ser Ala Ser Val Gly
 1               5                  10                  15

Asp Arg Val Thr Ile Thr Cys Arg Ala Ser Gln Gly Val Arg Asn Trp
                 20                  25                  30

Leu Ala Trp Tyr Gln Gln Lys Pro Gly Lys Ala Pro Lys Leu Leu Ile
             35                  40                  45

Tyr Ala Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Thr
 65                  70                  75                  80

Asp Asp Phe Ala Thr Tyr Tyr Cys Gln Gln Gly His Ser Phe Pro Leu
             85                  90                  95

Thr Phe Gly Gly Gly Thr Lys Val Glu Ile Lys Arg
            100                 105

<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234

Val Ile Trp Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Asn Tyr
                 20                  25                  30

Leu Ala Trp Tyr Gln Gln Lys Pro Gly Lys Ala Pro Lys Leu Leu Ile
             35                  40                  45

Tyr Asp Ala Ser Thr Leu Gln Ser Gly Val Pro Ser Arg Phe Ser Gly
 50                  55                  60

Gly Gly Ser Gly Thr Asp Phe Thr Leu Thr Ile Asn Ser Leu Gln Pro
 65                  70                  75                  80

Asp Asp Phe Ala Ser Tyr Tyr Cys Gln Gln Ala His Ser Phe Pro Phe
             85                  90                  95

Thr Phe Gly Gly Gly Thr Lys Leu Glu Ile Lys Arg
            100                 105

<210> SEQ ID NO 235
<211> LENGTH: 108
<212> TYPE: PRT
<213> ORGANISM: Artificial Sequence
<220> FEATURE:
<223> OTHER INFORMATION: Synthetic
```

<400> SEQUENCE: 235

Glu Ile Val Met Thr Gln Ser Pro Ser Val Ser Ala Ser Val Gly
1               5                   10                  15

Asp Arg Val Thr Ile Thr Cys Arg Ala Ser Gln Asp Ile Thr Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Thr Gly Leu Gln Pro
65                  70                  75                  80

Glu Asp Phe Ala Thr Tyr Tyr Cys Gln Gln Ala Asn Met Phe Pro Leu
                85                  90                  95

Thr Phe Gly Gly Gly Thr Lys Val Glu Ile Lys Arg
            100                 105

<210> SEQ ID NO 236
<211> LENGTH: 108
<212> TYPE: PRT
<213> ORGANISM: Artificial Sequence
<220> FEATURE:
<223> OTHER INFORMATION: Synthetic

<400> SEQUENCE: 236

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asp Tyr
            20                  25                  30

Leu Ala Trp Tyr Gln Gln Lys Pro Gly Lys Ala Pro Ser Leu Leu Ile
        35                  40                  45

Tyr Ala Ala Ser Asn Leu Glu Arg Gly Val Pro Ser Arg Phe Ser Gly
    50                  55                  60

Ser Gly Ser Gly Lys Tyr Phe Ile Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 237
<211> LENGTH: 108
<212> TYPE: PRT
<213> ORGANISM: Artificial Sequence
<220> FEATURE:
<223> OTHER INFORMATION: Synthetic

<400> SEQUENCE: 237

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Gly Ile Ser Gly Trp
            20                  25                  30

Leu Ala Trp Tyr Gln Gln Ile Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Phe
                85                  90                  95

Thr Phe Gly Pro Gly Thr Lys Val Glu Ile Lys Arg
            100                 105

<210> SEQ ID NO 238
<211> LENGTH: 116
<212> TYPE: PRT
<213> ORGANISM: Artificial Sequence
<220> FEATURE:
<223> OTHER INFORMATION: Synthetic

<400> SEQUENCE: 238

Gln Val Gln Leu Gln Gln Ser Gly Ser Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Ile Lys Gln Arg Pro Gly His Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Ser Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Pro Asn Leu Pro Gly Asp Tyr Trp Gly Gln Gly Thr Ser Val
            100                 105                 110

Thr Val Ser Ser
        115

<210> SEQ ID NO 239
<211> LENGTH: 112
<212> TYPE: PRT
<213> ORGANISM: Artificial Sequence
<220> FEATURE:
<223> OTHER INFORMATION: Synthetic

<400> SEQUENCE: 239

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Gly Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 240
<211> LENGTH: 10
<212> TYPE: PRT
<213> ORGANISM: Artificial Sequence
<220> FEATURE:
<223> OTHER INFORMATION: Synthetic

```
<400> SEQUENCE: 240

Gly Tyr Thr Phe Thr Asn Tyr Trp Leu Gly
1               5                   10

<210> SEQ ID NO 241
<211> LENGTH: 17
<212> TYPE: PRT
<213> ORGANISM: Artificial Sequence
<220> FEATURE:
<223> OTHER INFORMATION: Synthetic

<400> SEQUENCE: 241

Asp Ile Tyr Pro Gly Gly Asp Tyr Ile Asn Tyr Asn Glu Lys Phe Lys
1               5                   10                  15

Gly

<210> SEQ ID NO 242
<211> LENGTH: 7
<212> TYPE: PRT
<213> ORGANISM: Artificial Sequence
<220> FEATURE:
<223> OTHER INFORMATION: Synthetic

<400> SEQUENCE: 242

Pro Asn Leu Pro Gly Asp Tyr
1               5

<210> SEQ ID NO 243
<211> LENGTH: 16
<212> TYPE: PRT
<213> ORGANISM: Artificial Sequence
<220> FEATURE:
<223> OTHER INFORMATION: Synthetic

<400> SEQUENCE: 243

Arg Ser Ser Lys Ser Leu Leu His Ser Asn Gly Ile Thr Tyr Leu Tyr
1               5                   10                  15

<210> SEQ ID NO 244
<211> LENGTH: 7
<212> TYPE: PRT
<213> ORGANISM: Artificial Sequence
<220> FEATURE:
<223> OTHER INFORMATION: Synthetic

<400> SEQUENCE: 244

Gln Val Ser Asn Leu Ala Ser
1               5

<210> SEQ ID NO 245
<211> LENGTH: 9
<212> TYPE: PRT
<213> ORGANISM: Artificial Sequence
<220> FEATURE:
<223> OTHER INFORMATION: Synthetic

<400> SEQUENCE: 245

Ala Gln Asn Leu Glu Leu Pro Trp Thr
1               5

<210> SEQ ID NO 246
<211> LENGTH: 116
<212> TYPE: PRT
<213> ORGANISM: Artificial Sequence
<220> FEATURE:
<223> OTHER INFORMATION: Synthetic
```

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 247
<211> LENGTH: 116
<212> TYPE: PRT
<213> ORGANISM: Artificial Sequence
<220> FEATURE:
<223> OTHER INFORMATION: Synthetic

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 248
<211> LENGTH: 116
<212> TYPE: PRT
<213> ORGANISM: Artificial Sequence
<220> FEATURE:
<223> OTHER INFORMATION: Synthetic

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
            50                  55                  60

Lys Gly Arg Val Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
                100                 105                 110

Thr Val Ser Ser
            115

<210> SEQ ID NO 249
<211> LENGTH: 116
<212> TYPE: PRT
<213> ORGANISM: Artificial Sequence
<220> FEATURE:
<223> OTHER INFORMATION: Synthetic

<400> SEQUENCE: 249

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Trp Leu Gly Trp Val Arg Gln Ala Pro Gly Gln Gly Leu Glu Trp Met
             35                  40                  45

Gly Asp Ile Tyr Pro Gly Gly Asp Tyr Ile Asn Tyr Asn Glu Lys Phe
            50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
                100                 105                 110

Thr Val Ser Ser
            115

<210> SEQ ID NO 250
<211> LENGTH: 116
<212> TYPE: PRT
<213> ORGANISM: Artificial Sequence
<220> FEATURE:
<223> OTHER INFORMATION: Synthetic

<400> SEQUENCE: 250

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Trp Leu Gly Trp Val Arg Gln Ala Pro Gly Gln Gly Leu Glu Trp Ile
             35                  40                  45

Gly Asp Ile Tyr Pro Gly Gly Asp Tyr Ile Asn Tyr Asn Glu Lys Phe
            50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val

Thr Val Ser Ser
        115

<210> SEQ ID NO 251
<211> LENGTH: 116
<212> TYPE: PRT
<213> ORGANISM: Artificial Sequence
<220> FEATURE:
<223> OTHER INFORMATION: Synthetic

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 252
<211> LENGTH: 116
<212> TYPE: PRT
<213> ORGANISM: Artificial Sequence
<220> FEATURE:
<223> OTHER INFORMATION: Synthetic

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 253
<211> LENGTH: 116
<212> TYPE: PRT
<213> ORGANISM: Artificial Sequence
<220> FEATURE:

<223> OTHER INFORMATION: Synthetic

<400> SEQUENCE: 253

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 254
<211> LENGTH: 116
<212> TYPE: PRT
<213> ORGANISM: Artificial Sequence
<220> FEATURE:
<223> OTHER INFORMATION: Synthetic

<400> SEQUENCE: 254

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 255
<211> LENGTH: 116
<212> TYPE: PRT
<213> ORGANISM: Artificial Sequence
<220> FEATURE:
<223> OTHER INFORMATION: Synthetic

<400> SEQUENCE: 255

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met

```
            35                  40                  45

Gly Asp Ile Tyr Pro Gly Gly Asp Tyr Ile Asn Tyr Asn Glu Lys Phe
         50                  55                  60

Lys Gly Arg Val Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 256
<211> LENGTH: 116
<212> TYPE: PRT
<213> ORGANISM: Artificial Sequence
<220> FEATURE:
<223> OTHER INFORMATION: Synthetic

<400> SEQUENCE: 256

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Trp Leu Gly Trp Val Arg Gln Ala Pro Gly Gln Gly Leu Glu Trp Met
         35                  40                  45

Gly Asp Ile Tyr Pro Gly Gly Asp Tyr Ile Asn Tyr Asn Glu Lys Phe
         50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 257
<211> LENGTH: 116
<212> TYPE: PRT
<213> ORGANISM: Artificial Sequence
<220> FEATURE:
<223> OTHER INFORMATION: Synthetic

<400> SEQUENCE: 257

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Trp Leu Gly Trp Val Arg Gln Ala Pro Gly Gln Gly Leu Glu Trp Ile
         35                  40                  45

Gly Asp Ile Tyr Pro Gly Gly Asp Tyr Ile Asn Tyr Asn Glu Lys Phe
         50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95
```

Ala Arg Pro Asn Leu Pro Gly Asp Tyr Trp Gly Gln Gly Thr Thr Val
            100                 105                 110

Thr Val Ser Ser
        115

<210> SEQ ID NO 258
<211> LENGTH: 116
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 259
<211> LENGTH: 116
<212> TYPE: PRT
<213> ORGANISM: Artificial Sequence
<220> FEATURE:
<223> OTHER INFORMATION: Synthetic

<400> SEQUENCE: 259

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 260
<211> LENGTH: 112
<212> TYPE: PRT
<213> ORGANISM: Artificial Sequence

```
<220> FEATURE:
<223> OTHER INFORMATION: Synthetic

<400> SEQUENCE: 260

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 261
<211> LENGTH: 116
<212> TYPE: PRT
<213> ORGANISM: Artificial Sequence
<220> FEATURE:
<223> OTHER INFORMATION: Synthetic

<400> SEQUENCE: 261

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115

<210> SEQ ID NO 262
<211> LENGTH: 112
<212> TYPE: PRT
<213> ORGANISM: Artificial Sequence
<220> FEATURE:
<223> OTHER INFORMATION: Synthetic

<400> SEQUENCE: 262

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45
```

-continued

```
Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110
```

<210> SEQ ID NO 263
<211> LENGTH: 116
<212> TYPE: PRT
<213> ORGANISM: Artificial Sequence
<220> FEATURE:
<223> OTHER INFORMATION: Synthetic

<400> SEQUENCE: 263

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asp Leu Pro Gly Asp Tyr Trp Gly Gln Gly Thr Thr Val
            100                 105                 110

Thr Val Ser Ser
            115
```

<210> SEQ ID NO 264
<211> LENGTH: 112
<212> TYPE: PRT
<213> ORGANISM: Artificial Sequence
<220> FEATURE:
<223> OTHER INFORMATION: Synthetic

<400> SEQUENCE: 264

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110
```

<210> SEQ ID NO 265

```
<211> LENGTH: 116
<212> TYPE: PRT
<213> ORGANISM: Artificial Sequence
<220> FEATURE:
<223> OTHER INFORMATION: Synthetic

<400> SEQUENCE: 265

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Lys Asp Tyr Trp Gly Gln Gly Thr Thr Val
            100                 105                 110

Thr Val Ser Ser
        115

<210> SEQ ID NO 266
<211> LENGTH: 112
<212> TYPE: PRT
<213> ORGANISM: Artificial Sequence
<220> FEATURE:
<223> OTHER INFORMATION: Synthetic

<400> SEQUENCE: 266

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 267
<211> LENGTH: 116
<212> TYPE: PRT
<213> ORGANISM: Artificial Sequence
<220> FEATURE:
<223> OTHER INFORMATION: Synthetic

<400> SEQUENCE: 267

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

```
Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
 50                      55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Lys Asp Tyr Trp Gly Gln Gly Thr Thr Val
                100                 105                 110

Thr Val Ser Ser
            115
```

<210> SEQ ID NO 268
<211> LENGTH: 112
<212> TYPE: PRT
<213> ORGANISM: Artificial Sequence
<220> FEATURE:
<223> OTHER INFORMATION: Synthetic

<400> SEQUENCE: 268

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                 20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
                100                 105                 110
```

<210> SEQ ID NO 269
<211> LENGTH: 116
<212> TYPE: PRT
<213> ORGANISM: Artificial Sequence
<220> FEATURE:
<223> OTHER INFORMATION: Synthetic

<400> SEQUENCE: 269

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
 50                      55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Arg Asp Tyr Trp Gly Gln Gly Thr Thr Val
                100                 105                 110
```

Thr Val Ser Ser
        115

<210> SEQ ID NO 270
<211> LENGTH: 112
<212> TYPE: PRT
<213> ORGANISM: Artificial Sequence
<220> FEATURE:
<223> OTHER INFORMATION: Synthetic

<400> SEQUENCE: 270

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 271
<211> LENGTH: 116
<212> TYPE: PRT
<213> ORGANISM: Artificial Sequence
<220> FEATURE:
<223> OTHER INFORMATION: Synthetic

<400> SEQUENCE: 271

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Arg Asp Tyr Trp Gly Gln Gly Thr Thr Val
            100                 105                 110

Thr Val Ser Ser
        115

<210> SEQ ID NO 272
<211> LENGTH: 112
<212> TYPE: PRT
<213> ORGANISM: Artificial Sequence
<220> FEATURE:
<223> OTHER INFORMATION: Synthetic

<400> SEQUENCE: 272

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 273
<211> LENGTH: 116
<212> TYPE: PRT
<213> ORGANISM: Artificial Sequence
<220> FEATURE:
<223> OTHER INFORMATION: Synthetic

<400> SEQUENCE: 273

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Gln Asp Tyr Trp Gly Gln Gly Thr Thr Val
            100                 105                 110

Thr Val Ser Ser
        115

<210> SEQ ID NO 274
<211> LENGTH: 112
<212> TYPE: PRT
<213> ORGANISM: Artificial Sequence
<220> FEATURE:
<223> OTHER INFORMATION: Synthetic

<400> SEQUENCE: 274

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 275
<211> LENGTH: 116
<212> TYPE: PRT
<213> ORGANISM: Artificial Sequence
<220> FEATURE:
<223> OTHER INFORMATION: Synthetic

<400> SEQUENCE: 275

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asp Leu Pro Lys Asp Tyr Trp Gly Gln Gly Thr Thr Val
            100                 105                 110

Thr Val Ser Ser
        115

<210> SEQ ID NO 276
<211> LENGTH: 112
<212> TYPE: PRT
<213> ORGANISM: Artificial Sequence
<220> FEATURE:
<223> OTHER INFORMATION: Synthetic

<400> SEQUENCE: 276

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 277
<211> LENGTH: 116
<212> TYPE: PRT
<213> ORGANISM: Artificial Sequence
<220> FEATURE:
<223> OTHER INFORMATION: Synthetic

<400> SEQUENCE: 277

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 278
<211> LENGTH: 112
<212> TYPE: PRT
<213> ORGANISM: Artificial Sequence
<220> FEATURE:
<223> OTHER INFORMATION: Synthetic

<400> SEQUENCE: 278

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 279
<211> LENGTH: 116
<212> TYPE: PRT
<213> ORGANISM: Artificial Sequence
<220> FEATURE:
<223> OTHER INFORMATION: Synthetic

<400> SEQUENCE: 279

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
50                  55                  60

```
Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 280
<211> LENGTH: 112
<212> TYPE: PRT
<213> ORGANISM: Artificial Sequence
<220> FEATURE:
<223> OTHER INFORMATION: Synthetic

<400> SEQUENCE: 280

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
             35                  40                  45

Pro Gln Leu Leu Ile Tyr Gln Val Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Met Pro Trp Thr Phe Gly Gly Gly Thr Lys Val Glu Ile Lys
            100                 105                 110

<210> SEQ ID NO 281
<211> LENGTH: 116
<212> TYPE: PRT
<213> ORGANISM: Artificial Sequence
<220> FEATURE:
<223> OTHER INFORMATION: Synthetic

<400> SEQUENCE: 281

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
             35                  40                  45

Gly Asp Ile Tyr Pro Gly Gly Asp Tyr Ile Asn Tyr Asn Glu Lys Phe
     50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115
```

```
<210> SEQ ID NO 282
<211> LENGTH: 112
<212> TYPE: PRT
<213> ORGANISM: Artificial Sequence
<220> FEATURE:
<223> OTHER INFORMATION: Synthetic

<400> SEQUENCE: 282
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Met Pro Trp Thr Phe Gly Gly Gly Thr Lys Val Glu Ile Lys
            100                 105                 110

```
<210> SEQ ID NO 283
<211> LENGTH: 116
<212> TYPE: PRT
<213> ORGANISM: Artificial Sequence
<220> FEATURE:
<223> OTHER INFORMATION: Synthetic

<400> SEQUENCE: 283
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

```
<210> SEQ ID NO 284
<211> LENGTH: 112
<212> TYPE: PRT
<213> ORGANISM: Artificial Sequence
<220> FEATURE:
<223> OTHER INFORMATION: Synthetic

<400> SEQUENCE: 284
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Glu Pro Trp Thr Phe Gly Gly Gly Thr Lys Val Glu Ile Lys
            100                 105                 110

<210> SEQ ID NO 285
<211> LENGTH: 116
<212> TYPE: PRT
<213> ORGANISM: Artificial Sequence
<220> FEATURE:
<223> OTHER INFORMATION: Synthetic

<400> SEQUENCE: 285

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 286
<211> LENGTH: 112
<212> TYPE: PRT
<213> ORGANISM: Artificial Sequence
<220> FEATURE:
<223> OTHER INFORMATION: Synthetic

<400> SEQUENCE: 286

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys

<210> SEQ ID NO 287
<211> LENGTH: 116
<212> TYPE: PRT
<213> ORGANISM: Artificial Sequence
<220> FEATURE:
<223> OTHER INFORMATION: Synthetic

<400> SEQUENCE: 287

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
                100                 105                 110

Thr Val Ser Ser
            115

<210> SEQ ID NO 288
<211> LENGTH: 112
<212> TYPE: PRT
<213> ORGANISM: Artificial Sequence
<220> FEATURE:
<223> OTHER INFORMATION: Synthetic

<400> SEQUENCE: 288

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
                100                 105                 110

<210> SEQ ID NO 289
<211> LENGTH: 116
<212> TYPE: PRT
<213> ORGANISM: Artificial Sequence
<220> FEATURE:
<223> OTHER INFORMATION: Synthetic

<400> SEQUENCE: 289

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115

<210> SEQ ID NO 290
<211> LENGTH: 112
<212> TYPE: PRT
<213> ORGANISM: Artificial Sequence
<220> FEATURE:
<223> OTHER INFORMATION: Synthetic

<400> SEQUENCE: 290

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Glu Pro Trp Thr Phe Gly Gly Gly Thr Lys Val Glu Ile Lys
            100                 105                 110

<210> SEQ ID NO 291
<211> LENGTH: 116
<212> TYPE: PRT
<213> ORGANISM: Artificial Sequence
<220> FEATURE:
<223> OTHER INFORMATION: Synthetic

<400> SEQUENCE: 291

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys

-continued

```
                    85                  90                  95
Ala Arg Pro Asn Leu Pro Lys Asp His Trp Gly Gln Gly Thr Thr Val
                100                 105                 110

Thr Val Ser Ser
        115

<210> SEQ ID NO 292
<211> LENGTH: 112
<212> TYPE: PRT
<213> ORGANISM: Artificial Sequence
<220> FEATURE:
<223> OTHER INFORMATION: Synthetic

<400> SEQUENCE: 292

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
                100                 105                 110

<210> SEQ ID NO 293
<211> LENGTH: 116
<212> TYPE: PRT
<213> ORGANISM: Artificial Sequence
<220> FEATURE:
<223> OTHER INFORMATION: Synthetic

<400> SEQUENCE: 293

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
                100                 105                 110

Thr Val Ser Ser
        115

<210> SEQ ID NO 294
<211> LENGTH: 112
<212> TYPE: PRT
<213> ORGANISM: Artificial Sequence
<220> FEATURE:
```

<223> OTHER INFORMATION: Synthetic

<400> SEQUENCE: 294

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Arg Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 295
<211> LENGTH: 116
<212> TYPE: PRT
<213> ORGANISM: Artificial Sequence
<220> FEATURE:
<223> OTHER INFORMATION: Synthetic

<400> SEQUENCE: 295

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 296
<211> LENGTH: 112
<212> TYPE: PRT
<213> ORGANISM: Artificial Sequence
<220> FEATURE:
<223> OTHER INFORMATION: Synthetic

<400> SEQUENCE: 296

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Lys Ser Asn Leu Ala Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
                100                 105                 110
```

<210> SEQ ID NO 297
<211> LENGTH: 116
<212> TYPE: PRT
<213> ORGANISM: Artificial Sequence
<220> FEATURE:
<223> OTHER INFORMATION: Synthetic

<400> SEQUENCE: 297

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Asp Asn Tyr
                 20                  25                  30

Trp Leu Gly Trp Ile Lys Gln Ala Pro Gly Gln Gly Leu Glu Trp Ile
             35                  40                  45

Gly Asp Ile Tyr Pro Gly Gly Asp Ile Ile Asn Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
                100                 105                 110

Thr Val Ser Ser
            115
```

<210> SEQ ID NO 298
<211> LENGTH: 112
<212> TYPE: PRT
<213> ORGANISM: Artificial Sequence
<220> FEATURE:
<223> OTHER INFORMATION: Synthetic

<400> SEQUENCE: 298

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Lys Ser Leu Leu His Ser
                 20                  25                  30

Asn Ala Ile Thr Tyr Leu Tyr Trp Tyr Leu Gln Lys Pro Gly Gln Ser
             35                  40                  45

Pro Gln Leu Leu Ile Tyr Gln Val Ser Asn Leu Ala Val Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
                100                 105                 110
```

<210> SEQ ID NO 299
<211> LENGTH: 116

```
<212> TYPE: PRT
<213> ORGANISM: Artificial Sequence
<220> FEATURE:
<223> OTHER INFORMATION: Synthetic

<400> SEQUENCE: 299

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Val Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 300
<211> LENGTH: 112
<212> TYPE: PRT
<213> ORGANISM: Artificial Sequence
<220> FEATURE:
<223> OTHER INFORMATION: Synthetic

<400> SEQUENCE: 300

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Leu Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 301
<211> LENGTH: 116
<212> TYPE: PRT
<213> ORGANISM: Artificial Sequence
<220> FEATURE:
<223> OTHER INFORMATION: Synthetic

<400> SEQUENCE: 301

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Trp Trp Ile Lys Gln Ala Pro Gly Gln Gly Leu Glu Trp Ile
```

```
                35                  40                  45
Gly Asp Ile Phe Pro Gly Gly Asp Tyr Ile Asn Tyr Asn Glu Lys Phe
 50                  55                  60
Lys Gly Lys Ala Thr Leu Thr Ala Asp Thr Ser Ile Ser Thr Ala Tyr
 65                  70                  75                  80
Met Glu Leu Ser Arg Leu Arg Ser Asp Thr Ala Val Tyr Tyr Cys
                 85                  90                  95
Ala Arg Pro Asn Leu Pro Gly Asp Tyr Trp Gly Gln Gly Thr Thr Val
                100                 105                 110
Thr Val Ser Ser
        115

<210> SEQ ID NO 302
<211> LENGTH: 112
<212> TYPE: PRT
<213> ORGANISM: Artificial Sequence
<220> FEATURE:
<223> OTHER INFORMATION: Synthetic

<400> SEQUENCE: 302

Asp Ile Val Met Thr Gln Ser Pro Leu Ser Leu Pro Val Thr Pro Gly
 1               5                  10                  15
Glu Pro Ala Ser Ile Ser Cys Arg Ser Ser Lys Ser Leu Leu His Ser
                20                  25                  30
Asn Ala Ile Thr Tyr Leu Tyr Trp Tyr Leu Gln Lys Pro Gly Gln Ser
            35                  40                  45
Pro Gln Leu Leu Ile Tyr Gln Val Asp Asn Leu Ala Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Ala Gln Asn
                 85                  90                  95
Leu Glu Leu Pro Trp Thr Phe Gly Gly Gly Thr Lys Val Glu Ile Lys
                100                 105                 110

<210> SEQ ID NO 303
<211> LENGTH: 116
<212> TYPE: PRT
<213> ORGANISM: Artificial Sequence
<220> FEATURE:
<223> OTHER INFORMATION: Synthetic

<400> SEQUENCE: 303

Glu Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asn Tyr
                20                  25                  30
Trp Leu Gly Trp Ile Lys Gln Ala Pro Gly Gln Gly Leu Glu Trp Ile
            35                  40                  45
Gly Asp Ile Tyr Pro Gly Gly Asp Tyr Ile Val Tyr Asn Glu Lys Phe
 50                  55                  60
Lys Gly Lys Ala Thr Leu Thr Ala Asp Thr Ser Ile Ser Thr Ala Tyr
 65                  70                  75                  80
Met Glu Leu Ser Arg Leu Arg Ser Asp Thr Ala Val Tyr Tyr Cys
                 85                  90                  95
Ala Arg Pro Asn Leu Pro Gly Asp Tyr Trp Gly Gln Gly Thr Thr Val
                100                 105                 110
```

Thr Val Ser Ser
        115

<210> SEQ ID NO 304
<211> LENGTH: 112
<212> TYPE: PRT
<213> ORGANISM: Artificial Sequence
<220> FEATURE:
<223> OTHER INFORMATION: Synthetic

<400> SEQUENCE: 304

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 305
<211> LENGTH: 116
<212> TYPE: PRT
<213> ORGANISM: Artificial Sequence
<220> FEATURE:
<223> OTHER INFORMATION: Synthetic

<400> SEQUENCE: 305

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 306
<211> LENGTH: 112
<212> TYPE: PRT
<213> ORGANISM: Artificial Sequence
<220> FEATURE:
<223> OTHER INFORMATION: Synthetic

<400> SEQUENCE: 306

Asp Ile Val Met Thr Gln Ser Pro Leu Ser Leu Pro Val Thr Pro Gly

```
                1               5                  10                  15
            Glu Pro Ala Ser Ile Ser Cys Arg Ser Ser Lys Ser Leu Leu His Ser
                            20                  25                  30

Asn Ala Ile Thr Tyr Leu Tyr Trp Tyr Leu Gln Lys Pro Gly Gln Ser
                            35                  40                  45

Pro Gln Leu Leu Ile Tyr Gln Val Ser Asn Leu Ala Ser Gly Val Pro
                            50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Ala Gln Asn
                            85                  90                  95

Leu Glu Leu Pro Trp Thr Phe Gly Gly Gly Thr Lys Val Glu Ile Lys
                            100                 105                 110
```

<210> SEQ ID NO 307
<211> LENGTH: 116
<212> TYPE: PRT
<213> ORGANISM: Artificial Sequence
<220> FEATURE:
<223> OTHER INFORMATION: Synthetic

<400> SEQUENCE: 307

```
            Glu Val Gln Leu Val Gln Ser Gly Ala Glu Val Lys Lys Pro Gly Ala
            1               5                  10                  15

Ser Val Lys Val Ser Cys Lys Ala Ser Gly Tyr Thr Phe Thr Asn Tyr
                            20                  25                  30

Trp Leu Gly Trp Ile Lys Gln Ala Pro Gly Gln Gly Leu Glu Trp Ile
                            35                  40                  45

Gly Asp Ile Tyr Pro Gly Gly Asp Tyr Ile Asn Tyr Asn Glu Lys Phe
                            50                  55                  60

Lys Gly Lys Ala Thr Leu Thr Ala Asp Thr Ser Ile Ser Thr Ala Tyr
            65                  70                  75                  80

Met Glu Leu Ser Arg Leu Arg Ser Asp Asp Thr Ala Val Tyr Tyr Cys
                            85                  90                  95

Ala Arg Pro Asn Leu Pro Gly Asp Tyr Trp Gly Gln Gly Thr Thr Val
                            100                 105                 110

Thr Val Ser Ser
                    115
```

<210> SEQ ID NO 308
<211> LENGTH: 112
<212> TYPE: PRT
<213> ORGANISM: Artificial Sequence
<220> FEATURE:
<223> OTHER INFORMATION: Synthetic

<400> SEQUENCE: 308

```
            Asp Ile Val Met Thr Gln Ser Pro Leu Ser Leu Pro Val Thr Pro Gly
            1               5                  10                  15

Glu Pro Ala Ser Ile Ser Cys Arg Ser Ser Lys Ser Leu Leu His Ser
                            20                  25                  30

Asn Ala Ile Thr Tyr Leu Tyr Trp Tyr Leu Gln Lys Pro Gly Gln Ser
                            35                  40                  45

Pro Gln Leu Leu Ile Tyr His Val Ser Asn Leu Ala Ser Gly Val Pro
                            50                  55                  60

Asp Arg Phe Ser Gly Ser Gly Ser Gly Thr Asp Phe Thr Leu Lys Ile
            65                  70                  75                  80
```

-continued

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 309
<211> LENGTH: 116
<212> TYPE: PRT
<213> ORGANISM: Artificial Sequence
<220> FEATURE:
<223> OTHER INFORMATION: Synthetic

<400> SEQUENCE: 309

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Trp Trp Ile Lys Gln Ala Pro Gly Gln Gly Leu Glu Trp Ile
            35                  40                  45

Gly Asp Ile Tyr Pro Gly Gly Asp Leu Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 310
<211> LENGTH: 112
<212> TYPE: PRT
<213> ORGANISM: Artificial Sequence
<220> FEATURE:
<223> OTHER INFORMATION: Synthetic

<400> SEQUENCE: 310

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr His Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 311
<211> LENGTH: 116
<212> TYPE: PRT
<213> ORGANISM: Artificial Sequence
<220> FEATURE:
<223> OTHER INFORMATION: Synthetic -continued

<400> SEQUENCE: 311

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Ser Trp Ile Lys Gln Ala Pro Gly Gln Gly Leu Glu Trp Ile
        35                  40                  45

Gly Asp Ile Tyr Pro Gly Gly Asp His Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 312
<211> LENGTH: 112
<212> TYPE: PRT
<213> ORGANISM: Artificial Sequence
<220> FEATURE:
<223> OTHER INFORMATION: Synthetic

<400> SEQUENCE: 312

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 313
<211> LENGTH: 116
<212> TYPE: PRT
<213> ORGANISM: Artificial Sequence
<220> FEATURE:
<223> OTHER INFORMATION: Synthetic

<400> SEQUENCE: 313

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Trp Trp Ile Lys Gln Ala Pro Gly Gln Gly Leu Glu Trp Ile
        35                  40                  45

Gly Glu Ile Tyr Pro Gly Gly Asp Tyr Ile Thr Tyr Asn Glu Lys Phe
    50                  55                  60

```
Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
            100                 105                 110

<210> SEQ ID NO 315
<211> LENGTH: 116
<212> TYPE: PRT
<213> ORGANISM: Artificial Sequence
<220> FEATURE:
<223> OTHER INFORMATION: Synthetic

<400> SEQUENCE: 315

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 316
```

```
<211> LENGTH: 112
<212> TYPE: PRT
<213> ORGANISM: Artificial Sequence
<220> FEATURE:
<223> OTHER INFORMATION: Synthetic

<400> SEQUENCE: 316

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Asp Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 317
<211> LENGTH: 116
<212> TYPE: PRT
<213> ORGANISM: Artificial Sequence
<220> FEATURE:
<223> OTHER INFORMATION: Synthetic

<400> SEQUENCE: 317

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 318
<211> LENGTH: 112
<212> TYPE: PRT
<213> ORGANISM: Artificial Sequence
<220> FEATURE:
<223> OTHER INFORMATION: Synthetic

<400> SEQUENCE: 318

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30
```

```
Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110
```

<210> SEQ ID NO 319
<211> LENGTH: 116
<212> TYPE: PRT
<213> ORGANISM: Artificial Sequence
<220> FEATURE:
<223> OTHER INFORMATION: Synthetic

<400> SEQUENCE: 319

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115
```

<210> SEQ ID NO 320
<211> LENGTH: 112
<212> TYPE: PRT
<213> ORGANISM: Artificial Sequence
<220> FEATURE:
<223> OTHER INFORMATION: Synthetic

<400> SEQUENCE: 320

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Thr Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110
```

<210> SEQ ID NO 321
<211> LENGTH: 116
<212> TYPE: PRT
<213> ORGANISM: Artificial Sequence
<220> FEATURE:
<223> OTHER INFORMATION: Synthetic

<400> SEQUENCE: 321

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 323
<211> LENGTH: 116
<212> TYPE: PRT
<213> ORGANISM: Artificial Sequence
<220> FEATURE:
<223> OTHER INFORMATION: Synthetic

<400> SEQUENCE: 323

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 324
<211> LENGTH: 112
<212> TYPE: PRT
<213> ORGANISM: Artificial Sequence
<220> FEATURE:
<223> OTHER INFORMATION: Synthetic

<400> SEQUENCE: 324

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 325
<211> LENGTH: 116
<212> TYPE: PRT
<213> ORGANISM: Artificial Sequence
<220> FEATURE:
<223> OTHER INFORMATION: Synthetic

<400> SEQUENCE: 325

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Pro Asn Leu Pro Gly Asp Tyr Trp Gly Gln Gly Thr Thr Val
            100                 105                 110

Thr Val Ser Ser
        115

<210> SEQ ID NO 326
<211> LENGTH: 112
<212> TYPE: PRT
<213> ORGANISM: Artificial Sequence
<220> FEATURE:
<223> OTHER INFORMATION: Synthetic

<400> SEQUENCE: 326

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 327
<211> LENGTH: 116
<212> TYPE: PRT
<213> ORGANISM: Artificial Sequence
<220> FEATURE:
<223> OTHER INFORMATION: Synthetic

<400> SEQUENCE: 327

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 328
<211> LENGTH: 112
<212> TYPE: PRT
<213> ORGANISM: Artificial Sequence
<220> FEATURE:
<223> OTHER INFORMATION: Synthetic
```

<400> SEQUENCE: 328

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 329
<211> LENGTH: 116
<212> TYPE: PRT
<213> ORGANISM: Artificial Sequence
<220> FEATURE:
<223> OTHER INFORMATION: Synthetic

<400> SEQUENCE: 329

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
            115

<210> SEQ ID NO 330
<211> LENGTH: 112
<212> TYPE: PRT
<213> ORGANISM: Artificial Sequence
<220> FEATURE:
<223> OTHER INFORMATION: Synthetic

<400> SEQUENCE: 330

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
            85                  90                  95

Leu Glu Leu Pro Trp Thr Phe Gly Gly Gly Thr Lys Val Glu Ile Lys
        100                 105                 110

<210> SEQ ID NO 331
<211> LENGTH: 116
<212> TYPE: PRT
<213> ORGANISM: Artificial Sequence
<220> FEATURE:
<223> OTHER INFORMATION: Synthetic

<400> SEQUENCE: 331

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Pro Asn Leu Pro Lys Asp His Trp Gly Gln Gly Thr Thr Val
        100                 105                 110

Thr Val Ser Ser
        115

<210> SEQ ID NO 332
<211> LENGTH: 112
<212> TYPE: PRT
<213> ORGANISM: Artificial Sequence
<220> FEATURE:
<223> OTHER INFORMATION: Synthetic

<400> SEQUENCE: 332

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Tyr
            85                  90                  95

Leu Glu Leu Pro Trp Thr Phe Gly Gly Gly Thr Lys Val Glu Ile Lys
        100                 105                 110

<210> SEQ ID NO 333
<211> LENGTH: 116
<212> TYPE: PRT

<213> ORGANISM: Artificial Sequence
<220> FEATURE:
<223> OTHER INFORMATION: Synthetic

<400> SEQUENCE: 333

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Leu Phe Thr Asn Tyr
            20                  25                  30
Trp Leu Gly Trp Ile Lys Gln Ala Pro Gly Gln Gly Leu Glu Trp Ile
        35                  40                  45
Gly Asp Ile Tyr Pro Gly Gly Asp Tyr Ile Val Tyr Asn Glu Lys Phe
50                  55                  60
Lys Gly Lys Ala Thr Leu Thr Ala Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Pro Asn Leu Pro Lys Asp His Trp Gly Gln Gly Thr Thr Val
            100                 105                 110
Thr Val Ser Ser
        115
```

<210> SEQ ID NO 334
<211> LENGTH: 112
<212> TYPE: PRT
<213> ORGANISM: Artificial Sequence
<220> FEATURE:
<223> OTHER INFORMATION: Synthetic

<400> SEQUENCE: 334

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Lys Ser Leu Leu His Ser
            20                  25                  30
Asn Ala Ile Thr Tyr Leu Tyr Trp Tyr Leu Gln Lys Pro Gly Gln Ser
        35                  40                  45
Pro Gln Leu Leu Ile Tyr Gln Val Ser Asn Leu Ala Ser Gly Val Pro
50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Tyr
                85                  90                  95
Leu Glu Leu Pro Trp Thr Phe Gly Gly Gly Thr Lys Val Glu Ile Lys
            100                 105                 110
```

<210> SEQ ID NO 335
<211> LENGTH: 116
<212> TYPE: PRT
<213> ORGANISM: Artificial Sequence
<220> FEATURE:
<223> OTHER INFORMATION: Synthetic

<400> SEQUENCE: 335

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Leu Phe Thr Asn Tyr
            20                  25                  30
Trp Leu Gly Trp Ile Lys Gln Ala Pro Gly Gln Gly Leu Glu Trp Ile
        35                  40                  45
```

Gly Asp Ile Tyr Pro Gly Gly Asp Tyr Ile Val Tyr Asn Glu Lys Phe
            50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115

<210> SEQ ID NO 336
<211> LENGTH: 112
<212> TYPE: PRT
<213> ORGANISM: Artificial Sequence
<220> FEATURE:
<223> OTHER INFORMATION: Synthetic

<400> SEQUENCE: 336

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 337
<211> LENGTH: 116
<212> TYPE: PRT
<213> ORGANISM: Artificial Sequence
<220> FEATURE:
<223> OTHER INFORMATION: Synthetic

<400> SEQUENCE: 337

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser

<210> SEQ ID NO 338
<211> LENGTH: 112
<212> TYPE: PRT
<213> ORGANISM: Artificial Sequence
<220> FEATURE:
<223> OTHER INFORMATION: Synthetic

<400> SEQUENCE: 338

Asp Ile Val Met Thr Gln Ser Pro Leu Ser Leu Pro Val Thr Pro Gly
1               5                   10                  15
Glu Pro Ala Ser Ile Ser Cys Arg Ser Ser Lys Ser Leu Leu His Ser
            20                  25                  30
Asn Ala Ile Thr Tyr Leu Tyr Trp Tyr Leu Gln Lys Pro Gly Gln Ser
        35                  40                  45
Pro Gln Leu Leu Ile Tyr Gln Val Ser Asn Leu Ala Thr Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Gly Gln Tyr
                85                  90                  95
Leu Glu Leu Pro Trp Thr Phe Gly Gly Gly Thr Lys Val Glu Ile Lys
            100                 105                 110

<210> SEQ ID NO 339
<211> LENGTH: 10
<212> TYPE: PRT
<213> ORGANISM: Artificial Sequence
<220> FEATURE:
<223> OTHER INFORMATION: Synthetic

<400> SEQUENCE: 339

Gly Tyr Thr Phe Glu Asn Tyr Trp Leu Gly
1               5                   10

<210> SEQ ID NO 340
<211> LENGTH: 10
<212> TYPE: PRT
<213> ORGANISM: Artificial Sequence
<220> FEATURE:
<223> OTHER INFORMATION: Synthetic

<400> SEQUENCE: 340

Gly Tyr Met Phe Thr Asn Tyr Trp Leu Gly
1               5                   10

<210> SEQ ID NO 341
<211> LENGTH: 10
<212> TYPE: PRT
<213> ORGANISM: Artificial Sequence
<220> FEATURE:
<223> OTHER INFORMATION: Synthetic

<400> SEQUENCE: 341

Gly Tyr Thr Phe Asp Asn Tyr Trp Leu Gly
1               5                   10

<210> SEQ ID NO 342
<211> LENGTH: 10
<212> TYPE: PRT
<213> ORGANISM: Artificial Sequence
<220> FEATURE:
<223> OTHER INFORMATION: Synthetic

<400> SEQUENCE: 342

Gly Tyr Thr Phe Gly Asn Tyr Trp Leu Gly
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic

<400> SEQUENCE: 343

Gly Tyr Thr Phe Thr Asn Tyr Trp Leu Trp
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Synthetic

<400> SEQUENCE: 344

Gly Tyr Leu Phe Thr Asn Tyr Trp Leu Gly
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Synthetic

<400> SEQUENCE: 345

Gly Tyr Thr Phe Thr Asn Tyr Trp Leu Ser
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Synthetic

<400> SEQUENCE: 346

Gly Phe Thr Phe Thr Asn Tyr Trp Leu Gly
1               5                   10

<210> SEQ ID NO 347
<211> LENGTH: 17
<212> TYPE: PRT
<213> ORGANISM: Artificial Sequence
<220> FEATURE:
<223> OTHER INFORMATION: Synthetic

<400> SEQUENCE: 347

Asp Ile Tyr Pro Gly Gly Asp Tyr Ile Val Tyr Asn Glu Lys Phe Lys
1               5                   10                  15

Gly

<210> SEQ ID NO 348
<211> LENGTH: 17
<212> TYPE: PRT
<213> ORGANISM: Artificial Sequence
<220> FEATURE:

<223> OTHER INFORMATION: Synthetic

<400> SEQUENCE: 348

Asp Ile Tyr Pro Gly Gly Asp Ile Ile Asn Tyr Asn Glu Lys Phe Lys
1               5                   10                  15
Gly

<210> SEQ ID NO 349
<211> LENGTH: 17
<212> TYPE: PRT
<213> ORGANISM: Artificial Sequence
<220> FEATURE:
<223> OTHER INFORMATION: Synthetic

<400> SEQUENCE: 349

Asp Ile Tyr Pro Gly Gly Asp Val Ile Asn Tyr Asn Glu Lys Phe Lys
1               5                   10                  15
Gly

<210> SEQ ID NO 350
<211> LENGTH: 17
<212> TYPE: PRT
<213> ORGANISM: Artificial Sequence
<220> FEATURE:
<223> OTHER INFORMATION: Synthetic

<400> SEQUENCE: 350

Asp Ile Phe Pro Gly Gly Asp Tyr Ile Asn Tyr Asn Glu Lys Phe Lys
1               5                   10                  15
Gly

<210> SEQ ID NO 351
<211> LENGTH: 17
<212> TYPE: PRT
<213> ORGANISM: Artificial Sequence
<220> FEATURE:
<223> OTHER INFORMATION: Synthetic

<400> SEQUENCE: 351

Asp Ile Tyr Pro Gly Gly Asp Leu Ile Asn Tyr Asn Glu Lys Phe Lys
1               5                   10                  15
Gly

<210> SEQ ID NO 352
<211> LENGTH: 17
<212> TYPE: PRT
<213> ORGANISM: Artificial Sequence
<220> FEATURE:
<223> OTHER INFORMATION: Synthetic

<400> SEQUENCE: 352

Asp Ile Tyr Pro Gly Gly Asp His Ile Asn Tyr Asn Glu Lys Phe Lys
1               5                   10                  15
Gly

<210> SEQ ID NO 353
<211> LENGTH: 17
<212> TYPE: PRT
<213> ORGANISM: Artificial Sequence
<220> FEATURE:
<223> OTHER INFORMATION: Synthetic

<400> SEQUENCE: 353

Glu Ile Tyr Pro Gly Gly Asp Tyr Ile Thr Tyr Asn Glu Lys Phe Lys
1               5                   10                  15

Gly

<210> SEQ ID NO 354
<211> LENGTH: 7
<212> TYPE: PRT
<213> ORGANISM: Artificial Sequence
<220> FEATURE:
<223> OTHER INFORMATION: Synthetic

<400> SEQUENCE: 354

Pro Asn Leu Pro Lys Asp His
1               5

<210> SEQ ID NO 355
<211> LENGTH: 7
<212> TYPE: PRT
<213> ORGANISM: Artificial Sequence
<220> FEATURE:
<223> OTHER INFORMATION: Synthetic

<400> SEQUENCE: 355

Pro Asp Leu Pro Gly Asp Tyr
1               5

<210> SEQ ID NO 356
<211> LENGTH: 7
<212> TYPE: PRT
<213> ORGANISM: Artificial Sequence
<220> FEATURE:
<223> OTHER INFORMATION: Synthetic

<400> SEQUENCE: 356

Pro Gly Leu Pro Lys Asp Tyr
1               5

<210> SEQ ID NO 357
<211> LENGTH: 7
<212> TYPE: PRT
<213> ORGANISM: Artificial Sequence
<220> FEATURE:
<223> OTHER INFORMATION: Synthetic

<400> SEQUENCE: 357

Pro Asn Leu Pro Lys Asp Tyr
1               5

<210> SEQ ID NO 358
<211> LENGTH: 7
<212> TYPE: PRT
<213> ORGANISM: Artificial Sequence
<220> FEATURE:
<223> OTHER INFORMATION: Synthetic

<400> SEQUENCE: 358

Pro Asn Leu Pro Arg Asp Tyr
1               5

<210> SEQ ID NO 359
<211> LENGTH: 7
<212> TYPE: PRT
<213> ORGANISM: Artificial Sequence
<220> FEATURE:
<223> OTHER INFORMATION: Synthetic

<400> SEQUENCE: 359

```
Pro Gly Leu Pro Arg Asp Tyr
1               5

<210> SEQ ID NO 360
<211> LENGTH: 7
<212> TYPE: PRT
<213> ORGANISM: Artificial Sequence
<220> FEATURE:
<223> OTHER INFORMATION: Synthetic

<400> SEQUENCE: 360

Pro Gly Leu Pro Gln Asp Tyr
1               5

<210> SEQ ID NO 361
<211> LENGTH: 7
<212> TYPE: PRT
<213> ORGANISM: Artificial Sequence
<220> FEATURE:
<223> OTHER INFORMATION: Synthetic

<400> SEQUENCE: 361

Pro Asp Leu Pro Lys Asp Tyr
1               5

<210> SEQ ID NO 362
<211> LENGTH: 7
<212> TYPE: PRT
<213> ORGANISM: Artificial Sequence
<220> FEATURE:
<223> OTHER INFORMATION: Synthetic

<400> SEQUENCE: 362

Gln Val Ser Asn Leu Ala Arg
1               5

<210> SEQ ID NO 363
<211> LENGTH: 7
<212> TYPE: PRT
<213> ORGANISM: Artificial Sequence
<220> FEATURE:
<223> OTHER INFORMATION: Synthetic

<400> SEQUENCE: 363

Gln Lys Ser Asn Leu Ala Ser
1               5

<210> SEQ ID NO 364
<211> LENGTH: 7
<212> TYPE: PRT
<213> ORGANISM: Artificial Sequence
<220> FEATURE:
<223> OTHER INFORMATION: Synthetic

<400> SEQUENCE: 364

Gln Val Ser Asn Leu Ala Val
1               5

<210> SEQ ID NO 365
<211> LENGTH: 7
<212> TYPE: PRT
<213> ORGANISM: Artificial Sequence
<220> FEATURE:
<223> OTHER INFORMATION: Synthetic

<400> SEQUENCE: 365
```

Gln Val Ser Asn Leu Ala Leu
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic

<400> SEQUENCE: 366

Gln Val Asp Asn Leu Ala Ser
1               5

<210> SEQ ID NO 367
<211> LENGTH: 7
<212> TYPE: PRT
<213> ORGANISM: Artificial Sequence
<220> FEATURE:
<223> OTHER INFORMATION: Synthetic

<400> SEQUENCE: 367

Gln Val Ser Asn Leu Ala Thr
1               5

<210> SEQ ID NO 368
<211> LENGTH: 7
<212> TYPE: PRT
<213> ORGANISM: Artificial Sequence
<220> FEATURE:
<223> OTHER INFORMATION: Synthetic

<400> SEQUENCE: 368

His Val Ser Asn Leu Ala Ser
1               5

<210> SEQ ID NO 369
<211> LENGTH: 7
<212> TYPE: PRT
<213> ORGANISM: Artificial Sequence
<220> FEATURE:
<223> OTHER INFORMATION: Synthetic

<400> SEQUENCE: 369

Gln Val Ser Asn Arg Ala Ser
1               5

<210> SEQ ID NO 370
<211> LENGTH: 9
<212> TYPE: PRT
<213> ORGANISM: Artificial Sequence
<220> FEATURE:
<223> OTHER INFORMATION: Synthetic

<400> SEQUENCE: 370

Gly Gln Asn Leu Glu Leu Pro Trp Thr
1               5

<210> SEQ ID NO 371
<211> LENGTH: 9
<212> TYPE: PRT
<213> ORGANISM: Artificial Sequence
<220> FEATURE:
<223> OTHER INFORMATION: Synthetic

<400> SEQUENCE: 371

Ala Gln Asn Leu Glu Met Pro Trp Thr

```
<210> SEQ ID NO 372
<211> LENGTH: 9
<212> TYPE: PRT
<213> ORGANISM: Artificial Sequence
<220> FEATURE:
<223> OTHER INFORMATION: Synthetic

<400> SEQUENCE: 372

Gly Gln Asn Leu Glu Met Pro Trp Thr
1               5

<210> SEQ ID NO 373
<211> LENGTH: 9
<212> TYPE: PRT
<213> ORGANISM: Artificial Sequence
<220> FEATURE:
<223> OTHER INFORMATION: Synthetic

<400> SEQUENCE: 373

Ala Gln Tyr Leu Glu Glu Pro Trp Thr
1               5

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374

Ala Gln Tyr Leu Glu Leu Pro Trp Thr
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic

<400> SEQUENCE: 375

Gly Gln Tyr Leu Glu Leu Pro Trp Thr
1               5

<210> SEQ ID NO 376
<211> LENGTH: 16
<212> TYPE: PRT
<213> ORGANISM: Artificial Sequence
<220> FEATURE:
<223> OTHER INFORMATION: Synthetic

<400> SEQUENCE: 376

Arg Ser Ser Lys Ser Leu Leu His Ser Gln Gly Ile Thr Tyr Leu Tyr
1               5                   10                  15
```